United States Patent
Belousov et al.

(10) Patent No.: US 10,975,423 B2
(45) Date of Patent: Apr. 13, 2021

(54) METHODS FOR TRUE ISOTHERMAL STRAND DISPLACEMENT AMPLIFICATION

(71) Applicant: ELITechGroup, Inc., Logan, UT (US)

(72) Inventors: Yevgeniy S. Belousov, Mill Creek, WA (US); Eugeny A. Lukhtanov, Bothell, WA (US); Noah Scarr, Seattle, WA (US)

(73) Assignee: ELITECHGROUP, INC., Logan, UT (US)

(*) Notice: Subject to any disclaimer, the term of this patent is extended or adjusted under 35 U.S.C. 154(b) by 0 days.

(21) Appl. No.: 16/660,961

(22) Filed: Oct. 23, 2019

(65) Prior Publication Data

US 2020/0040387 A1 Feb. 6, 2020

Related U.S. Application Data

(63) Continuation-in-part of application No. 15/849,089, filed on Dec. 20, 2017, now Pat. No. 10,590,474, which is a continuation-in-part of application No. 14/202,637, filed on Mar. 10, 2014, now abandoned.

(60) Provisional application No. 61/776,256, filed on Mar. 11, 2013.

(51) Int. Cl.
*C12Q 1/68* (2018.01)
*C12Q 1/6853* (2018.01)
*C12Q 1/6876* (2018.01)
*G01N 21/76* (2006.01)

(52) U.S. Cl.
CPC ......... *C12Q 1/6853* (2013.01); *C12Q 1/6876* (2013.01); *C12Y 301/21002* (2013.01); *G01N 21/76* (2013.01); *C12Q 2600/158* (2013.01)

(58) Field of Classification Search
None
See application file for complete search history.

(56) References Cited

U.S. PATENT DOCUMENTS

| 4,943,522 A | 7/1990 | Eisinger et al. |
| 5,270,184 A | 12/1993 | Walker et al. |
| 5,422,252 A | 6/1995 | Walker et al. |
| 5,455,166 A | 10/1995 | Walker |

(Continued)

FOREIGN PATENT DOCUMENTS

| CN | 103014148 | 4/2013 |
| WO | 01/38584 | 5/2001 |

(Continued)

OTHER PUBLICATIONS

International Search Report and Written Opinion of the International Search Authority—The European Patent Office—dated Jul. 8, 2020 for PCT/US19/65210, 15 pages.

(Continued)

*Primary Examiner* — Aaron A Priest
(74) *Attorney, Agent, or Firm* — Jackson Walker LLP

(57) ABSTRACT

Methods, primers and probes are provided for the isothermal amplification and detection, without denaturation, of double stranded nucleic acid targets for polymerase strand displacement amplification ("iSDA"). The methods and compositions disclosed are highly specific for nucleic acid targets with high sensitivity, specificity and speed that allow detection of clinical relevant target levels. The methods and compositions can easily be used to amplify or detect nucleic acid targets in biological samples.

14 Claims, 39 Drawing Sheets

Specification includes a Sequence Listing.

(56) References Cited

U.S. PATENT DOCUMENTS

| | | | |
|---|---|---|---|
| 5,470,723 | A | 11/1995 | Walker et al. |
| 5,561,944 | A | 10/1996 | Ismail et al. |
| 5,624,825 | A | 4/1997 | Walker et al. |
| 5,712,124 | A | 1/1998 | Walker |
| 5,736,365 | A | 4/1998 | Walker et al. |
| 5,824,796 | A | 10/1998 | Petrie et al. |
| 5,912,340 | A | 6/1999 | Kutyavin et al. |
| 6,127,121 | A | 10/2000 | Meyer, Jr. et al. |
| 6,440,706 | B1 | 8/2002 | Vogelstein et al. |
| 6,660,845 | B1 | 12/2003 | Gall et al. |
| 6,683,173 | B2 | 1/2004 | Dempcy et al. |
| 6,790,945 | B2 | 9/2004 | Lukhtanov et al. |
| 7,045,610 | B2 | 5/2006 | Dempcy et al. |
| 7,252,940 | B2 | 8/2007 | Kutyavin et al. |
| RE39,885 | E | 10/2007 | Nadeau et al. |
| 7,282,328 | B2 | 10/2007 | Kong et al. |
| 7,381,818 | B2 | 6/2008 | Lokhov et al. |
| 7,488,578 | B2 | 2/2009 | Gumbrecht et al. |
| 7,751,982 | B2 | 7/2010 | Dempcy et al. |
| 7,799,554 | B2 | 9/2010 | Mazumdar et al. |
| 8,202,972 | B2 | 6/2012 | Nelson et al. |
| 9,328,384 | B2 | 5/2016 | Belousov |
| 2007/0054301 | A1* | 3/2007 | Becker .................. C12Q 1/6853 435/6.12 |
| 2009/0092967 | A1* | 4/2009 | Yao ...................... C12Q 1/6844 435/6.12 |
| 2009/0111100 | A1 | 4/2009 | Lukhtanov et al. |
| 2010/0057862 | A1 | 3/2010 | Nicol, II et al. |
| 2011/0151457 | A1 | 6/2011 | Belousov et al. |
| 2011/0171649 | A1 | 7/2011 | Kutyavin |
| 2012/0015358 | A1 | 1/2012 | Scarr et al. |
| 2012/0156728 | A1* | 6/2012 | Li ........................ C12Q 1/6874 435/91.1 |
| 2012/0244535 | A1 | 9/2012 | Vorobiev et al. |
| 2014/0255928 | A1 | 9/2014 | Belousov et al. |
| 2018/0127815 | A1 | 5/2018 | Belousov et al. |

FOREIGN PATENT DOCUMENTS

| | | | |
|---|---|---|---|
| WO | 01/64958 | 9/2001 | |
| WO | WO-2012022755 A1 * | 2/2012 | .......... C12Q 1/6844 |

OTHER PUBLICATIONS

Wang, et al., "An Isothermal strand displacement amplification strategy for nucleic acids using junction forming probes and colorimetric detection", Michrochim Acta (2017), 184: pp. 1603-1610.

Toley, et al., "Isothermal strand displacement amplification (iSDA): a rapid and sensitive method of nucleic acid amplification for point-of-care diagnosis", The Royal Society of Chemistry—Analyst, (2015) 140; pp. 7540-7549.

* cited by examiner

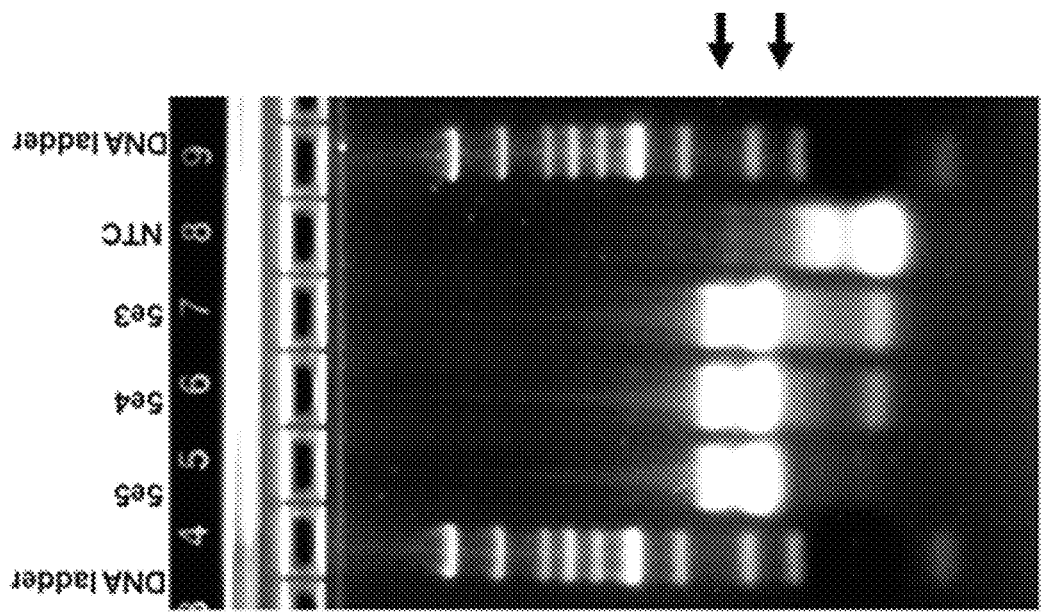
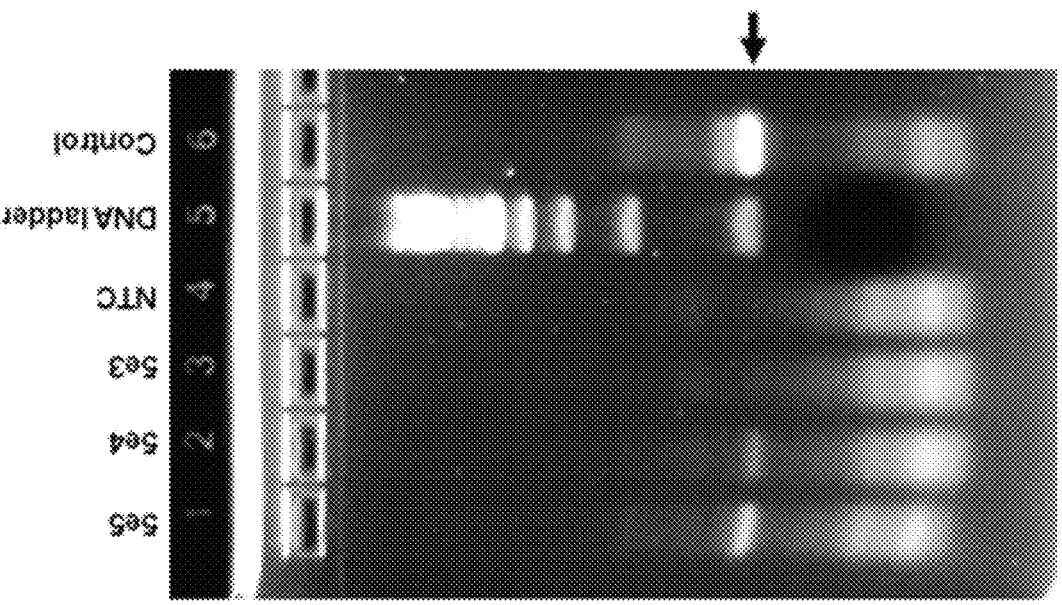
FIG. 11

FIG. 13
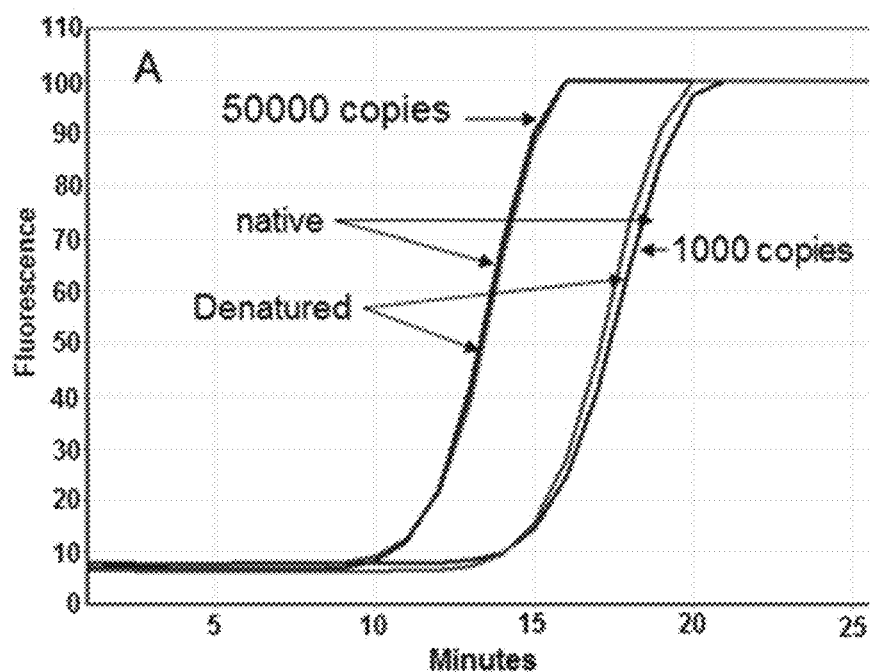
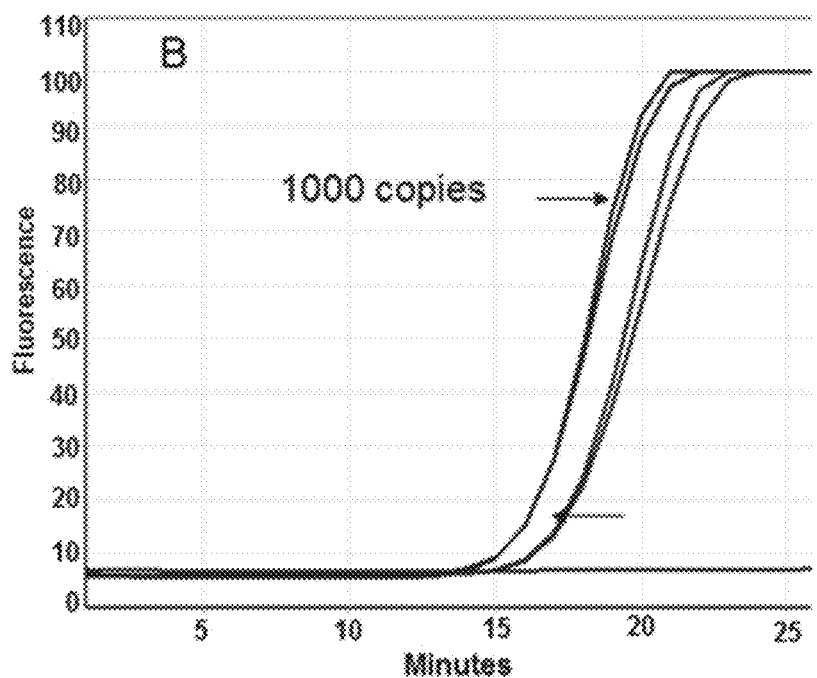

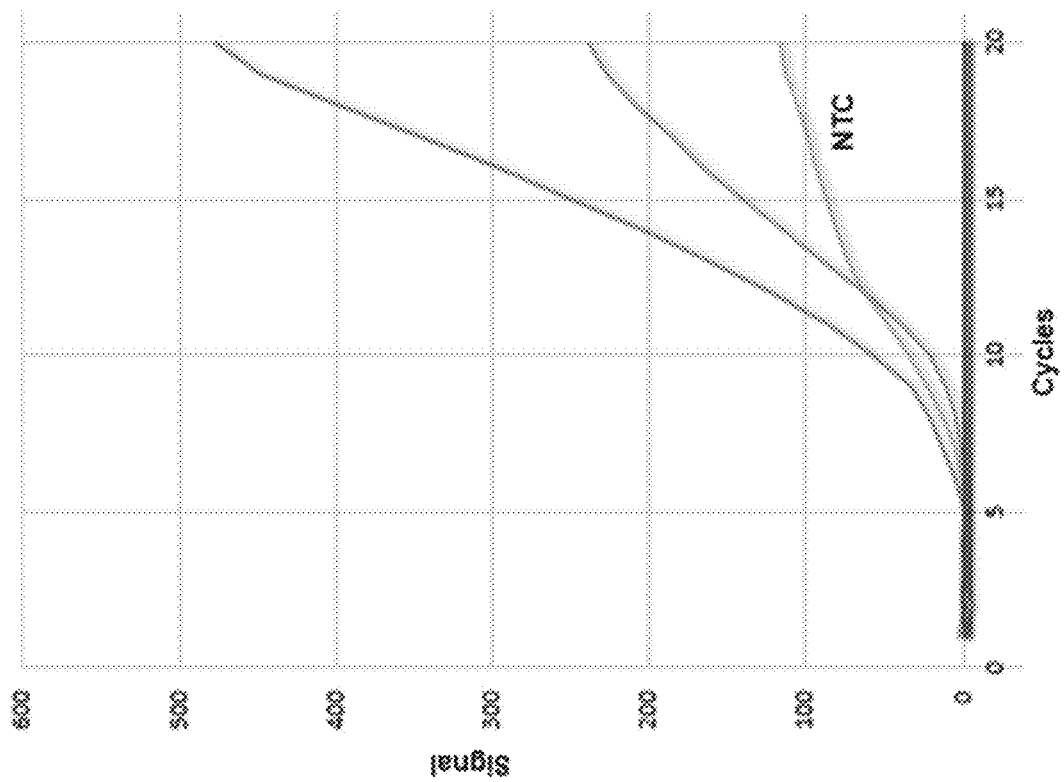
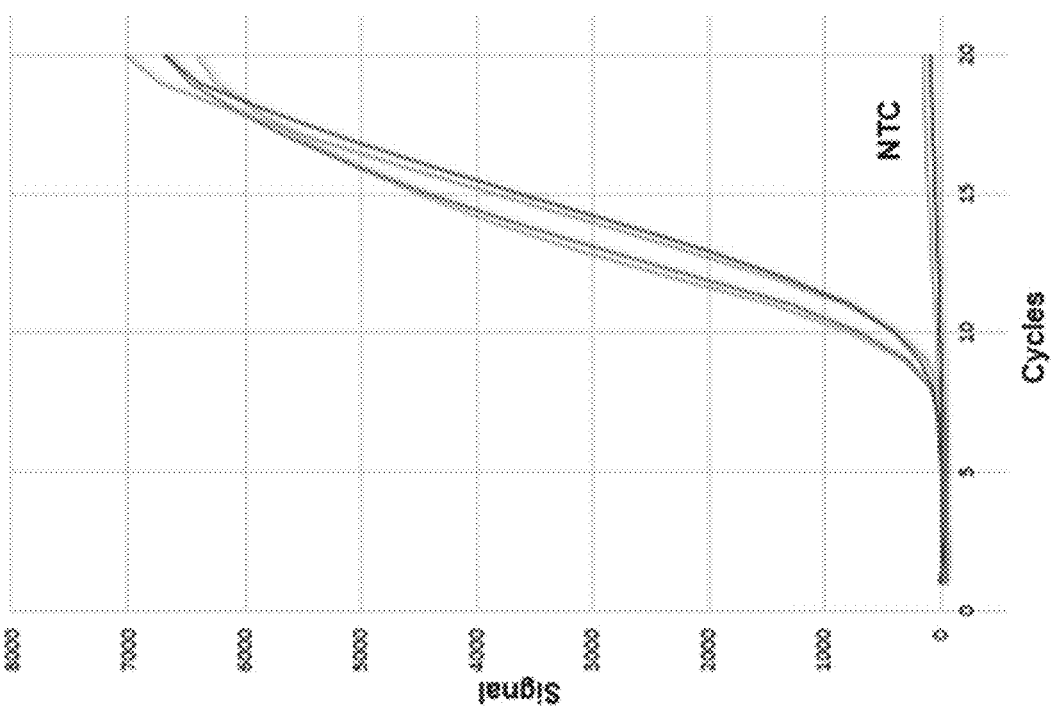

Fluorescein-labeled uridine

Eclipse Dark Quencher

SEQUENCE LISTING

<160> NUMBER OF SEQ ID NOS: 87

<210> SEQ ID NO 1
<211> LENGTH: 45
<212> TYPE: DNA
<213> ORGANISM: Artificial Sequence

```
<220> FEATURE:
<223> OTHER INFORMATION: Forward primer

<400> SEQUENCE: 1
gcataatact accagtctcc tcagcaagct acgcattttc attag                      45

<210> SEQ ID NO 2
<211> LENGTH: 44
<212> TYPE: DNA
<213> ORGANISM: Artificial Sequence
<220> FEATURE:
<223> OTHER INFORMATION: Reverse primer

<400> SEQUENCE: 2
tagaatagtc gcatacttcc tcagccataa catctcctcg aact                       44

<210> SEQ ID NO 3
<211> LENGTH: 18
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: n is C conjugated to fluorescein and minor
      groove binder
<220> FEATURE:
<221> NAME/KEY: misc_feature
<222> LOCATION: (18)..(18)
<223> OTHER INFORMATION: n is C conjugated to Eclipse dark quencher

<400> SEQUENCE: 3
ntaattcatc aacaatgn                                                    18

<210> SEQ ID NO 4
<211> LENGTH: 19
<212> TYPE: DNA
<213> ORGANISM: Artificial Sequence
<220> FEATURE:
<223> OTHER INFORMATION: Forward bumper

<400> SEQUENCE: 4
aggtaatggt gcagtaggt                                                   19

<210> SEQ ID NO 5
<211> LENGTH: 17
<212> TYPE: DNA
<213> ORGANISM: Artificial Sequence
<220> FEATURE:
<223> OTHER INFORMATION: Reverse bumper

<400> SEQUENCE: 5
ccagctttca cacgaac                                                     17

<210> SEQ ID NO 6
<211> LENGTH: 20
<212> TYPE: DNA
<213> ORGANISM: Artificial Sequence
<220> FEATURE:
<223> OTHER INFORMATION: pDNA capture probe
<220> FEATURE:
<221> NAME/KEY: misc_feature
<222> LOCATION: (1)..(1)
<223> OTHER INFORMATION: n is C conjugated to hexaethylene glycol linker
      and CTTTTTTTT

<400> SEQUENCE: 6
```
nagtgtctaa atcaatgatg                                          20

<210> SEQ ID NO 7
<211> LENGTH: 18
<212> TYPE: DNA
<213> ORGANISM: Artificial Sequence
<220> FEATURE:
<223> OTHER INFORMATION: Biotinilated detection probe
<220> FEATURE:
<221> NAME/KEY: misc_feature
<222> LOCATION: (18)..(18)
<223> OTHER INFORMATION: n is C conjugated to biotin

<400> SEQUENCE: 7
ctaattcatc aacaatgn                                            18

<210> SEQ ID NO 8
<211> LENGTH: 44
<212> TYPE: DNA
<213> ORGANISM: Artificial Sequence
<220> FEATURE:
<223> OTHER INFORMATION: Design 1 forward primer

<400> SEQUENCE: 8
gaaacaatgt acctgtcacc tcagcgaccg aaacaatgtg gaat               44

<210> SEQ ID NO 9
<211> LENGTH: 44
<212> TYPE: DNA
<213> ORGANISM: Artificial Sequence
<220> FEATURE:
<223> OTHER INFORMATION: Design 1 reverse primer

<400> SEQUENCE: 9
ttcaatagtc agttacttcc tcagcggaac gatgcctaat ctca               44

<210> SEQ ID NO 10
<211> LENGTH: 17
<212> TYPE: DNA
<213> ORGANISM: Artificial Sequence
<220> FEATURE:
<223> OTHER INFORMATION: Design 1 probe
<220> FEATURE:
<221> NAME/KEY: misc_feature
<222> LOCATION: (1)..(1)
<223> OTHER INFORMATION: n is C conjugated to fluorescein and minor
      groove binder
<220> FEATURE:
<221> NAME/KEY: misc_feature
<222> LOCATION: (17)..(17)
<223> OTHER INFORMATION: n is T conjugated to Eclipse dark quencher

<400> SEQUENCE: 10
ncaatacagg aacacan                                             17

<210> SEQ ID NO 11
<211> LENGTH: 23
<212> TYPE: DNA
<213> ORGANISM: Artificial Sequence
<220> FEATURE:
<223> OTHER INFORMATION: Design 1 forward bumper

<400> SEQUENCE: 11
gaaaatttaa aatcagaacg tgg                                      23

<210> SEQ ID NO 12
<211> LENGTH: 23
<212> TYPE: DNA

```
<213> ORGANISM: Artificial Sequence
<220> FEATURE:
<223> OTHER INFORMATION: Design 1 reverse bumper
<220> FEATURE:
<221> NAME/KEY: misc_feature
<222> LOCATION: (6)..(6)
<223> OTHER INFORMATION: n is Super A

<400> SEQUENCE: 12
gctttntaat cttttttaga tac                                              23

<210> SEQ ID NO 13
<211> LENGTH: 14
<212> TYPE: DNA
<213> ORGANISM: Artificial Sequence
<220> FEATURE:
<223> OTHER INFORMATION: Design 1 pDNA capture probe
<220> FEATURE:
<221> NAME/KEY: misc_feature
<222> LOCATION: (1)..(1)
<223> OTHER INFORMATION: n is C conjugated to hexaethylene glycol linker
      and CTTTTTTTT
<220> FEATURE:
<221> NAME/KEY: misc_feature
<222> LOCATION: (9)..(9)
<223> OTHER INFORMATION: n is Super A

<400> SEQUENCE: 13
naatgtggna ttgg                                                        14

<210> SEQ ID NO 14
<211> LENGTH: 17
<212> TYPE: DNA
<213> ORGANISM: Artificial Sequence
<220> FEATURE:
<223> OTHER INFORMATION: Design 1 biotinilated detection probe
<220> FEATURE:
<221> NAME/KEY: misc_feature
<222> LOCATION: (17)..(17)
<223> OTHER INFORMATION: n is T conjugated to biotin

<400> SEQUENCE: 14
ccaatacagg aacacan                                                     17

<210> SEQ ID NO 15
<211> LENGTH: 45
<212> TYPE: DNA
<213> ORGANISM: Artificial Sequence
<220> FEATURE:
<223> OTHER INFORMATION: Design 2 forward primer

<400> SEQUENCE: 15
ccattatact acctgtctcc tcagcggcaa agatattcaa ctaac                      45

<210> SEQ ID NO 16
<211> LENGTH: 47
<212> TYPE: DNA
<213> ORGANISM: Artificial Sequence
<220> FEATURE:
<223> OTHER INFORMATION: Design 2 reverse primer

<400> SEQUENCE: 16
tagaatagtc agttacttcc tcagcgccat aatcattttt catgttg                    47

<210> SEQ ID NO 17
<211> LENGTH: 18
<212> TYPE: DNA
<213> ORGANISM: Artificial Sequence
<220> FEATURE:
```

```
<223> OTHER INFORMATION: Design 2 probe
<220> FEATURE:
<221> NAME/KEY: misc_feature
<222> LOCATION: (1)..(1)
<223> OTHER INFORMATION: n is C conjugated to fluorescein and minor
      groove binder
<220> FEATURE:
<221> NAME/KEY: misc_feature
<222> LOCATION: (18)..(18)
<223> OTHER INFORMATION: n is C conjugated to Eclipse dark quencher

<400> SEQUENCE: 17
nttttgaact ttagcatn                                                   18

<210> SEQ ID NO 18
<211> LENGTH: 23
<212> TYPE: DNA
<213> ORGANISM: Artificial Sequence
<220> FEATURE:
<223> OTHER INFORMATION: Design 2 forward bumper

<400> SEQUENCE: 18
gataatagca atacaatcgc aca                                             23

<210> SEQ ID NO 19
<211> LENGTH: 23
<212> TYPE: DNA
<213> ORGANISM: Artificial Sequence
<220> FEATURE:
<223> OTHER INFORMATION: Design 2 reverse bumper

<400> SEQUENCE: 19
gtgctaataa ttcacctgtt tga                                             23

<210> SEQ ID NO 20
<211> LENGTH: 19
<212> TYPE: DNA
<213> ORGANISM: Artificial Sequence
<220> FEATURE:
<223> OTHER INFORMATION: Design 2 pDNA capture probe
<220> FEATURE:
<221> NAME/KEY: misc_feature
<222> LOCATION: (1)..(1)
<223> OTHER INFORMATION: n is C conjugated to hexaethylene glycol linker
      and CTAAGAAC

<400> SEQUENCE: 20
ntttagcatc aatagttag                                                  19

<210> SEQ ID NO 21
<211> LENGTH: 19
<212> TYPE: DNA
<213> ORGANISM: Artificial Sequence
<220> FEATURE:
<223> OTHER INFORMATION: Design 2 biotinilated detection probe
<220> FEATURE:
<221> NAME/KEY: misc_feature
<222> LOCATION: (4)..(4)
<223> OTHER INFORMATION: n is Super A
<220> FEATURE:
<221> NAME/KEY: misc_feature
<222> LOCATION: (10)..(10)
<223> OTHER INFORMATION: n is Super A
<220> FEATURE:
<221> NAME/KEY: misc_feature
<222> LOCATION: (19)..(19)
<223> OTHER INFORMATION: n is A conjugated to biotin

<400> SEQUENCE: 21
gttntaaatn ctcttttgn                                                  19
```

<210> SEQ ID NO 22
<211> LENGTH: 40
<212> TYPE: DNA
<213> ORGANISM: Artificial Sequence
<220> FEATURE:
<223> OTHER INFORMATION: Design 3 limiting primer L1

<400> SEQUENCE: 22
aataaatcat aaggatcaac gtgttatagg ttctggtaca                    40

<210> SEQ ID NO 23
<211> LENGTH: 36
<212> TYPE: DNA
<213> ORGANISM: Artificial Sequence
<220> FEATURE:
<223> OTHER INFORMATION: Design 3 excess primer E1

<400> SEQUENCE: 23
aataaatcat aaggatctga gcatcgacgc tacgtg                        36

<210> SEQ ID NO 24
<211> LENGTH: 16
<212> TYPE: DNA
<213> ORGANISM: Artificial Sequence
<220> FEATURE:
<223> OTHER INFORMATION: Design 3 forward bumper 1

<400> SEQUENCE: 24
atggaaattc tctggt                                              16

<210> SEQ ID NO 25
<211> LENGTH: 15
<212> TYPE: DNA
<213> ORGANISM: Artificial Sequence
<220> FEATURE:
<223> OTHER INFORMATION: Design 3 reverse bumper 1

<400> SEQUENCE: 25
tgtcaccatg ttcac                                               15

<210> SEQ ID NO 26
<211> LENGTH: 40
<212> TYPE: DNA
<213> ORGANISM: Artificial Sequence
<220> FEATURE:
<223> OTHER INFORMATION: Design 4 limiting primer L2

<400> SEQUENCE: 26
aataaatcat aaggatctgg tgaacatggt gacactgaat                    40

<210> SEQ ID NO 27
<211> LENGTH: 38
<212> TYPE: DNA
<213> ORGANISM: Artificial Sequence
<220> FEATURE:
<223> OTHER INFORMATION: Design 4 excess primer E2

<400> SEQUENCE: 27
aataaatcat aaggatcgcc ctcaggacgt tgttcaag                      38

<210> SEQ ID NO 28
<211> LENGTH: 14
<212> TYPE: DNA
<213> ORGANISM: Artificial Sequence
<220> FEATURE:

<223> OTHER INFORMATION: Design 4 forward bumper 2

<400> SEQUENCE: 28
agcgtcgatg ctca                                                           14

<210> SEQ ID NO 29
<211> LENGTH: 17
<212> TYPE: DNA
<213> ORGANISM: Artificial Sequence
<220> FEATURE:
<223> OTHER INFORMATION: Design 4 reverse bumper 2

<400> SEQUENCE: 29
aatttgttca atttgcg                                                        17

<210> SEQ ID NO 30
<211> LENGTH: 42
<212> TYPE: DNA
<213> ORGANISM: Artificial Sequence
<220> FEATURE:
<223> OTHER INFORMATION: Table 4 limiting primer L1

<400> SEQUENCE: 30
ccaatatagt aacagtctcc tcagcattcg cccttctgca cg                            42

<210> SEQ ID NO 31
<211> LENGTH: 44
<212> TYPE: DNA
<213> ORGANISM: Artificial Sequence
<220> FEATURE:
<223> OTHER INFORMATION: Table 4 excess primer E1

<400> SEQUENCE: 31
ttcaaaagac ccatacttcc tcagccttct cattttttct accg                          44

<210> SEQ ID NO 32
<211> LENGTH: 17
<212> TYPE: DNA
<213> ORGANISM: Artificial Sequence
<220> FEATURE:
<223> OTHER INFORMATION: Table 4 forward bumper 1

<400> SEQUENCE: 32
tcggatccac tagtaac                                                        17

<210> SEQ ID NO 33
<211> LENGTH: 20
<212> TYPE: DNA
<213> ORGANISM: Artificial Sequence
<220> FEATURE:
<223> OTHER INFORMATION: Table 4 reverse bumper 1

<400> SEQUENCE: 33
gtgatggata tctgcagaat                                                     20

<210> SEQ ID NO 34
<211> LENGTH: 16
<212> TYPE: DNA
<213> ORGANISM: Artificial Sequence
<220> FEATURE:
<223> OTHER INFORMATION: Table 4 chimeric pDNA/DNA
<220> FEATURE:
<221> NAME/KEY: misc_feature
<222> LOCATION: (1)..(1)
<223> OTHER INFORMATION: n is G conjugated to hexaethylene glycol linker
      and ACACTACA

```
<400> SEQUENCE: 34
natcttgtac caatgc                                                    16

<210> SEQ ID NO 35
<211> LENGTH: 14
<212> TYPE: DNA
<213> ORGANISM: Artificial Sequence
<220> FEATURE:
<223> OTHER INFORMATION: Table 4 biotinilated probe
<220> FEATURE:
<221> NAME/KEY: misc_feature
<222> LOCATION: (14)..(14)
<223> OTHER INFORMATION: n is G conjugated to biotin TEG

<400> SEQUENCE: 35
cgtggtccgt aaan                                                      14

<210> SEQ ID NO 36
<211> LENGTH: 240
<212> TYPE: DNA
<213> ORGANISM: Artificial Sequence
<220> FEATURE:
<223> OTHER INFORMATION: Table 4 IC2

<400> SEQUENCE: 36
tttcacacag gaaacagcta tgaccatgat tacgccaagc tatttaggtg acactataga      60
atactcaagc tatgcatcaa gcttggtacc gagctcggat ccactagtaa cggccgccag     120
tgtgctggaa ttcgcccttc tgcacggacc agttacttta cggaccacgt accgcattgg    180
tacaagatct ccggtagaaa aaatgagaag ggcgaattct gcagatatcc atcacactgg    240

<210> SEQ ID NO 37
<211> LENGTH: 48
<212> TYPE: DNA
<213> ORGANISM: Artificial Sequence
<220> FEATURE:
<223> OTHER INFORMATION: Table 5 limiting primer L1

<400> SEQUENCE: 37
gcattatagt acctgtctcc tcagctggtg aacatggtga cactgaat                 48

<210> SEQ ID NO 38
<211> LENGTH: 46
<212> TYPE: DNA
<213> ORGANISM: Artificial Sequence
<220> FEATURE:
<223> OTHER INFORMATION: Table 5 excess primer E1

<400> SEQUENCE: 38
ttgaatagtc ggttacttcc tcagcgccct caggacgttg ttcaag                   46

<210> SEQ ID NO 39
<211> LENGTH: 14
<212> TYPE: DNA
<213> ORGANISM: Artificial Sequence
<220> FEATURE:
<223> OTHER INFORMATION: Table 5 forward bumper 1

<400> SEQUENCE: 39
agcgtcgatg ctca                                                      14

<210> SEQ ID NO 40
<211> LENGTH: 17
<212> TYPE: DNA
<213> ORGANISM: Artificial Sequence
```

```
<220> FEATURE:
<223> OTHER INFORMATION: Table 5 reverse bumper 1

<400> SEQUENCE: 40
aatttgttca atttgcg                                                    17

<210> SEQ ID NO 41
<211> LENGTH: 44
<212> TYPE: DNA
<213> ORGANISM: Artificial Sequence
<220> FEATURE:
<223> OTHER INFORMATION: Table 6 limiting primer L1

<400> SEQUENCE: 41
gcattatagt acctgtctcc tcagcgaatt ccctgcatca atac                       44

<210> SEQ ID NO 42
<211> LENGTH: 43
<212> TYPE: DNA
<213> ORGANISM: Artificial Sequence
<220> FEATURE:
<223> OTHER INFORMATION: Table 6 excess primer E1
<220> FEATURE:
<221> NAME/KEY: misc_feature
<222> LOCATION: (27)..(27)
<223> OTHER INFORMATION: n is Super A
<220> FEATURE:
<221> NAME/KEY: misc_feature
<222> LOCATION: (32)..(32)
<223> OTHER INFORMATION: n is Super A
<220> FEATURE:
<221> NAME/KEY: misc_feature
<222> LOCATION: (38)..(39)
<223> OTHER INFORMATION: n is Super T

<400> SEQUENCE: 42
gcattatggt acctctctcc tcagctntgt cnatatcnnc atc                        43

<210> SEQ ID NO 43
<211> LENGTH: 21
<212> TYPE: DNA
<213> ORGANISM: Artificial Sequence
<220> FEATURE:
<223> OTHER INFORMATION: Table 6 forward bumper 1

<400> SEQUENCE: 43
aactaaggcc aaagcttata c                                               21

<210> SEQ ID NO 44
<211> LENGTH: 19
<212> TYPE: DNA
<213> ORGANISM: Artificial Sequence
<220> FEATURE:
<223> OTHER INFORMATION: Table 6 reverse bumper 1

<400> SEQUENCE: 44
cagtcagtag tagaccatg                                                  19

<210> SEQ ID NO 45
<211> LENGTH: 19
<212> TYPE: DNA
<213> ORGANISM: Artificial Sequence
<220> FEATURE:
<223> OTHER INFORMATION: Table 6 chimeric pDNA/DNA
<220> FEATURE:
<221> NAME/KEY: misc_feature
<222> LOCATION: (1)..(1)
<223> OTHER INFORMATION: n is C conjugated to hexaethylene glycol linker
      and CTTTTTTTT
```

<400> SEQUENCE: 45
ntacaaatta tcactttga                                          19

<210> SEQ ID NO 46
<211> LENGTH: 17
<212> TYPE: DNA
<213> ORGANISM: Artificial Sequence
<220> FEATURE:
<223> OTHER INFORMATION: Table 6 biotinilated probe
<220> FEATURE:
<221> NAME/KEY: misc_feature
<222> LOCATION: (2)..(2)
<223> OTHER INFORMATION: n is Super A
<220> FEATURE:
<221> NAME/KEY: misc_feature
<222> LOCATION: (17)..(17)
<223> OTHER INFORMATION: n is G conjugated to biotin TEG

<400> SEQUENCE: 46
tnatcgcata ttaacan                                            17

<210> SEQ ID NO 47
<211> LENGTH: 17
<212> TYPE: DNA
<213> ORGANISM: Artificial Sequence
<220> FEATURE:
<223> OTHER INFORMATION: Table 6 FAM probe
<220> FEATURE:
<221> NAME/KEY: misc_feature
<222> LOCATION: (1)..(1)
<223> OTHER INFORMATION: n is T conjugated to fluorescein and minor
      groove binder
<220> FEATURE:
<221> NAME/KEY: misc_feature
<222> LOCATION: (11)..(12)
<223> OTHER INFORMATION: n is Super T
<220> FEATURE:
<221> NAME/KEY: misc_feature
<222> LOCATION: (17)..(17)
<223> OTHER INFORMATION: n is G conjugated to Eclipse dark quencher

<400> SEQUENCE: 47
naatcgcata nnaacan                                            17

<210> SEQ ID NO 48
<211> LENGTH: 48
<212> TYPE: DNA
<213> ORGANISM: Artificial Sequence
<220> FEATURE:
<223> OTHER INFORMATION: Table 7 limiting primer L1

<400> SEQUENCE: 48
gaatagaccc atacatcctc agcgacttga gtaatgataa attgatag           48

<210> SEQ ID NO 49
<211> LENGTH: 48
<212> TYPE: DNA
<213> ORGANISM: Artificial Sequence
<220> FEATURE:
<223> OTHER INFORMATION: Table 7 excess primer E1

<400> SEQUENCE: 49
gaatagaccc atacatcctc agcgacttga gtaatgataa attgatag           48

<210> SEQ ID NO 50
<211> LENGTH: 21
<212> TYPE: DNA
<213> ORGANISM: Artificial Sequence

```
<220> FEATURE:
<223> OTHER INFORMATION: Table 7 forward bumper 1
<220> FEATURE:
<221> NAME/KEY: misc_feature
<222> LOCATION: (3)..(3)
<223> OTHER INFORMATION: n is Super A

<400> SEQUENCE: 50
ccncttgctt ataactgtat g                                               21

<210> SEQ ID NO 51
<211> LENGTH: 20
<212> TYPE: DNA
<213> ORGANISM: Artificial Sequence
<220> FEATURE:
<223> OTHER INFORMATION: Table 7 reverse bumper 1
<220> FEATURE:
<221> NAME/KEY: misc_feature
<222> LOCATION: (7)..(7)
<223> OTHER INFORMATION: n is Super A

<400> SEQUENCE: 51
gtttccntag aaaccttcat                                                 20

<210> SEQ ID NO 52
<211> LENGTH: 17
<212> TYPE: DNA
<213> ORGANISM: Artificial Sequence
<220> FEATURE:
<223> OTHER INFORMATION: Table 7 FAM probe
<220> FEATURE:
<221> NAME/KEY: misc_feature
<222> LOCATION: (1)..(1)
<223> OTHER INFORMATION: n is A conjugated to fluorescein and minor
      groove binder
<220> FEATURE:
<221> NAME/KEY: misc_feature
<222> LOCATION: (17)..(17)
<223> OTHER INFORMATION: n is C conjugated to Eclipse dark quencher

<400> SEQUENCE: 52
nttgattccg ttttgan                                                    17

<210> SEQ ID NO 53
<211> LENGTH: 43
<212> TYPE: DNA
<213> ORGANISM: Artificial Sequence
<220> FEATURE:
<223> OTHER INFORMATION: Table 9 primer CMV1 L11

<400> SEQUENCE: 53
gcaatataga accagtatcc tcagcgtaga ggaggataac aac                       43

<210> SEQ ID NO 54
<211> LENGTH: 43
<212> TYPE: DNA
<213> ORGANISM: Artificial Sequence
<220> FEATURE:
<223> OTHER INFORMATION: Table 9 primer CMV1 L3

<400> SEQUENCE: 54
gcaatataga accagtatcc tcagcaggag gataacaaca cat                       43

<210> SEQ ID NO 55
<211> LENGTH: 45
<212> TYPE: DNA
<213> ORGANISM: Artificial Sequence
<220> FEATURE:
<223> OTHER INFORMATION: Table 9 primer CMV1 L4
```

<400> SEQUENCE: 55
gcaatataga accagtatcc tcagcggagg ataacaacac atata                45

<210> SEQ ID NO 56
<211> LENGTH: 46
<212> TYPE: DNA
<213> ORGANISM: Artificial Sequence
<220> FEATURE:
<223> OTHER INFORMATION: Table 9 primer CMV1 L5
<220> FEATURE:
<221> NAME/KEY: misc_feature
<222> LOCATION: (41)..(41)
<223> OTHER INFORMATION: n is Super T

<400> SEQUENCE: 56
gcaatataga accagtatcc tcagcgagga taacaacaca nataag              46

<210> SEQ ID NO 57
<211> LENGTH: 46
<212> TYPE: DNA
<213> ORGANISM: Artificial Sequence
<220> FEATURE:
<223> OTHER INFORMATION: Table 9 primer CMV1 L2
<220> FEATURE:
<221> NAME/KEY: misc_feature
<222> LOCATION: (35)..(35)
<223> OTHER INFORMATION: n is Super A
<220> FEATURE:
<221> NAME/KEY: misc_feature
<222> LOCATION: (40)..(40)
<223> OTHER INFORMATION: n is Super T

<400> SEQUENCE: 57
gcaatataga accagtatcc tcagcgataa caacncatan aagtat              46

<210> SEQ ID NO 58
<211> LENGTH: 44
<212> TYPE: DNA
<213> ORGANISM: Artificial Sequence
<220> FEATURE:
<223> OTHER INFORMATION: Table 9 primer CMV L9
<220> FEATURE:
<221> NAME/KEY: misc_feature
<222> LOCATION: (32)..(32)
<223> OTHER INFORMATION: n is Super T
<220> FEATURE:
<221> NAME/KEY: misc_feature
<222> LOCATION: (38)..(38)
<223> OTHER INFORMATION: n is Super T

<400> SEQUENCE: 58
gcaatataga accagtatcc tcagcaacac anataagnat ccgt                44

<210> SEQ ID NO 59
<211> LENGTH: 43
<212> TYPE: DNA
<213> ORGANISM: Artificial Sequence
<220> FEATURE:
<223> OTHER INFORMATION: Table 9 primer CMV1 L6

<400> SEQUENCE: 59
gcaatataga accagtatcc tcagcacata taagtatccg tcc                 43

<210> SEQ ID NO 60
<211> LENGTH: 44
<212> TYPE: DNA
<213> ORGANISM: Artificial Sequence
<220> FEATURE:

<223> OTHER INFORMATION: Table 9 primer CMV1 L8

<400> SEQUENCE: 60
gcaatataga accagtatcc tcagcatata agtatccgtc ctcc        44

<210> SEQ ID NO 61
<211> LENGTH: 43
<212> TYPE: DNA
<213> ORGANISM: Artificial Sequence
<220> FEATURE:
<223> OTHER INFORMATION: Table 9 primer CMV1 L10

<400> SEQUENCE: 61
gcaatataga accagtatcc tcagcaagta tccgtcctcc tga        43

<210> SEQ ID NO 62
<211> LENGTH: 44
<212> TYPE: DNA
<213> ORGANISM: Artificial Sequence
<220> FEATURE:
<223> OTHER INFORMATION: Table 9 primer CMV1 E4

<400> SEQUENCE: 62
gcaatataga accagtatcc tcagcgatta actcttgcat gtga        44

<210> SEQ ID NO 63
<211> LENGTH: 46
<212> TYPE: DNA
<213> ORGANISM: Artificial Sequence
<220> FEATURE:
<223> OTHER INFORMATION: Table 9 primer CMV1 E3
<220> FEATURE:
<221> NAME/KEY: misc_feature
<222> LOCATION: (40)..(40)
<223> OTHER INFORMATION: n is Super A

<400> SEQUENCE: 63
gcaatataga accagtatcc tcagcatgtc agatagagtn aagatt        46

<210> SEQ ID NO 64
<211> LENGTH: 46
<212> TYPE: DNA
<213> ORGANISM: Artificial Sequence
<220> FEATURE:
<223> OTHER INFORMATION: Table 9 primer CMV1 E2

<400> SEQUENCE: 64
gcaatataga accagtatcc tcagcttact tgtgtatgtc agatag        46

<210> SEQ ID NO 65
<211> LENGTH: 45
<212> TYPE: DNA
<213> ORGANISM: Artificial Sequence
<220> FEATURE:
<223> OTHER INFORMATION: Table 9 primer CMV1 E1
<220> FEATURE:
<221> NAME/KEY: misc_feature
<222> LOCATION: (33)..(33)
<223> OTHER INFORMATION: n is Super T

<400> SEQUENCE: 65
gcaatataga accagtatcc tcagcgtgta tgncagatag agtaa        45

<210> SEQ ID NO 66
<211> LENGTH: 40
<212> TYPE: DNA
<213> ORGANISM: Artificial Sequence

```
<220> FEATURE:
<223> OTHER INFORMATION: Table 10 primer EV-L1

<400> SEQUENCE: 66
gcaatataga accagtacct cagcgaagag tctattgagc                              40

<210> SEQ ID NO 67
<211> LENGTH: 40
<212> TYPE: DNA
<213> ORGANISM: Artificial Sequence
<220> FEATURE:
<223> OTHER INFORMATION: Table 10 primer EV-E1

<400> SEQUENCE: 67
gcaatataga accagtacct cagctccgca gttaggatta                              40

<210> SEQ ID NO 68
<211> LENGTH: 38
<212> TYPE: DNA
<213> ORGANISM: Artificial Sequence
<220> FEATURE:
<223> OTHER INFORMATION: Table 10 primer ENV-NS-F2

<400> SEQUENCE: 68
gcaatataga accagtacct cagccatccg gtgtgcaa                                38

<210> SEQ ID NO 69
<211> LENGTH: 42
<212> TYPE: DNA
<213> ORGANISM: Artificial Sequence
<220> FEATURE:
<223> OTHER INFORMATION: Table 10 primer ENV-NS-R2

<400> SEQUENCE: 69
gcaatataga accagtacct cagcttgggt tgagacttgt ga                           42

<210> SEQ ID NO 70
<211> LENGTH: 43
<212> TYPE: DNA
<213> ORGANISM: Artificial Sequence
<220> FEATURE:
<223> OTHER INFORMATION: Table 11 limiting primer L1

<400> SEQUENCE: 70
gcaatataga accagtatcc tcagcaatgg ctaaagacaa gac                          43

<210> SEQ ID NO 71
<211> LENGTH: 44
<212> TYPE: DNA
<213> ORGANISM: Artificial Sequence
<220> FEATURE:
<223> OTHER INFORMATION: Table 11 limiting primer L2
<220> FEATURE:
<221> NAME/KEY: misc_feature
<222> LOCATION: (41)..(41)
<223> OTHER INFORMATION: n is Super T

<400> SEQUENCE: 71
gcaatataga accagtatcc tcagcaaggg aattttaggg nttg                         44

<210> SEQ ID NO 72
<211> LENGTH: 41
<212> TYPE: DNA
<213> ORGANISM: Artificial Sequence
<220> FEATURE:
<223> OTHER INFORMATION: Table 11 excess primer E1
<220> FEATURE:
```

<221> NAME/KEY: misc_feature
<222> LOCATION: (33)..(33)
<223> OTHER INFORMATION: n is Super A

<400> SEQUENCE: 72
gcaatataga accagtatcc tcagcatttt ggntaaagcg t                41

<210> SEQ ID NO 73
<211> LENGTH: 20
<212> TYPE: DNA
<213> ORGANISM: Artificial Sequence
<220> FEATURE:
<223> OTHER INFORMATION: Table 11 forward bumper primer

<400> SEQUENCE: 73
cacagatctt gaggctctca                                        20

<210> SEQ ID NO 74
<211> LENGTH: 22
<212> TYPE: DNA
<213> ORGANISM: Artificial Sequence
<220> FEATURE:
<223> OTHER INFORMATION: Table 11 reverse bumper primer

<400> SEQUENCE: 74
cagtttaact gctttgtcca tg                                     22

<210> SEQ ID NO 75
<211> LENGTH: 15
<212> TYPE: DNA
<213> ORGANISM: Artificial Sequence
<220> FEATURE:
<223> OTHER INFORMATION: Table 11 FAM1 probe

<400> SEQUENCE: 75
tcaccgtgcc cagtg                                             15

<210> SEQ ID NO 76
<211> LENGTH: 15
<212> TYPE: DNA
<213> ORGANISM: Artificial Sequence
<220> FEATURE:
<223> OTHER INFORMATION: Table 11 FAM2 probe

<400> SEQUENCE: 76
gactgcagcg tagac                                             15

<210> SEQ ID NO 77
<211> LENGTH: 816
<212> TYPE: DNA
<213> ORGANISM: Coxsackievirus

<400> SEQUENCE: 77
ttaaaacagc ctgtgggttg tacccaccca cagggcccac tgggcgctag cactctgatt 60
ctacggaatc cttgtgcgcc tgttttatgt cccttccccc aatcagtaac ttagaagcat 120
tgcacctctt tcgaccgtta gcaggcgtgg cgcaccagcc atgtcttggt caagcacttc 180
tgtttccccg gaccgagtat caatagactg ctcacgcggt tgagggagaa aacgtccgtt 240
acccggctaa ctacttcgag aagcctagta gcaccatgaa agttgcagag tgtttcgctc 300
agcacttccc ccgtgtagat caggtcgatg agtcactgcg atccccacgg gcgaccgtgg 360
cagtggctgc gttggcggcc tgcctgtggg gtaacccaca ggacgctcta atatggacat 420
ggtgcaaaga gtctattgag ctagttagta gtcctccggc ccctgaatgc ggctaatcct 480

```
aactgcggag cacataccct cgacccaggg ggcagtgtgt cgtaacgggc aactctgcag    540
cggaaccgac tactttgggt gtccgtgttt cctttattc ttatactggc tgcttatggt    600
gacaattgaa agattgttac catatagcta ttggattggc catccggtgt gcaacagagc    660
tattatttac ctatttgttg ggtatatacc actcacatcc agaaaaaccc tcgacacact    720
agtatacatt ctttacttga attctagaaa atggggtcac aagtctcaac ccaacgatcg    780
ggttcccacg aaaattcgaa ctcagcatca gaagga                             816
```

<210> SEQ ID NO 78
<211> LENGTH: 495
<212> TYPE: DNA
<213> ORGANISM: Echovirus

<400> SEQUENCE: 78

```
atccaccta ccccgttgca acttagaagc taattcagta cgatcgatag gcggctcagt     60
acgccaactg agtcatgatc aagcacttct gttaccccgg actgagtatc aatacgctgc   120
tcacgcggct gaaggagaaa acgttcgtta cccggccaat tacttcgaga aacttagtac   180
caccatgaag gttgcgcagc gtttcgctcc gcacaacccc agtgtagatc aggtcgatga   240
gtcaccgcat tccccacggg cgaccgtggc ggtggctgcg ctggcggcct gcccatgggg   300
tatcccatgg gacgcttcaa tactgacatg gtgtgaagag tctattgagc taattggtag   360
tcctccggcc cctgaatgcg gctaatccta actgcggagc agatacccac atgccagtgg   420
gcggtctgtc gtaacgggca actctgcagc ggaaccgact actttgggtg tccgtgtttc   480
cttttatttc tatac                                                    495
```

<210> SEQ ID NO 79
<211> LENGTH: 37
<212> TYPE: DNA
<213> ORGANISM: Artificial Sequence
<220> FEATURE:
<223> OTHER INFORMATION: Forward primer

<400> SEQUENCE: 79

```
gctagaacca gtatcctcag cgaagagtct attgagc                             37
```

<210> SEQ ID NO 80
<211> LENGTH: 37
<212> TYPE: DNA
<213> ORGANISM: Artificial Sequence
<220> FEATURE:
<223> OTHER INFORMATION: Reverse primer

<400> SEQUENCE: 80

```
gctagaacca gtatcctcag ctccgcagtt aggatta                             37
```

<210> SEQ ID NO 81
<211> LENGTH: 19
<212> TYPE: DNA
<213> ORGANISM: Artificial Sequence
<220> FEATURE:
<223> OTHER INFORMATION: Reverse bumper

<400> SEQUENCE: 81

```
cacccaaagt agtcggttc                                                 19
```

<210> SEQ ID NO 82
<211> LENGTH: 19
<212> TYPE: DNA

```
<213> ORGANISM: Artificial Sequence
<220> FEATURE:
<223> OTHER INFORMATION: Ap probe
<220> FEATURE:
<221> NAME/KEY: misc_feature
<222> LOCATION: (9)..(9)
<223> OTHER INFORMATION: s is abasic spacer

<400> SEQUENCE: 82
cctccggcsc ctgaatgcg                                              19

<210> SEQ ID NO 83
<211> LENGTH: 12
<212> TYPE: DNA
<213> ORGANISM: Artificial Sequence
<220> FEATURE:
<223> OTHER INFORMATION: Endo IV Probe
<220> FEATURE:
<221> NAME/KEY: misc_feature
<222> LOCATION: (2)..(2)
<223> OTHER INFORMATION: n is Super A
<220> FEATURE:
<221> NAME/KEY: misc_feature
<222> LOCATION: (4)..(4)
<223> OTHER INFORMATION: n is Super T

<400> SEQUENCE: 83
tngncctccg gc                                                     12

<210> SEQ ID NO 84
<211> LENGTH: 12
<212> TYPE: DNA
<213> ORGANISM: Artificial Sequence
<220> FEATURE:
<223> OTHER INFORMATION: Endo IV Enhancer

<400> SEQUENCE: 84
cctgaatgcg gc                                                     12

<210> SEQ ID NO 85
<211> LENGTH: 17
<212> TYPE: DNA
<213> ORGANISM: Artificial Sequence
<220> FEATURE:
<223> OTHER INFORMATION: Pleaides Probe

<400> SEQUENCE: 85
tccggcccct gaatgcg                                                17

<210> SEQ ID NO 86
<211> LENGTH: 18
<212> TYPE: DNA
<213> ORGANISM: Artificial Sequence
<220> FEATURE:
<223> OTHER INFORMATION: PCR Forward primer

<400> SEQUENCE: 86
gaagagtcta ttgagcta                                               18

<210> SEQ ID NO 87
<211> LENGTH: 15
<212> TYPE: DNA
<213> ORGANISM: Artificial Sequence
<220> FEATURE:
<223> OTHER INFORMATION: PCR Reverse primer
<220> FEATURE:
<221> NAME/KEY: misc_feature
<222> LOCATION: (3)..(3)
<223> OTHER INFORMATION: n is Super A
```

```
<220> FEATURE:
<221> NAME/KEY: misc_feature
<222> LOCATION: (12)..(12)
<223> OTHER INFORMATION: n is Super A

<400> SEQUENCE: 87
ggnttrgccg cnttc                                                    15
```

METHODS FOR TRUE ISOTHERMAL STRAND DISPLACEMENT AMPLIFICATION

This application is a continuation-in-part of and claims priority to U.S. patent application Ser. No. 15/849,089, filed Dec. 20, 2017, entitled "Methods for True Isothermal Strand Displacement Amplification." which is a continuation-in-part of and claims priority to U.S. patent application Ser. No. 14/202,637, filed Mar. 10, 2014, entitled "Methods for True Isothermal Strand Displacement Amplification," which claims priority to U.S. Provisional Patent Application Ser. No. 61/776,256, filed Mar. 11, 2013, entitled "Methods for True Isothermal Strand Displacement Amplification," the entire contents of all being hereby incorporated by reference.

BACKGROUND

This disclosure pertains to methods for isothermal strand displacement amplification that accomplishes efficient primer extension amplification with target specific primers and does not require pre-denaturation.

Isothermal amplification requires single stranded targets for efficient primer extension. Helicase dependent amplification of nucleic acids also requires helicase enzyme for unwinding double strands to allow amplification with a DNA polymerase (U.S. Pat. No. 7,282,328). Exponential strand displacement amplification ("SDA") as described in U.S. Pat. No. 5,455,166 requires an initial denaturation of the target into single-stranded DNA (ssDNA), generation of hemiphosphorothioate sites which allow single strand nicking by restriction enzymes, and extension by a polymerase lacking 5'-3' exonuclease activity. Raising the temperature of the reaction to approximately 95° C. to render double strands into single strands is required to permit binding of the primers to the target strands. State of the art SDA amplification requires the denaturation of the target at elevated temperature to yield ssDNA for strand displacement isothermal amplification.

The use of a nicking enzyme to cleave one of the strands of a target instead of the generation of hemiphosphorothioate sites in SDA amplification was described in (Ehses et al, J. Biochem. Biophys. Methods. 63:170-86 (2005)). The design of primers to reduce non-predictable byproducts was also described. Denaturation at 95° C. was required by Ehses et al. after the addition of target and before the addition of any enzymes. Nicking enzyme SDA amplification without denaturation of target at 95° C. was reported in U.S. Patent Application Publication No. 2009/0092967. However, a limitation of the latter method is that a limited number of nicking enzymes are available and quite often no natural nicking site is present in a target region of interest. An abasic site endonuclease amplification assay was disclosed in U.S. Patent Application Publication No. 2004/0101893. The use of this assay as a post amplification detection system in combination with other amplification systems was also disclosed. These assays require a denaturation step of dsDNA.

It is known in the art that double stranded (ds) nucleic acid can be denatured in different ways. Heat denaturation is state of the art to separate ds DNA into single strands. Native DNA denatures at about 85° C. (White, Handler and Smith, Principles of Biochemistry $5^{th}$ Edition, McGraw-Hill Kogakush, Ltd. pages 192-197, 1993). Early on, it was established that primer extension in amplification required the binding of a primer to a single strand DNA strand. This was preferably achieved by heating the sample at about 95° C. (M Panaccio and A Lew. PCR based diagnosis in the presence of 8% (v/v) blood. Nucleic Acids Res., 19: 1151 (1991)). It was recently reported that Watson-Crick pairs in naked DNA spontaneously flip into Hoogstein pairs under ordinary conditions, suggesting that DNA breathes (Fran-Kamentskii. Artificial DNA; PNA & XNA, 2:1, 1-3 (2011)).

A few nucleases cut just one strand of DNA thereby introducing a nick into DNA (Besnier and Kong, EMBO Reports. 21: 782-786 (2001)). Most such proteins are involved in DNA repair and other DNA-related metabolism and cannot easily be used to manipulate DNA. They usually recognize long sequences and associate with other proteins to form active complexes that are difficult to manufacture (Higashitani et al., J. Mol. Biol., 237: 388-4000 (1994)). Single strand nicking endonucleases which nick only one strand of the DNA double strands and traditional restriction endonucleases are listed and updated in the REBASE Database (rebase.neb.com; Roberts et al., Nucl. Acids Res., 31: 418-420 (2003)). Engineering of a nicking endonuclease has been described (Xu et al. PNAS 98: 12990-12995 (2001)).

Other methods using isothermal amplification have been disclosed recently (Niemz et al., Trends in Biotechnol., 29:240-250 (2011)). However, these amplification methods also utilize thermal or other denaturation.

SUMMARY

The present invention relates generally to an isothermal assay which utilizes the advantages of target nucleic acid amplification without the requirement for dsDNA denaturation. The present methods enable efficient detection of target nucleic acids with exquisite specific amplification. The present disclosure unexpectedly determined that primers designed according to a particular method allow efficient primer extension amplification of target specific primers without pre-denaturation. Generally, the present disclosure provides methods, primers and probes for the isothermal amplification without denaturation of nucleic acid targets for polymerase primer extension (isothermal strand displacement amplification ("iSDA")) in samples including biological samples (e.g., blood, nasopharyngeal or throat, swab, wound swab, or other tissues). The nucleic acid targets may be double stranded or they may be single stranded, such as RSV virus. RNA targets may be single stranded or double stranded.

The method described herein utilizes primer oligonucleotides that allow primer extension without denaturation of nucleic acid targets. In some examples the primers have modified bases to improve stability or to eliminate primer self-association. In one embodiment modified bases are used to limit primer self-association.

In certain examples the primer comprises a 5'-non-complementary tail wherein said tail further comprises a nicking enzyme specific sequence.

In the methods described herein, the nucleic acids present in a clinical or test sample obtained from a biological sample or tissue suspected of containing a clinical target (microorganisms or tissue, for example) are extracted with methods known in the art. The target nucleic acids are amplified without denaturation and detected. More specifically the target specific primers contain a sequence specific for target and a non-target complementary 5'-tail, wherein the tail contains a sequence specific for a nicking enzyme when hybridized to its complementary sequence. At least one amplification cycle provides a double stranded amplicon containing a nicking site which allows strand displacement in a second amplification cycle. The amplified nucleic acid can be detected by a variety of state of the art methods including fluorescence resonance energy ("FRET"), radiolabels, lateral flow, enzyme labels, and the like.

The methods described herein also include methods for the design of primers allowing amplification of at least one cycle of amplification without denaturation of duplex DNA target.

In certain methods provided herein the methods comprise the detection of iSDA or RT-iSDA amplified targets by lateral flow.

Those skilled in the art will appreciate that the present disclosed amplification method can be performed in combination with other methods. In one embodiment the amplification method described in U.S. Patent Application Publication No. 2009/0092967 can be combined with the method of the present disclosure.

This disclosure provides an isothermal method for specifically detecting a nucleic acid sequence in a biological sample from an individual. The disclosure also provides oligonucleotide primers and probes comprising nucleotide sequences characteristic of specific genomic nucleic acid sequences. The method includes performing isothermal amplification without a denaturation step prior to amplification. The amplification step includes contacting the sample nucleic acid with pairs of primers to produce amplification product(s) if the specific genomic nucleic acid target is present. The preferred primers target a specific region of a specific target gene. Each of the preferred primers has a 5'-oligonucleotide tail non-complementary to the target where said non-complementary tail contains a sequence when hybridized to a complementary sequence contains a nicking enzyme cleavage site. The oligonucleotide probes detect the amplified target directly or indirectly. The preferred oligonucleotide probe is a 5'-minor groove binder-fluorophore-oligonucleotide-quencher-3' conjugate that fluoresces on hybridization to its complementary amplified target. In some embodiments one or more primer is labeled. In some embodiments a double strand binding fluorescent dye is used. In some embodiments one or more bumper oligonucleotides are provided. In some embodiments the probe(s) is omitted. In some embodiments the amplified target is captured on a solid support or membrane and detected by a labeled probe. In some embodiments the primer concentrations are present in different concentrations. In some embodiments an internal control is provided.

BRIEF DESCRIPTION OF THE DRAWINGS

FIG. 11 shows the results of amplification reactions comparing amplification with primers and probes optimized for use in the present isothermal strand displacement amplification method and traditional primers and probes.

FIG. 13 shows the real-time iSDA amplification of native and denatured *Plasmodium falciparum* DNA.

FIG. 19 shows estimated fractions of dissociated bases within a target RSV sequence and placement of primers designed for iSDA amplification.

FIG. 21A shows estimated fractions of dissociated bases within a target enterovirus sequence and placement of primers designed for iSDA amplification.

FIG. 28A shows signal strength in iSDA detection using Pleiades probes with interrogation of high concentration echovirus samples and with non-template control (NTC).

FIG. 28B shows signal strength in iSDA detection using Pleiades probes with lower target echovirus sample concentration and with NTC.

DETAILED DESCRIPTION OF PREFERRED EMBODIMENTS

I. General

Figure 1:
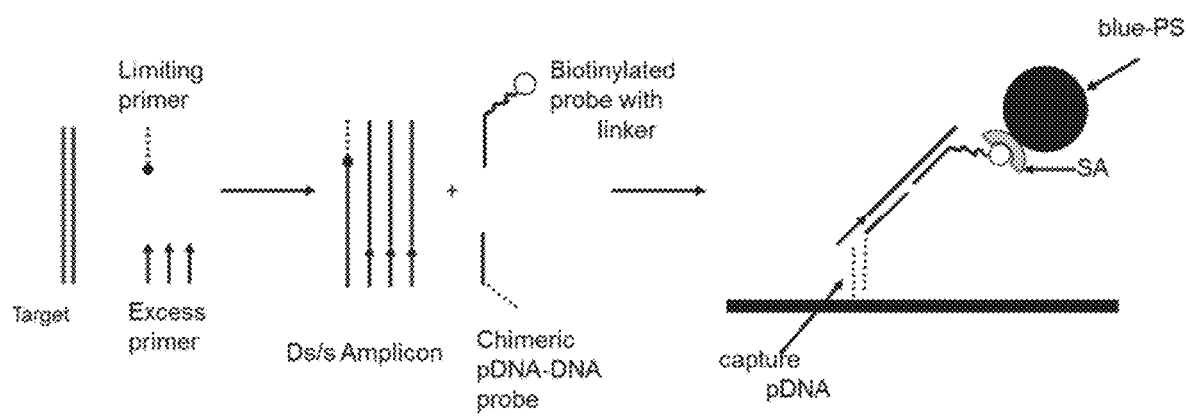
FIG. 1 shows a schematic of an example of dual capture and detection of iSDA amplified amplicon by pDNA immobilized on a solid surface.

Generally, the present disclosure provides methods, primers and probes for the isothermal amplification and detection, without denaturation, of double stranded nucleic acid targets for polymerase strand displacement amplification ("iSDA"). The methods and compositions disclosed are highly specific for nucleic acid targets with high sensitivity, specificity and speed that allow detection of clinical relevant target levels. The methods and compositions can easily be used to amplify or detect nucleic acid targets in biological samples.

According to Ehses et al. (J. Biochem. Biophys. Methods. 63:170-86 (2005), incorporated herein by reference), primers can be designed using the Vienna Folding Package (tbi.univie.ac.at/ivo/RNA/) that identifies analyzes sequences that allowing one to minimize the accumulation of non-predictable byproducts especially for longer incubation times and low concentrations of initial template DNA. More specifically, the Vienna Folding Package is a software product that predicts a secondary structure of the primers based on the calculations of the minimum free energy of the hybridization reaction and calculates the probabilities of alternative DNA/DNA duplex structures. Primers designed using software such as the Vienna Folding Package are considered to have an improved hybridization stringency, and thus permit efficient elongation of a target sequence. The Tm of the selected primers can then be adjusted by calculation with a preferred software package, such as the Eclipse Design Software 2.3 (Afonina et al., Single Nucleotide Polymorphism Detection with fluorescent MGB Eclipse Systems in A-Z of Quantitative PCR, Ed. S. A. Bustin, International University Line, La Jolla, Calif. pages 718-731 and XII-XIII, 2004; see also U.S. Pat. Nos. 6,683,173 and 7,751,982). The software adjusts the Tm of the primers for optimum extension as well, by calculating duplex stabilities using an algorithm applying a nearest-neighbor model for duplex formation thermodynamics for each of the neighboring base pairs. Each nearest neighbor thermodynamic parameter defines a thermodynamic contribution of two corresponding neighboring bases. A preferred oligonucleotide primer sequence is then selected having the desired duplex stability. The primers can also be designed, if necessary or desired, to include modified bases (see U.S. Pat.

Nos. 7,045,610; 6,127,121; 6,660,845; 5,912,340 and US Application Publication No. 2010/057862, all incorporated by reference). In the case of probes or MGB probes, the same software package (such as Eclipse Design Software 2.3) can be used.

II. Definitions

A "sample" as used herein refers to a sample of any source which is suspected of containing a target sequence. These samples can be tested by the methods described herein. A sample can be from a laboratory source or from a non-laboratory source. A sample may be suspended or dissolved in liquid materials such as buffers, extractants, solvents, and the like. Samples also include biological samples such as plant, animal and human tissue or fluids such as whole blood, blood fractions, serum, plasma, cerebrospinal fluid, lymph fluids, milk, urine, various external secretions of the respiratory, intestinal, and genitourinary tracts, tears, and saliva; and biological fluids such as cell extracts, cell culture supernatants, fixed tissue specimens, and fixed cell specimens. Samples include nasopharyngeal or throat swabs, stools, wound or rectal swabs. Biological samples may also include sections of tissues such as biopsy and autopsy samples or frozen sections taken for histological purposes. A biological sample is obtained from any animal including, e.g., a human. A biological sample may include human and animal pathogens that includes microbes or microorganisms such as a viruses, bacteria, or fungi that causes disease in humans. Biological samples may further also include products of gene mutated-metabolic disorders.

The terms "flap primer" or "overhang primer" refer to a primer comprising a 5' sequence segment non-complementary to a target nucleic acid sequence, wherein said tail further comprises a nicking enzyme specific sequence and a 3' sequence segment complementary to the target nucleic acid sequence The flap primers are suitable for primer extension or amplification of the target nucleic acid sequence The primers may comprise one or more non-complementary or modified nucleotides (e.g., pyrazolopyrimidines as described in U.S. Pat. No. 7,045,610 which is incorporated herein by reference) at any position including, e.g., the 5' end.

The term "isothermal strand displacement amplification" ("iSDA") refers to primer extension using a primer that comprises a 5' sequence segment non-complementary to a target nucleic acid sequence, wherein said tail may further comprise a nicking enzyme specific sequence and a 3' sequence segment complementary to the target nucleic acid sequence.

The term "fluorescent generation probe" refers either to a) an oligonucleotide having an attached minor groove binder, fluorophore, and quencher, b) an oligonucleotide having an attached fluorophore, and quencher, c) an oligonucleotide having an attached minor groove binder, and fluorophore, d) an oligonucleotide having an attached fluorophore and quencher, e) an oligonucleotide having an attached fluorophore, or f) a DNA binding reagent. The probes may comprise one or more non-complementary or modified nucleotides (e.g., pyrazolopyrimidines as described in U.S. Pat. No. 7,045,610) at any position including, e.g., the 5' end. In some embodiments, the fluorophore is attached to the modified nucleotide. In some embodiments the probe is cleaved to yield a fluorescent signal.

Preferably, modified bases increase thermal stability of the probe-target duplex in comparison with probes comprised of only natural bases (i.e., increase the hybridization melting temperature of the probe duplexed with a target sequence). Modified bases can decrease probe and primer self-association compared to only normal bases. Modified bases include naturally-occurring and synthetic modifications and analogues of the major bases such as, for example, hypoxanthine, 2-aminoadenine. 2-thiouracil, 2-thiothymine, inosine, 5-$N^4$-ethenocytosine, 4-aminopyrrazolo[3,4-d]pyrimidine and 6-amino-4-hydroxy-[3.4-d]pyrimidine. Any modified nucleotide or nucleotide analogue compatible with hybridization of probe with a nucleic acid conjugate to a target sequence is useful, even if the modified nucleotide or nucleotide analogue itself does not participate in base-pairing, or has altered base-pairing properties compared to naturally-occurring nucleotides. Examples of modified bases are disclosed in U.S. Pat. Nos. 7,045,610; 5,824,796; 6,127,121; 5,912,340; and PCT Publications WO 01/38584; WO 01/64958, each of which is hereby incorporated herein by reference in its entirety. Preferred modified bases include 5-hydroxybutynyl uridine for uridine: 4-(4,6-Diamino-$^1$H-pyrazolo[3.4-d]pyrimidin-3-yl)-but-3-yn-1-ol, 4-amino-$^1$H-pyrazolo[3,4-d]pyrimidine, and 4-amino-$^1$H-pyrazolo[3,4-d]pyrimidine for adenine; 5-(4-Hydroxy-but-1-ynyl)-1H-pyrimidine-2,4-dione for thymine; and 6-amino-$^1$H-pyrazolo[3,4-d]pyrimidin-4(5H)-one for guanine. Particularly preferred modified bases are "Super A®: 4-(4,6-Diamino-1H-pyrazolo[3,4-d]pyrimidin-3-yl)-but-3-yn-1-ol." "Super G®: 4-hydroxy-6-amino pyrazolopyrimidine" (www.elitechgroup.com) and "Super T®: 5-(4-hydroxy-but-1-ynyl)-1H-pyrimidine-2,4-dione". "Super-D™: 3-Alkynyl pyrazolopyrimidine" analogues as universal bases are disclosed in U.S. Patent Application Publication No. 2012/0244535, incorporated by reference.

The terms "fluorescent label" or "fluorophore" refer to compounds with a fluorescent emission maximum between about 400 and about 900 nm. These compounds include, with their emission maxima in nm in brackets. Cy2™ (506), GFP (Red Shifted) (507), YO-PRO™-1 (509), YOYO™-1 (509). Calcein (517). FITC (518), FluorX™ (519), Alexa™ (520), Rhodamine 110 (520). 5-FAM (522), Oregon Green™ 500 (522), Oregon Green™ 488 (524), RiboGreen™ (525). Rhodamine Green™ (527), Rhodamine 123 (529), Magnesium Green™ (531), Calcium Green™ (533), TO-PRO™-1 (533), TOTO®-1 (533). JOE (548). BODIPY® 530/550 (550), Dil (565). BODIPY® 558/568 (568). BODIPY® 564/570 (570). Cy3™ (570). Alexa™ 546 (570), TRITC (572), Magnesium Orange™ (575), Phycoerythrin R&B (575), Rhodamine Phalloidin (575). Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red® (615), Nile Red (628), YO-PRO™-3 (631), YOYO™-3 (631), R-phycocyanin (642). C-Phycocyanin (648). TO-PRO™-3 (660). TOTO®-3 (660). DiD DilC(5) (665), Cy5™ (670). Thiadicarbocyanine (671), and Cy5.5 (694). Additional fluorophores are disclosed in PCT Patent Publication No. WO 03/023357 and U.S. Pat. No. 7,671,218. Examples of these and other suitable dye classes can be found in Haugland et al., Handbook of Fluorescent Probes and Research Chemicals, Sixth Ed., Molecular Probes, Eugene, Ore. (1996); U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Smith et al., J. Chem. Soc. Perkin Trans. 2:1195-1204 (1993); Whitaker, et al., Anal. Biochem. 207:267-279 (1992); Krasoviskii and Bolotin, Organic Luminescent Materials, VCH Publishers, NY.

(1988); Zolliger, Color Chemistry, 2nd Edition, VCH Publishers, NY. (1991); Hirschberg et al., Biochemistry 37:10381-10385 (1998): Fieser and Fieser, REAGENTS FOR ORGANIC SYNTHESIS, Volumes 1 to 17, Wiley, US (1995); and Geiger et al., Nature 359:859-861 (1992). Still other dyes are provided via online sites such as www.zeiss.com. Phosphonate dyes are disclosed in co-owned U.S. Pat. Nos. 7,671,218 and 7,767,834.

There is extensive guidance in the art for selecting quencher and fluorophore pairs and their attachment to oligonucleotides (Haugland, 1996; U.S. Pat. Nos. 3,996,345 and 4,351,760 and the like). Preferred quenchers are described in U.S. Pat. No. 6,727,356, incorporated herein by reference. Other quenchers include bis azo quenchers (U.S. Pat. No. 6,790,945) and dyes from Biosearch Technologies, Inc. (provided as Black Hole™ Quenchers: BH-1, BH-2 and BH-3 quenchers), Dabcyl. TAMRA and carboxytetramethyl rhodamine.

The term "linker" refers to a moiety that is used to assemble various portions of the molecule or to covalently attach the molecule (or portions thereof) to a solid support, surface or membrane. Typically, a linker or linking group has functional groups that are used to interact with and form covalent bonds with functional groups in the ligands or components (e.g., fluorophores, oligonucleotides, minor groove binders, or quenchers) of the conjugates described and used herein. Examples of functional groups on the linking groups (prior to interaction with other components) include —NH2, —NHNH$_2$, —ONH$_2$, —NHC═(O) NHNH$_2$, —OH, and —SH. The linking groups are also those portions of the molecule that connect other groups (e.g., phosphoramidite moieties and the like) to the conjugate. Additionally, a linker can include linear or acyclic portions, cyclic portions, aromatic rings, and combinations thereof.

The term "solid support" refers to any support that is compatible with oligonucleotide attachment, including, for example, glass, controlled pore glass, polymeric materials, polystyrene, beads, coated glass, and the like.

Lateral flow assay technology is well known in the art and is performed on strips of porous paper or sintered polymer see for example U.S. Pat. Nos. 6,485,982, 7,799,554, and 7,901,623.

In the description herein, the abbreviations MGB, FL, Q, CPG, and ODN refer to "minor groove binder," "fluorescent label" or "fluorophore," "quencher." "controlled pore glass" (as an example of a solid support), and "oligonucleotide" moieties or molecules, respectively, and in a manner which is apparent from context. The terms "probe" and "conjugate" are used interchangeably and refer to an oligonucleotide having an attached minor groove binder, fluorophore, and quencher.

The terms "oligonucleotide," "nucleic acid," and "polynucleotide" are used interchangeably herein. These terms refer to a compound comprising nucleic acid, nucleotide, or its polymer in either single- or double-stranded form, e.g., DNA, RNA, analogs of natural nucleotides, and hybrids thereof. The terms encompass polymers containing modified or non-naturally-occurring nucleotides, or to any other type of polymer capable of stable base-pairing to DNA or RNA including, but not limited to, peptide nucleic acids as described in Nielsen et al., Science, 254:1497-1500 (1991), bicyclo DNA oligomers as described in Bolli et al., Nucleic Acids Res., 24:4660-4667 (1996), and related structures. Unless otherwise limited, the terms encompass known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates. 2-O-methyl ribonucleotides, and peptide-nucleic acids (PNAs). A "subsequence" or "segment" refers to a sequence of nucleotides that comprise a part of a longer sequence of nucleotides. In some embodiments, nucleotides may include analogs of natural nucleotides which exhibit preferential binding to nucleotides other than naturally occurring DNA or RNA; an example of such nucleotides is pDNA (Eschenmoser et al. Helvetica Chimica Acta, "Why Pentose- and Hexose-Nucleic Acids?". pp. 76: 2161-2183 (1993)).

The term "Nicking Enzyme (or nicking endonuclease)" describes an enzyme that cuts one strand of a double-stranded DNA at a specifically recognition recognized nucleotide sequences known as a nicking site. Such enzymes hydrolyse (cut) only one strand of the DNA duplex, to produce DNA molecules that are "nicked", rather than cleaved. These nicking enzymes include N.Alw I, Nb.BbvCI, Nt.BbvCI, Nb.BsmI, Nt.BsmAI, Nt.BspQI, Nb.BsrDI, Nt.BstNBI. Nb.BstsCI, Nt.CviPII, Nb.Bpu10I, Nt.Bpu10I and Nt.Bst9I which are commercially available from www.neb.com, www.fermentas.com and www.sibenzyme.com, respectively. The New England Biolabs REBASE website (rebase.neb.com/cgi-bin/azlist?nick) lists 917 nicking enzymes. Designing of artificial nicking endonucleases on the basis of restriction endonucleases was reviewed by Zheleznaya et al., Biochemistry (Mosc). 74:1457-66 (2009), incorporated by reference. "Nicking Enzyme" also includes engineered enzymes that cut one strand of a double stranded DNA, for example, zinc finger nucleases.

The term "Lateral Flow" describes a porous membrane capable of nonabsorbent lateral flow used as assay substrate; a member of the binding pair is affixed in an indicator zone defined in the substrate. The sample is applied at a position distant from the indicator zone and permitted to flow laterally through the zone; any analyte in the sample is complexed by the immobilized specific binding member, and detected. Lateral flow utilizing immuno-binding pairs is well known in the art (U.S. Pat. No. 4,943,522). Lateral flow using DNA binding pairs was disclosed in U.S. Pat. No. 7,488,578, pDNA binding pairs are disclosed in co-owned US application 2012-0015358 A1. Biotin-streptavidin affinity pairs are well known in the art and commercially available. Streptavidin-coated label may be a covalent or adsorptively bound streptavidin or other biotin-binding species, and the label may be a polystyrene nanoparticle doped with fluorescent or visible dye, a carbon black nanoparticle, a metal colloid, or other species detectable by fluorescence, radioactivity, magnetism, or visual acumen. The lateral flow buffer may be an aqueous suspension containing detergents, proteins, surfactants, and salts. The lateral flow strip may be a porous matrix composed of nitrocellulose, modified nitrocellulose, polyethersulfone, cellulose, glass fiber, polyvinylidene fluoride, or nylon. The lateral flow strip has at least one detection region composed of affinity pairs specific to the iSDA reaction products.

The practice of the methods described herein will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis. MOLECULAR CLONING: A LABORATORY MANUAL, Second Edition. Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

III. Descriptions

Figure 8:
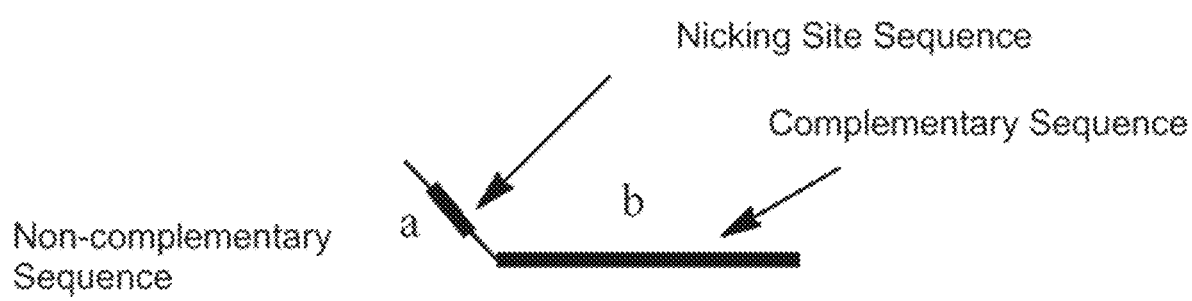
FIG. 8 shows a schematic representation of a primer containing a complementary- and non-complementary-sequence.

In one aspect, this disclosure provides an isothermal method for specifically detecting a nucleic acid sequence in a biological sample from an individual. The isothermal method can be carried out entirely at room temperature, or between about 40° C., and about 65° C., or more preferably between about 45° C., and about 55° C. The disclosure also provides oligonucleotide primers and probes comprising nucleotide sequences characteristic of a specific genomic nucleic acid sequences. The method includes performing of isothermal amplification without a denaturation step prior to amplification. The amplification step includes contacting the sample nucleic acid with pairs of primers to produce amplification product(s) if the specific genomic nucleic acid target is present. The primer "A-B" comprises a complementary sequence "B" and comprises a non-complementary nicking enzyme recognition sequence site "A" when hybridized to a complementary sequence (FIG. 8). Primer A-B further comprises sequences selected by free energy minimization for specific hybridization and efficient elongation. The primers target a specific region of a specific target gene that allows amplification without thermal denaturation. Bumper primers hybridize upstream of the 5'-end of the flap primers to generate a target specific single stranded DNA newly synthesized amplicon by strand displacement (Nuovo G J., Diagn Mol Pathol. 2000 December; 9(4): 195-202). The oligonucleotide probes detect the amplified target directly or indirectly. The preferred oligonucleotide probe is a 5'-minor groove binder-fluorophore-oligonucleotide-quencher-3' conjugate that fluoresces on hybridization to its complementary amplified target.

In some embodiments the probe(s) is omitted. In some embodiments the amplified target is captured on a solid support, surface or membrane and detected by a labeled probe. In some embodiments the primer concentrations are present in different concentrations. In some embodiments an internal control is provided.

In a particular embodiment human, animal, and/or plant pathogen nucleic acids are amplified and detected.

In another embodiment the amplified target nucleic acid is RNA and the method further comprises a reverse transcriptase step.

In another aspect, the 5' non-complementary sequence comprises a sequence for a nicking site. Although any enzyme with a suitable nicking site can be used, preferred nicking enzyme recognition sequences are selected from N.Alw I. Nb.BbvCl, Nt.BbvCl, Nb.BsmI, Nt.BsmAI, Nt.BspQI, Nb.BsrDI, Nt.BstNBI, Nb.BstsCI, Nt.CviPII, Nb.Bpu10I, Nt.Bpu10I and Nt.Bst9I, Nb.Mval269I and endo nuclease V.

In another embodiment, a complementary primer sequence comprises a sequence with an Endonuclease V ("Endo V") cleavage site requiring no heat or chemical denaturation, as more fully described in U.S. Pat. No. 8,202,972 or U.S. Patent Application Publication No. 2011/0171649 incorporated by reference, which describes Endo V-based amplification primers. More specifically Endonuclease V is a repair enzyme recognizing DNA oligonucleotides containing deaminated modified bases such as inosine. Endo V cleaves the second or third phosphodiester bond 3' to the modified base, such as inosine. U.S. Pat. No. 8,202,972 describes an Endonuclease V-based amplification method that extends a forward- and reverse-primer containing inosine adjacent to 3'-end terminal base. In the second round of amplification the Endo V cleaves the second or third phosphodiester bond 3' to the inosine in the same strand. The 3'-hydroxyl of the nick is extended by DNA polymerase in a template-directed manner. Employing a series of nested primer pairs complementary upstream of the 5'-end of the inosine containing primer pair, a series of extension products are generated. U.S. Pat. No. 8,202,972 requires that "target dsDNA may be thermally denatured, chemically denatured, or both thermally and chemically denatured".

Figure 4:
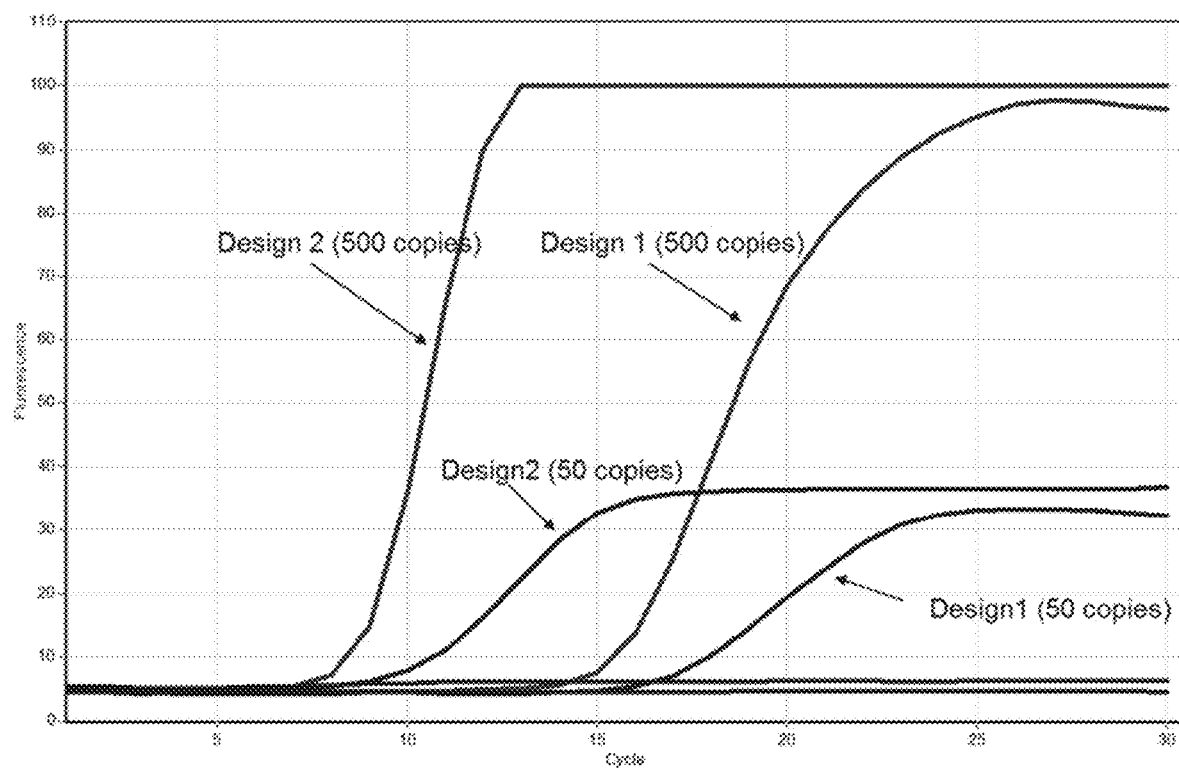
FIG. 4 shows an example of real-time iSDA amplification of two different mecA designed assays with fluorescence detection utilizing a Pleiades probe.

In additional preferred embodiments, the primers used in the isothermal strand displacement amplification (iSDA) methods are designed to first require the identification of sequences in double-stranded nucleic acids (NA) where Watson-Crick pairs spontaneously flip into Hoogsteen pairs under ordinary conditions, a phenomenon that has led to the suggestion that DNA "breathes" (Fran-Kamentskii (2011)). According to Ehses et al (2005), incorporated herein by reference, primers can be designed using the Vienna Folding Package (thi.univie.ac.at./ivo/RNA/), a software program that identifies sequences that allow one to minimize the accumulation of non-predictable byproducts especially for longer incubation times and low concentrations of initial template NA. The Vienna Folding Package can be used to predict a secondary structure of NA sequences, including primers, based on the calculations of the minimum free energy of the hybridization reaction and to calculate the probabilities of alternative DNA/DNA duplex structures. Due to the potential interactions amongst primer sequences, some assay designs work significantly better than others. An example of that is seen in FIG. 4, where the mecA design 1 at 50 copies shows a Ct of about 15 while design 2 at the same concentration shows a Ct of 8. Assays for iSDA designed with this software product can show little or no amplification.

It is therefore important to identify and avoid potential interactions among primer sequences and to minimize the adoption of assay and primer designs that will not produce any iSDA amplification. It is therefore preferable to identify sequences that "breathe" in dsDNA, allowing for the design of primers that hybridize to the resulting single-stranded sequences and can be extended without taking steps to produce denaturation.

DNA denaturation and bubble formation in ds nucleic acids can be modelled by various methods. A prominent method uses the Peyrard Bishop Dauxois (PBD) model (Dauxois et al., 1993), based on Langevin equations including the following parameters: Morse potential for hydrogen bonding, adjacent base-pair stacking interactions, thermal noise and other sequence-independent parameters. A variation of the PBD model is the helicoidal model which addresses torque-induced denaturation. Another alternative is the Poland-Scheraga free energy model, described by Metzler et al., 2009. These methods employ cooperativity factors for ranges of polymer length to describe local denaturation.

Figure 14:
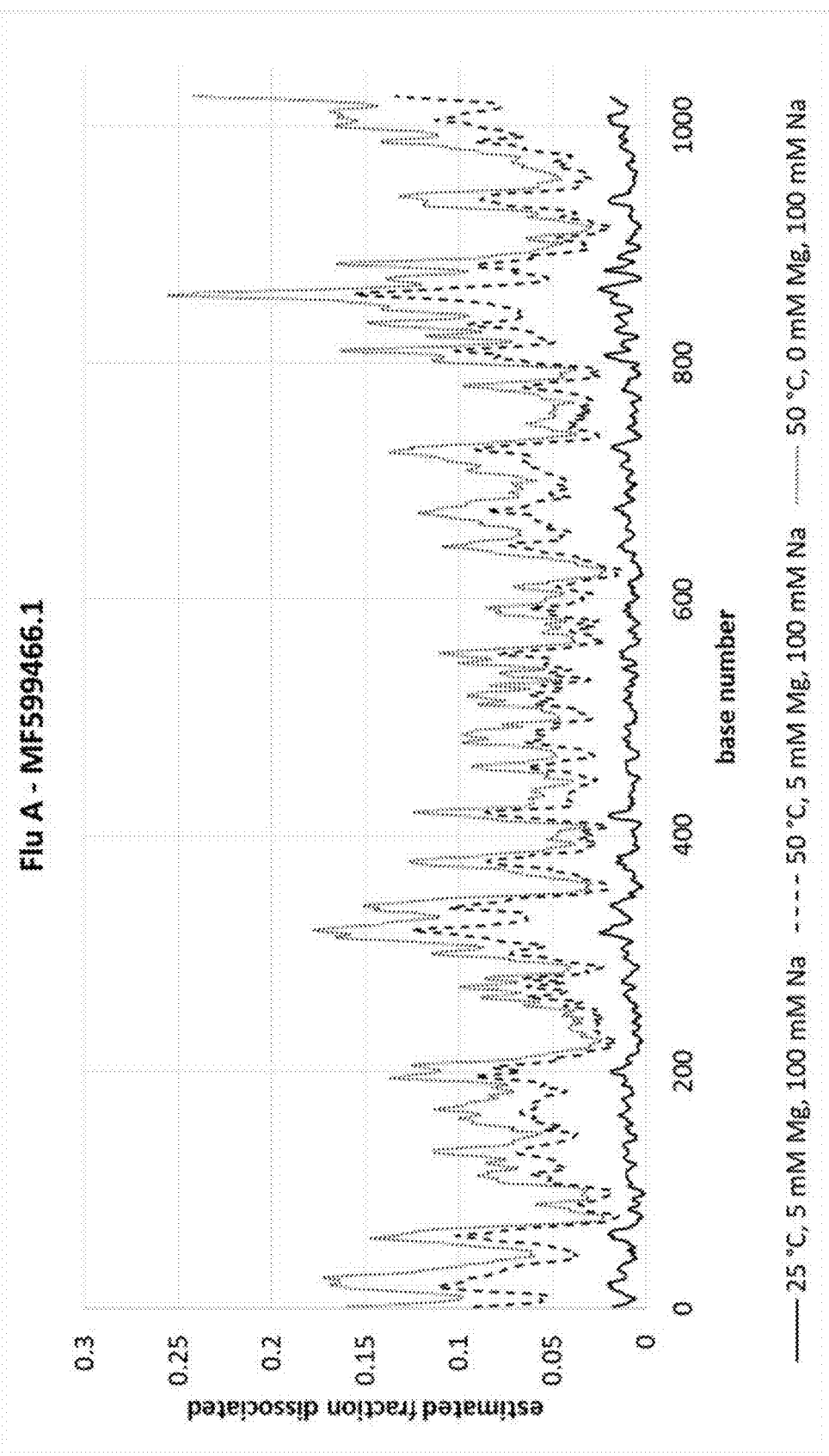
FIG. 14 shows estimated fractions of dissociated bases within subregions of Influenza A virus segment 7 matrix protein 2 (M2) and matrix protein 1 (M1) genes with varying salt and temperature.

In preferred embodiments described herein, an additional method of modeling and predicting DNA breathing regions is presented. Tm prediction parameters, which are well-established (SantaLucia. Jr. (1998)) for DNA, can be applied to subsequences in a longer DNA sequence. Specifically, enthalpy and entropy values for nearest neighbors are calculated for each subsequence in an ordered walk to create a profile of interstitial stability along the length of the entire sequence. Short-range (as short as two nucleobases) can be combined with longer (50 nucleobases or more) subsequences to account for long range effects mimicking cooperativity in the PBD and Poland-Scheraga models. To design primers for iSDA, it is useful to account for reaction temperature and salt conditions. Salt conditions can be used to generate a predicted Tm for each subsequence, and growth rate of the dissociation curve can be estimated based on enthalpy values (Mergny and Lacroix, (2003)). With an estimate of the shape of the sigmoidal dissociation curve, the fraction of associated base pairs can be calculated for each subsequence at a particular temperature, and the values plotted over the length of the entire sequence of interest for parameters such as salt content or temperature of analysis as shown in FIG. 14. Sequences with a higher estimated fraction of dissociation allow for the favorable design of primers that can hybridize to those sequences without the requirement of denaturation.

Accordingly, preferred embodiments of the present methods for isothermal strand displacement amplification include an initial step in which a target sequence is analyzed to determine estimated fractions of dissociated bases along the length of the target sequence. The estimated fractions of dissociated bases are calculated by determining enthalpy and entropy for each base in the target sequence using established nearest neighbor dimer values (see SantaLucia, 1998), then using the enthalpy and entropy values to calculate a Tm estimate for each base in the target sequence, then calculating a sigmoidal melt curve growth rate estimate for the target sequence using enthalpy, and then constructing a simulated melt curve to estimate the fraction dissociated for the target sequence at a particular temperature. Primers are then designed to hybridize to those regions of the target sequence having a higher estimated fraction of dissociated bases. In preferred embodiments, at least one primer should be designed to hybridize to those portions of the target sequence having an estimated fraction of dissociated bases of about 0.04 to about 0.2 and preferably in the range of about 0.05 to 0.15. Primers designed to hybridize to these particular sequences are more likely to successfully hybridize to single-stranded DNA, without requiring the use of any artificial methods such as heat to produce denaturation. Thus, these primers work effectively in iSDA methods.

In one preferred embodiment, primers are designed to hybridize to a target sequence in a region of the target sequence having an estimated fraction of dissociated bases of at least 0.04, and preferably the primers are designed to hybridize in one or more regions of the target sequence that are determined to have the maximized estimated fraction of dissociated bases for that particular target sequence.

In an additional preferred embodiment, a set of sequences are constructed that are within the full target sequence and the estimated fractions of dissociated bases are calculated for each subsequence. The enthalpy and entropy values are calculated for each subsequence then used to estimate Tm for the subsequence and a melt curve rate around each base of interest. Then, the average value of the estimated fractions of dissociated bases is calculated for each subsequence.

In an additional preferred embodiment, a primer is designed to bind to a target sequence in a region of the target sequence that has a favorable estimated fraction of dissociated bases, preferably higher than 0.04.

A variety of methods utilizing isothermal amplification methods are known and can be utilized in conjunction with the methods disclosed herein. These include Strand Displacement (SDA), Exponential amplification (EXPAR), Loop-mediated amplification (LAMP). Transcription-mediated amplification (TMA)/Nucleic acid-based amplification (NASBA), Recombinase polymerase amplification (RPA). Helicase-dependent amplification (HAD), and others (Niemz et al., 2011).

In additional preferred embodiments, the iSDA methods are performed with digital PCR or in a digital format that allows for the determination of absolute nucleic acid concentration. Digital PCR is an established diagnostic tool (Pohl and Shih (2004); Sedlak and Jerome, Diagn Microbiol Infect Dis., (2013)). Digital PCR (dPCR) is based on a combination of limiting dilution, end-point PCR, and Poisson statistics to determine the absolute measure of nucleic acid concentration (U.S. Pat. No. 6,440,706). The use of short MGB FRET probes in dPCR is disclosed in U.S. Pat. No. 9,328,384, incorporated by reference.

In additional preferred embodiments, the iSDA methods are performed using probes that include the abasic spacer. As discussed, some preferred embodiments for iSDA amplification involve the use of probes (Pleiades probes) such as those described herein and shown in FIG. 2. Examples of these probes are disclosed in U.S. Pat. No. 7,381,818. Pleiades probes include a MGB and a fluorescent dye attached at 5' end' and a quencher at 3' end of an oligonucleotide that may also include one or more modified bases. Probes that include an abasic spacer are additional preferred embodiments. Real-time iSDA detection shows strong sample amplification and absence of the signal in the NTC samples for the probes including the abasic spacer compared to other probes.

Further preferred embodiments of the iSDA methods described herein utilize probes including the abasic spacer and an endonuclease that is Endonuclease IV. By way of explanation, the DNA of all species is exposed to both endogenous and exogenous factors, which damage its chemical structure. The most common lesion that arises in cellular DNA is the loss of a base to generate an abasic site, which is typically referred to as an apurinic or apyrimidinic (AP) site. To counteract the possible cytotoxic and mutagenic effects of apurinic/apyrimidinic lesions, cells of all organisms express dedicated repair enzymes, known as AP endonucleases, to counteract their damaging effects (Barzilay G, Hickson I D. Bioessays. 17(8):713-9 (1995)). U.S. Patent Publication US2009/0092967 disclosed the Endonuclease IV detection system coupled to isothermal amplification. U.S. Pat. No. 7,252,940 described Endonuclease IV amplification as a post amplification PCR detection system comprising a labeled probe and a helper oligonucleotide.

As such, preferred embodiments herein relate to an oligonucleotide probe for use in iSDA amplification and detection that have the following structure:

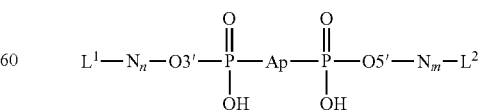

wherein O3' is the 3' oxygen atom of the 3'-terminal deoxyribose ring of one nucleotide sequence ($N_n$).
O5' is the 5' oxygen atom of the 5'-terminal deoxyribose ring of another nucleotide sequence ($N_m$), N is a natural or artificial nucleotide or a nucleoside unit.
n and m are independently from about 5 to about 15,
$L^1$ and $L^2$ are independently a fluorophore and a quencher, which are covalently bonded to $N_n$ and $N_m$ respectively, and Ap is comprised of the following substructure:

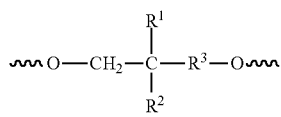

wherein $R^1$, $R^2$ are selected from H, substituted or unsubstituted hydroxyl, amine, thiol, ($C_1$-$C_{100}$)alkyl, ($C_1$-$C_{100}$)heteroalkyl, ($C_1$-$C_{100}$)alkenyl, ($C_1$-$C_{100}$)heteroalkenyl, ($C_1$-$C_{100}$)alkynyl, ($C_1$-$C_{100}$)heteroalkynyl aryl or heteroaryl;
$R^3$ is selected from substituted or unsubstituted ($C_1$-$C_{100}$) alkylene or ($C_1$-$C_{100}$)heteroalkylene; optionally, any combination of groups selected from $R^1$, $R^2$ and $R^3$ forms one or more, saturated or unsaturated, substituted or unsubstituted 4 to 10 member carbon or heteroatomic rings;
and wherein the oligonucleotide probe is cleaved by an endonuclease to produce a fluorescent signal.

Additional preferred embodiments herein relate to an oligonucleotide probe for use in iSDA amplification and detection that have the following structure:

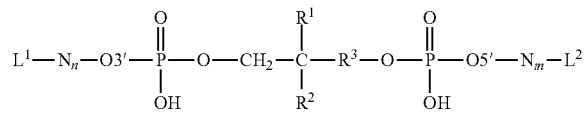

wherein the substituents are defined as above.

Figure 25A:
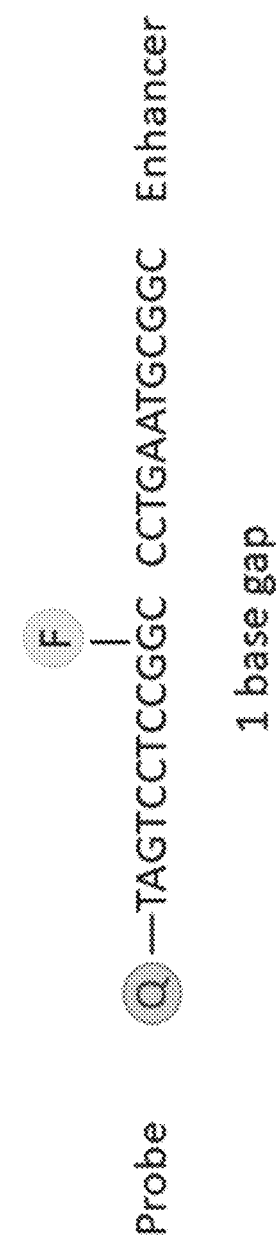
FIG. 25A shows an example structure of a typical Endonuclease IV probe (SEQ ID NO:83) and enhancer (SEQ ID NO:84) detection system.
Figure 25B:
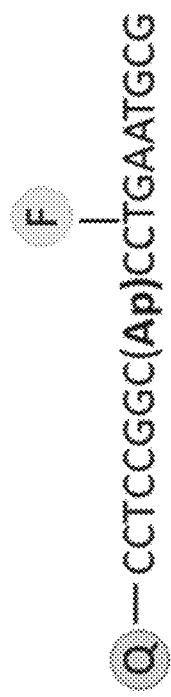
FIG. 25B shows an exemplary probe containing the abasic spacer as disclosed herein (SEQ ID NO:82) for use with Endonuclease IV.

Additional preferred embodiments relate to a method for iSDA amplification and detection using a probe having the structures above containing the abasic spacer, comprising a step in which the probe is cleaved by an endonuclease, which may be Endonuclease IV. In additional preferred embodiments the probe having the structure above is cleaved enzymatically to generate a fluorescent signal. FIG. 25A shows an example structure of a typical Endonuclease IV probe and enhancer detection system. There is a one base gap in target sequence, between the probe and the enhancer. FIG. 25B shows an exemplary probe containing the abasic spacer as disclosed herein for use in detection similar to FIG. 25A using Endonuclease IV. Instead of a one base gap, the abasic spacer is included. Preferred embodiments described herein, utilizing post amplification iSDA methods, have shown strong sample amplification compared to the system shown in FIG. 25A, with a low IC signal. In contrast to the system shown in FIG. 25A, in preferred embodiments using the probes with abasic spacers shown above, the probes are digested into two pieces, each piece having a Tm substantially lower than the iSDA reaction temperature, limiting potential interactions. In additional preferred embodiments, Endonuclease IV cleavage of probes including abasic spacers having the structure shown above is coupled to an amplification reaction. Polymerase-based and isothermal amplification reactions are well known in the art. An Endonuclease IV post-PCR amplification reaction detection has been reported (Kutyavin, Nucleic Acids Res. 34: e128 (2006)).

Figure 26B:
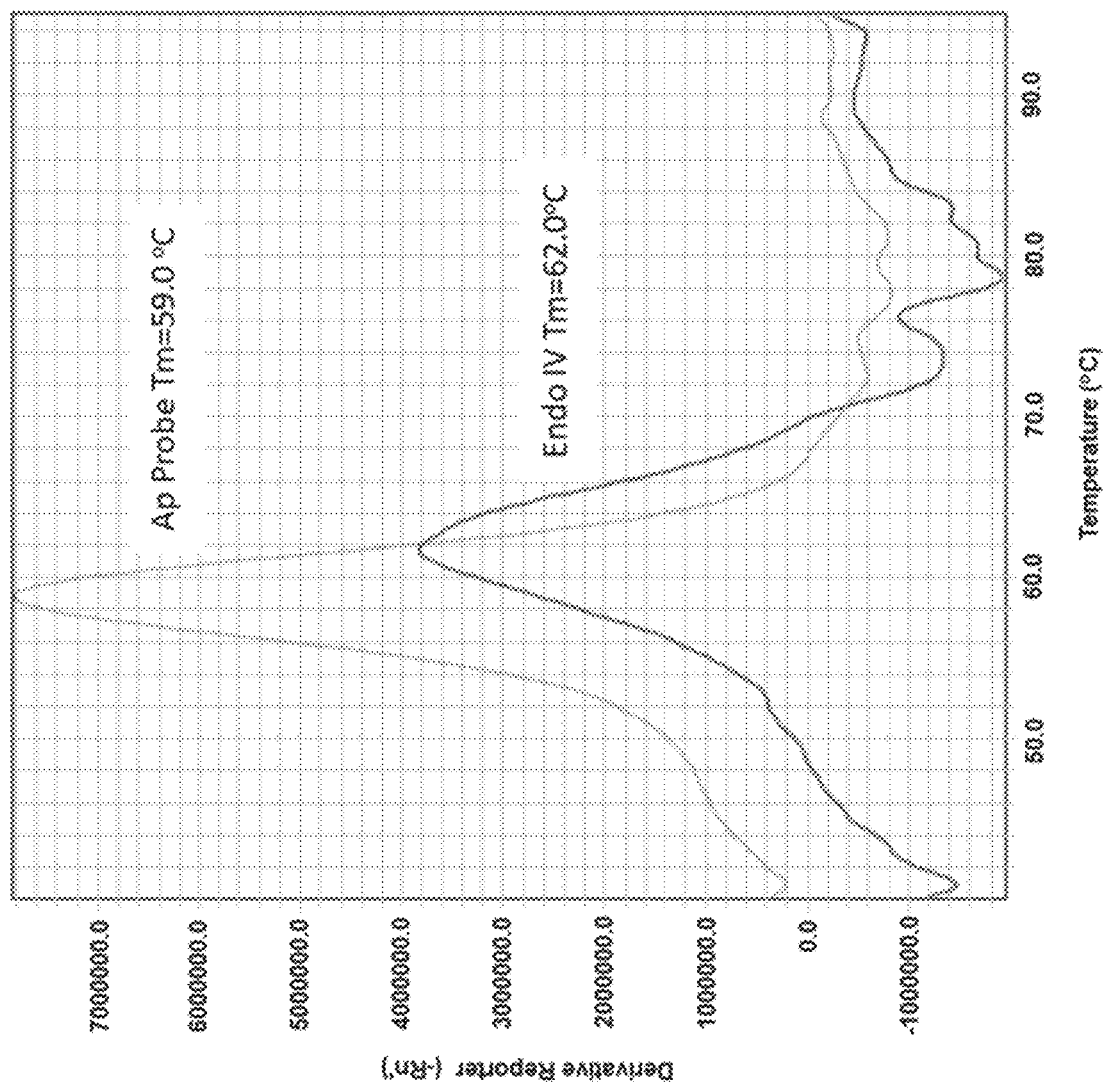
FIG. 26B shows a meltcurve analysis of a typical undigested Endonuclease IV probe ("Endo IV") compared to an undigested probe containing the abasic spacer ("Ap Probe") according to preferred embodiments disclosed herein, both with a synthetic complement.
Figure 26A:
FIG. 26A shows melting temperature of each portion of a digested probe containing the abasic spacer (SEQ ID NO:82) according to preferred embodiments disclosed herein.

Without being bound by a particular theory, the better efficiency of the preferred embodiments described herein, where the probe includes the abasic spacer and is cleaved by Endonuclease IV, can likely be explained by the cycling mechanism of the signal generation. The melting temperatures of the products, produced by Endo IV enzyme cleavage, are lower than the iSDA reaction temperature. The melting temperature of each portion of the digested probe is 46.0° C. as shown in FIG. 26A. FIG. 26B shows a meltcurve analysis of a typical undigested Endonuclease IV probe ("Endo IV") (SEQ ID NO:83) compared to an undigested probe containing an abasic spacer ("Ap Probe") (SEQ ID NO:82), both with a synthetic complement. The Endo IV probe has a Tm of 62.0° C. and the Ap probe has a Tm of 59.0° C. Therefore, the digested products cannot compete for the binding site with the undigested probe. They dissociate from the target and make it accessible for the intact probe to hybridize, get cleaved and release the fluorescent signal. This mechanism is quite different from the conventional probes used in typical Endo IV amplification, where the digested probe is essentially the same probe lacking a fluorophore. Once cleaved it can still occupy the target, preventing the binding of the undigested probe. This in turn affects the signal in the iSDA reaction, especially in the case of the low positive samples.

Preferred abasic spacers (Ap in the structure above) may be introduced into the probe during automated oligonucleotide synthesis using a phosphoramidite compound, such as any of the phosphoramidite compounds shown below in Table A.

TABLE A

Abasic Spacer Phosphoramidites

| Spacer # | Phosphoramidite Structure | Spacer Structure (Ap) |
|---|---|---|
| 1 | | |

TABLE A-continued

Abasic Spacer Phosphoramidites

| Spacer # | Phosphoramidite Structure | Spacer Structure (Ap) |
|---|---|---|
| 2 | [structure: DMT-O-propyl-O-P(N(iPr)2)-O-CH2CH2CN] | [structure: ~O-propyl-O~] |
| 3 | [structure: DMT-O-CH2-furanose(OMe)-O-P(N(iPr)2)-O-CH2CH2CN] | [structure: ~O-CH2-furanose(OMe)-O~] |
| 4 | [structure: DMT-O-CH2-tetrahydrofuran-O-P(N(iPr)2)-O-CH2CH2CN] | [structure: ~O-CH2-tetrahydrofuran-O~] |

In additional preferred embodiments, the abasic spacer (Ap) in the structure shown above, is one of the spacers shown below in Table B.

TABLE B

| Spacer # | Structure |
|---|---|
| 5 | [structure] |
| 6 | [structure] |
| 7 | [structure] |
| 8 | [structure] |
| 9 | [structure] |

TABLE B-continued

| Spacer # | Structure |
|---|---|
| 10 | [structure] |
| 11 | [structure] |
| 12 | [structure] |
| 13 | [structure] |

Synthesis of the requisite phosphoramidite from each of the spacers listed in Table C, for incorporation into oligonucleotides during automated synthesis, is known in the art and is further described in US20110151457.

Preferred embodiments herein relate to methods for iSDA using probes that include an abasic spacer. These methods are improvements upon existing technology utilizing the Endo IV enzyme because they do not require a separate enhancer oligonucleotide and are also improvements upon existing technology for iSDA using the Pleiades probe because they show enhanced sensitivity.

EXAMPLES

The following examples are provided to illustrate, but not to limit, the subject matter described herein.

In these examples, iSDA was performed using final concentrations of 3.75 mM MgSO$_4$, 50 mM KH$_2$PO$_4$ pH 7.6, 250 nM forward primer, 1 µM reverse primer, 50 nM bumper oligonucleotides, 200 nM probe, 0.2 mM dNTPs, 40 µg/mL BSA, 10 ng genomic DNA, 4 U N.BbvC1B and 3.6 U Bst DNA polymerase in a total volume of 20 µL (mono-reagent). Twenty microliters of the mono-reagent was introduced in a 96 well PCR plate with 10 µL of sample nucleic acid. Sample nucleic acid was obtained by extraction with easyMag using NucliSENSE easyMAG extraction reagents (Biomerieux, l'Etoile, France). The plate was sealed with MicroAmp® Optical Adhesive Film (Applied Biosystems. Foster City, Calif.) and then centrifuged to collect the assay solution in the bottom of the plate well. The assay was then performed in an ABI 7500 DX Fast Block Real-time PCR machine at 48° C. for 30 minutes.

Example 1

This example demonstrates the efficient iSDA amplification without denaturation of the Idh1 gene from easyMag extracted nucleic acid from cultured *S. aureus* subsp. *aureus* COL (gi157650036:262250-263203). The primer, bumper and probe sequences are shown in Table 1.

Table 1 below illustrates Idh1 oligonucleotide sequences for iSDA amplification. Underlined sequences represents the nicking site for N.BbvC1B. The upper case sequence is Idh1 specific, the 5'-end lower case sequence is non-complementary to the Idh1 target, and the pDNA sequence is shown in brackets. Q14 is a hexaethylene glycol linker. MGB is a DPI$_3$ minor groove binder, FAM is fluorescein, and EDQ is the Eclipse® dark quencher (quenching range 390-625 nm, maximum absorption 522 nm, Epoch Biosciences, Inc., Bothell. Wash.).

TABLE 1

| Seq ID # | Description | Oligonucleotide sequence |
|---|---|---|
| 1 | Forward Primer | gcataatactaccagtct<u>cctcagc</u>AAGCTAC GCATTTTCATTAG |
| 2 | Reverse Primer | tagaatagtcgcatactt<u>cctcagc</u>CATAACA TCTCCTCGAACT |
| 3 | Probe | MGB-FAM-CTAATTCATCAACAATGC-EDQ |
| 4 | Forward Bumper | AGGTAATGGTGCAGTAGGT |
| 5 | Reverse Bumper | CCAGCTTTCACACGAAC |

TABLE 1-continued

| Seq ID # | Description | Oligonucleotide sequence |
|---|---|---|
| 6 | pDNA Capture Probe | [TTTTTTTTC]-(Q14)-CAGTGTCTAAATCA ATGATG |
| 7 | Biotini- lated Detection Probe | CTAATTCATCAACAATGC-biotin |

Figure 2:
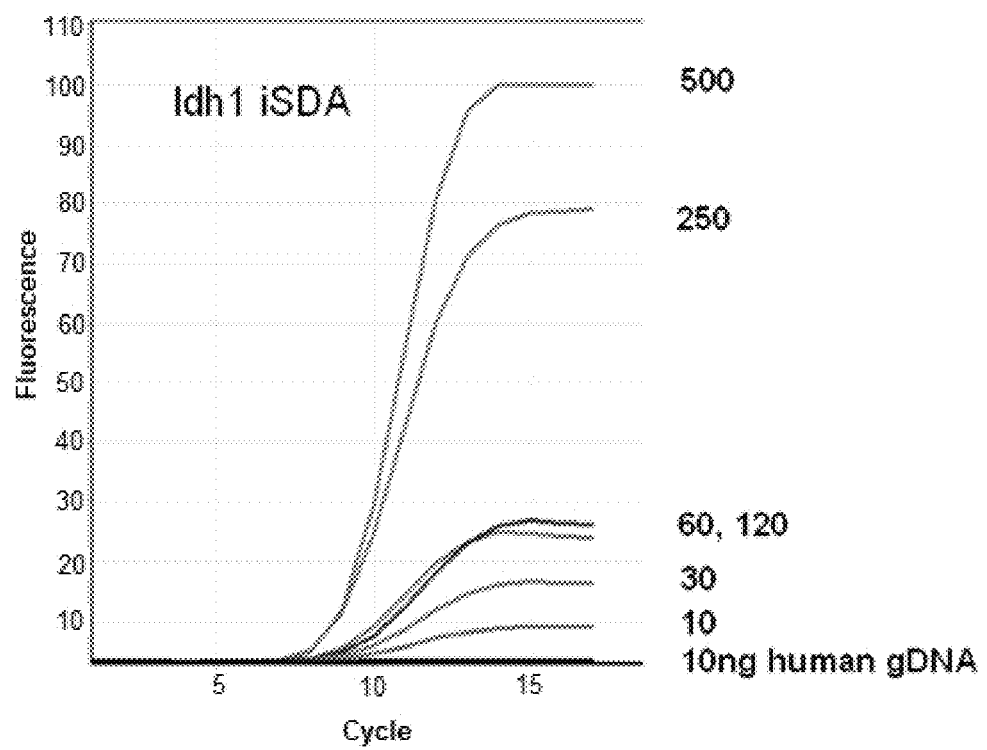
FIG. 2 shows an example of real-time iSDA amplification of different concentrations of the Idh1 gene with fluorescence detection utilizing a Pleiades probe.

Real-time iSDA amplification with oligonucleotide 1 to 5 was performed as described above with target concentrations ranging from 10 to 500 copies per reaction. The results are shown in FIG. 2.

Figure 3:
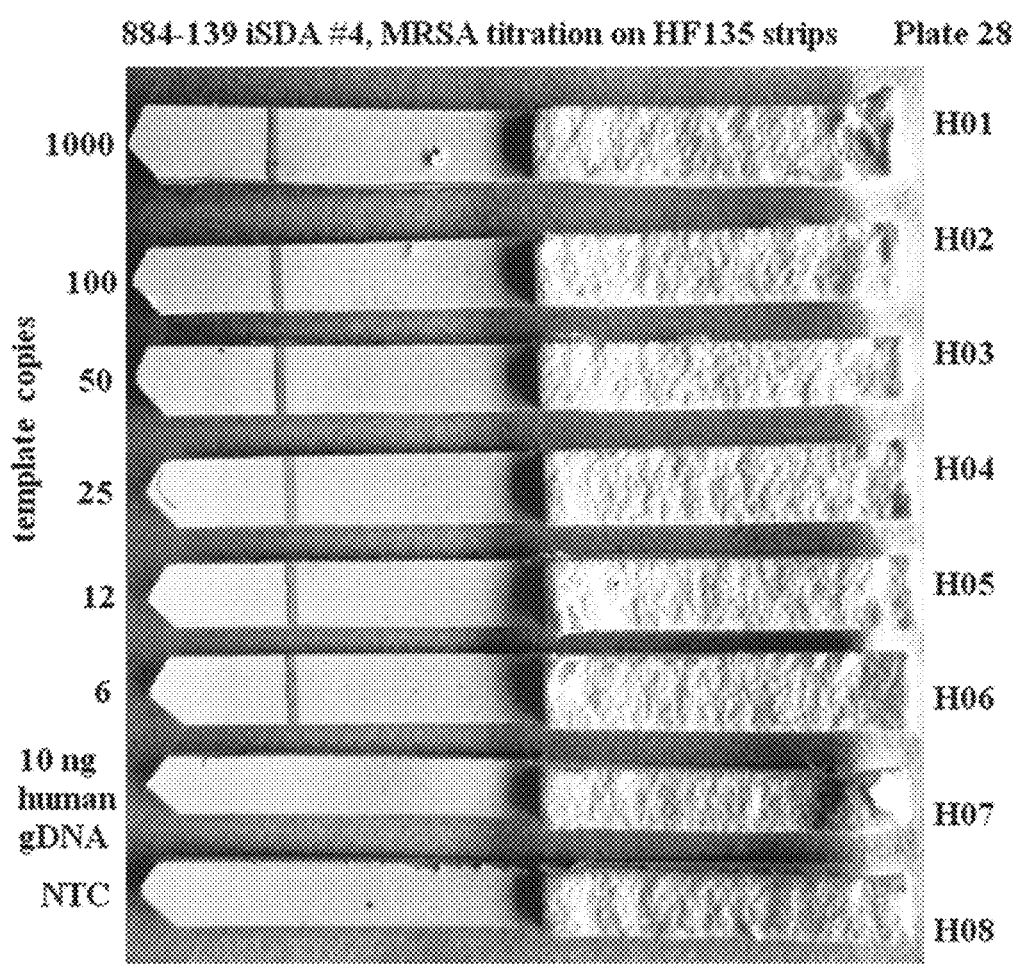
FIG. 3 shows an example of lateral flow colorimetric detection of an Idh1 iSDA amplified amplicon with the approach provided in FIG. 1.

Lateral Flow:

A similar iSDA amplification was performed except that probe 3 was replaced with probes 6 and 7 that allow capture and detection in a lateral flow format, as schematically depicted in FIG. 1, with the results shown in FIG. 3. Once the iSDA reaction was complete, 2 µL of the product was aliquoted into a well containing a streptavidin-coated label and a volume of buffer for running the lateral flow assay on HF135 nitrocellulose (Millipore), then the lateral flow strip was added to the well. In one example, 2 µL of the iSDA Idh1 reaction mixture was diluted in 100 µL of lateral flow buffer with the formulation 15 mM HEPES (pH 8), 1% Triton X-100, 0.5% BSA, 400 mM NaCl, 0.05% NaN$_3$, and 100 ng/p L streptavidin-coated 300 nm diameter blue-dyed polystyrene nanoparticles (Seradyn). To the diluted product was then added a nitrocellulose strip, 4×25 mm, containing an immobilized pDNA oligo complementary to the pDNA capture probe 6. The pDNA was immobilized via a cross-linked polythymidine tail at a concentration of 120 pmol/cm and a line width of approximately 1 mm. Positive results were visualized easily by the naked eye (as seen in FIG. 3).

Example 2

This example illustrates the versatility of the design of primers from mecA gene sequences to allow iSDA amplification without denaturation. Nucleic acid was easyMag extracted from cultured *S. aureus* subsp. *aureus* COL. The primer, bumper and probe sequences of Design 1 and 2 are shown below in Table 2. The pDNA sequence is shown in brackets.

Table 2 below shows Designs 1 and 2 oligonucleotide sequences for mecA amplifications. Underlined sequences represent the nicking site for Nt.BbvC1B, the upper case sequence is mecA specific, the 5'-end lower case sequence is non-complementary to the mecA target, the pDNA sequence is shown in brackets, A* is Super A (U.S. Pat. No. 7,045, 610), and Q14 is a hexaethylene glycol linker.

TABLE 2

| Seq ID # | Description | Oligonucleotide sequence |
|---|---|---|
| Design 1 | | |
| 8 | Forward Primer | gaaacaatgtacctgtca<u>cctcagc</u>GACCGAAA CAATGTGGAAT |
| 9 | Reverse Primer | ttcaatagtcagttacttcctcagcGGAACGAT GCCTAATCTCA |
| 10 | Probe | MGB-FAM-CCAATACAGGAACACAT-EDQ |

TABLE 2-continued

| Seq ID # | Description | Oligonucleotide sequence |
|---|---|---|
| 11 | Forward Bumper | GAAAATTTAAAATCAGAACGTGG |
| 12 | Reverse Bumper | GCTTTA*TAATCTTTTTTAGATAC |
| 13 | pDNA Capture Probe | [TTTTTTTTC]-(Q14)-CAATGTGGA*ATTGG |
| 14 | Biotinilated Detection Probe | CCAATACAGGAACACAT-biotin |
| Design 2 | | |
| 15 | Forward Primer | ccattatactacctgtctcctcagcGGCAAAGATATTCAACTAAC |
| 16 | Reverse Primer | tagaatagtcagttacttcctcagcGCCATAATCATTTTTCATGTTG |
| 17 | Probe | MGB-FAM-CTTTTGAACTTTAGCATC-EDQ |
| 18 | Forward Bumper | GATAATAGCAATACAATCGCACA |
| 19 | Reverse Bumper | GTGCTAATAATTCACCTGTTTGA |
| 20 | pDNA Capture Probe | [CAAGAATC]-(Q14)-CTTTAGCATCAATAGTTAG |
| 21 | Biotinilated Detection Probe | GTTA*TAAATA*CTCTTTTGA-biotin |

Using primers, probe and bumper oligonucleotides (Design 1, Seq. ID #8-12 and Design 2, Seq. ID #15-18) in the same way described in Example 2, efficient real-time iSDA was achieved as shown in FIG. 4.

Example 3

Figure 5:
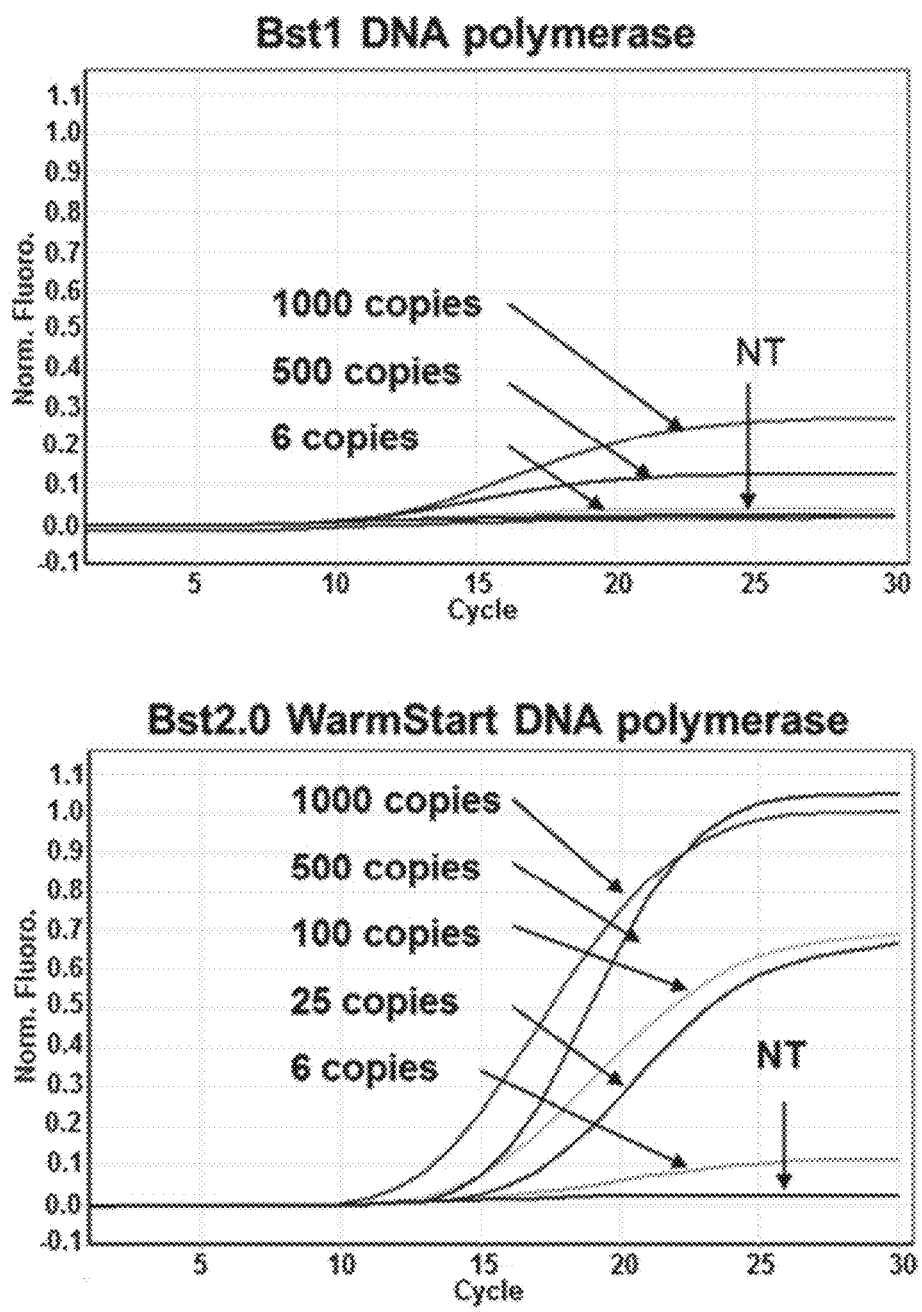
FIG. 5 shows an example of real-time iSDA amplification with different polymerases.

This example demonstrates the use of different polymerases in the real-time iSDA amplification. iSDA amplification was performed as described above using either Bst DNA Polymerase (portion of *Bacillus stearothermophilus* DNA Polymerase, New England BioLabs Inc., Ipswich. Mass.) or Bst2.0 WarmStart (an in silico designed homologue of *Bacillus stearothermophilus* DNA Polymerase 1, New England BioLabs Inc.). The latter enzyme amplified mecA target and is active above 45° C. The results are shown in FIG. 5, indicating better performance with the Bst2.0 WarmStart enzyme.

Example 4

This example demonstrates that although the Nt.Alw1 nicking enzyme successfully cut a PCR amplicon into which the NtAlw1 nicking site was designed, it did not cut extracted genomic DNA even though the Idh1 gene contains a natural nicking site for NtAlw1.

The sequences below in Table 3 were used to incorporate a nicking site into a PCR amplicon. The Idh1 specific sequences were designed with traditional PCR design software.

In Table 3 below, Design 3 and 4 oligonucleotide sequences for Idh1 amplifications were generated with the Eclipse Design Software 2.3. Underlined sequences represent the nicking site for NtAlw1, the upper case sequence is Idh1 specific, and the 5'-end lower case sequence is non-complementary to the Idh1 target.

TABLE 3

| Seq ID # | Description | Oligonucleotide sequence |
|---|---|---|
| Design 3 | | |
| 22 | Limiting primer-L1 | aataaatcataagggatcAACGTGTTATAGGTTCTGGTACA |
| 23 | Excess primer-E1 | aataaatcataagggatcTGAGCATCGACGCTACGTG |
| 24 | Forward Bumer1 | ATGGAAATTCTCTGGT |
| 25 | Reverse Bumper1 | TGTCACCATGTTCAC |
| Design 4 | | |
| 26 | Limiting primer-L2 | aataaatcataagggatcTGGTGAACATGGTGACACTGAAT |
| 27 | Excess primer-E2 | aataaatcataagggatcGCCCTCAGGACGTTGTTCAAG |
| 28 | Forward Bumer2 | AGCGTCGATGCTCA |
| 29 | Reverse Bumper2 | AATTTGTTCAATTTGCG |

Figure 6:
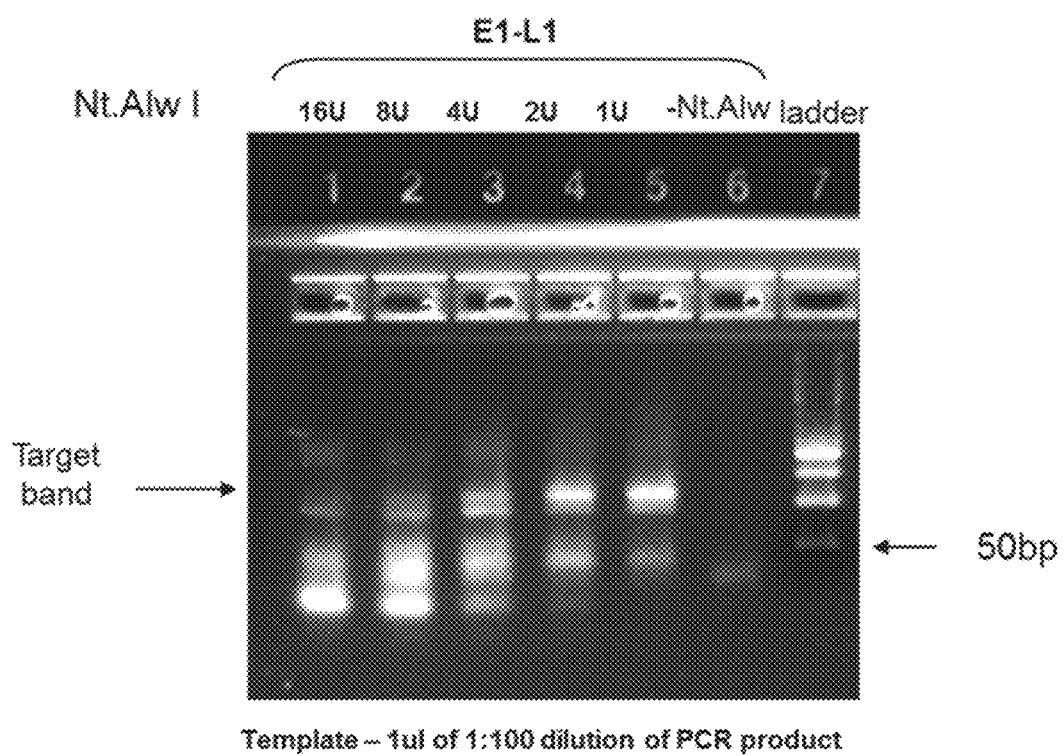
FIG. 6 shows an example of gel analysis of the valuation of Nt.Alw I on PCR Amplified target containing Nt.Alw I cleavage site.

Primers of Design 3 and Design 4 were used to generate PCR amplicons which contain a nicking site for NtAlw1, yielding a convenient target containing a nicking site for NtAlw1. iSDA with the PCR-generated amplicon was analyzed on an agarose gel and the results are shown in FIG. 6.

Example 5

This example illustrates the iSDA bi-plexing of Idh1 and an internal control ("IC"). The IC template contains non-sense, non-specific target DNA fragment in a plasmid vector. Preferably, the control nucleic acid comprises the sequence shown in Table 4 below.

In Table 4 below, oligonucleotide sequences for the amplification of the IC were generated as described above for iSDA amplification. Underlined sequences represent the nicking site for Nt.BbvC1B, the upper case sequence is IC-specific, and the 5'-end lower case sequence is non-complementary to the IC target. The same Idh1 primers, bumper, capture and detection oligonucleotides (Seq. ID #1, 2 4-7. Table 1) were used for the bi-plexing of the Idh1 with the IC. The IC primers, bumpers, capture and detection probes sequences are shown in Table 4.

TABLE 4

| Seq ID # | Description | Oligonucleotide sequence |
|---|---|---|
| 30 | Limiting primer-L1 | ccaatatagtaacagtctcctcagcATTCGCCCTTCTGCACG |
| 31 | Excess primer-E1 | ttcaaaagacccatacttcctcagCCTTCTCATTTTTTCTACCG |
| 32 | Forward Bumper1 | TCGGATCCACTAGTAAC |
| 33 | Reverse Bumper1 | GTGATGGATATCTGCAGAAT |
| 34 | Chimeric pDNA/DNA | [ACATCACA]-Q14-GATCTTGTACCAATGC |
| 35 | Biotinilated probe | CGTGGTCCGTAAAG-biotin TEG |

TABLE 4-continued

Figure 7:
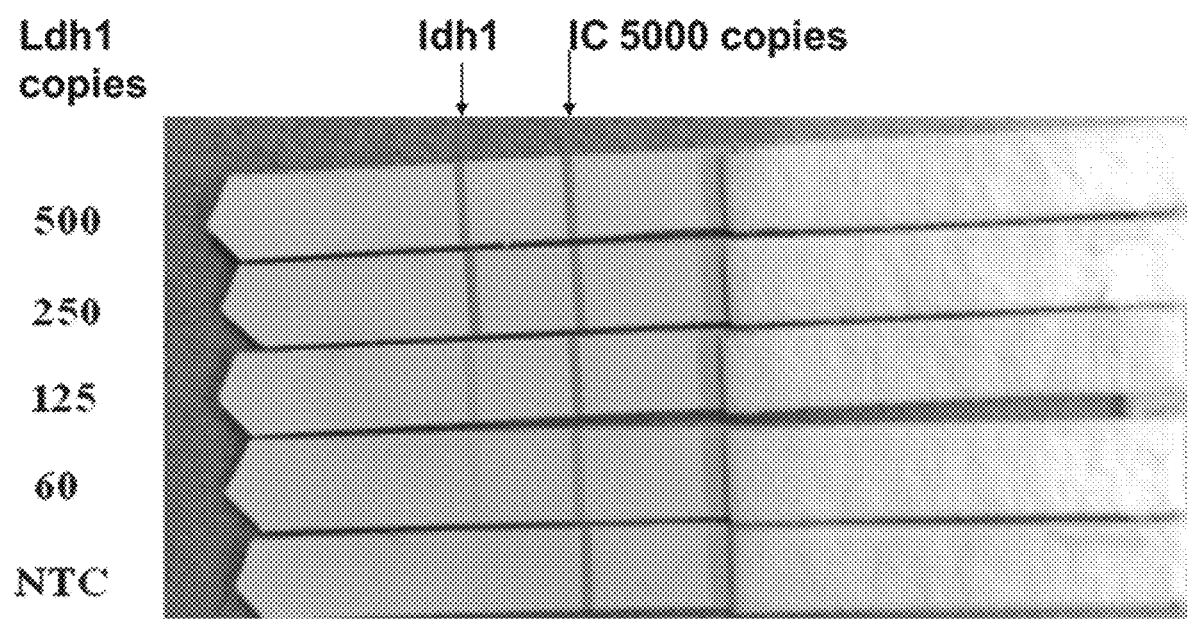
FIG. 7 shows an example of lateral flow detection of iSDA biplex-amplified Idh1 and IC amplicons.

| Seq ID # | Description | Oligonucleotide sequence |
|---|---|---|
| 36 | IC2 | TTTCACACAGGAAACAGCTATGACCATGATTAC GCCAAGCTATTTAGGTGACACTATAGAATACTC AAGCTATGCATCAAGCTTGGTACCGAGCTCGGA TCCACTAGTAACGGCCGCCAGTGTGCTGGAATT CGCCCTTCTGCACGGACCAGTTACTTTACGGAC CACGTACCGCATTGGTACAAGATCTCCGGTAGA AAAAATGAGAAGGGCGAATTCTGCAGATATCCA TCACACTGG | iSDA amplification was performed as described above, except that the concentration for both Idh1 and the IC primers were 250 nM for the limiting primer and 500 nM for excess primer, forward and reverse bumper primers were at 50 nM, the chimeric pDNA-DNA probe and biotinylated probe at 200 nM each. Each target dilution contained 5000 IC2 copies. The amplification reaction was incubated at 48° C. for 30 minutes then it was analyzed by lateral flow analysis as described above. The lateral flow analysis is shown in FIG. 7 indicating for this particular assay a lower detection limit of 60 copies.

Example 6

This example illustrates the probe specific iSDA detection and differentiation of S. aureus (BAA-1556, ATCC) and S. epidermidis (12228. ATCC).

Figure 9:
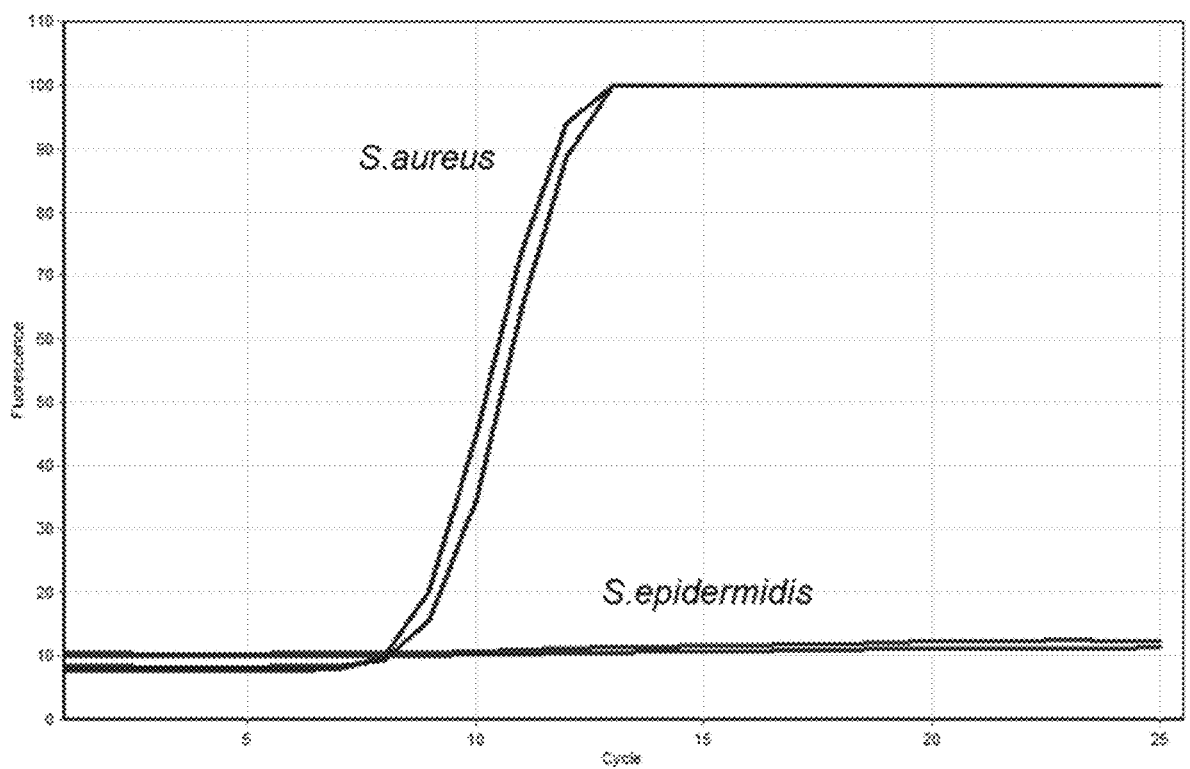
FIG. 9 shows the probe specific iSDA detection and differentiation of Idh1 gene in *S. aureus* and of *S. epidermis*.

Cultures of S. aureus and S. epidermidis ($5 \times 10^8$ cfu/mL) were sonicated for 10 min in the waterbath sonicator (Branson 5510, Bransonic) The crude lysates were assayed for the Idh1 gene according to the method described in Example 1 at a concentration of $5 \times 10^4$ cfu/reaction. Efficient specific detection of the Idh1 gene in S. aureus only is shown in FIG. 9.

Example 7

This example illustrates the iSDA amplification of nucleic acid from the same sample extracted with different methods.

A S. aureus sample was extracted using the following extraction methods:
a) Extraction with chaotropic salts (8M guanidinium HCl or 4M guanidinium thiocyanate), with and without the silica spin column.
Bacterial cells ($5 \times 10^8$ cfu) were extracted according to the procedure described in *Molecular Cloning: a laboratory manual*, (pages 7-19, 7-24). DNA from each extraction was resuspended in 200 µL of the TE buffer and divided into two 100 µL aliquots. One aliquot was set aside for PCR and iSDA analysis, and another one was further purified on QIAmp DNA Mini Kit (Qiagen) spin columns according to the product manual. DNA was eluted in 100 µL of the elution buffer.
b) Phenol/chloroform extraction followed by ethanol precipitation. (Molecular Cloning: a laboratory manual, App.E3-E4).
c) Sonication for 10 min in the waterbath sonicator (Branson 5510. Bransonic).
d) 10% final concentration of Triton X100 incubation at room temperature followed by ethanol precipitation.

Figure 10:
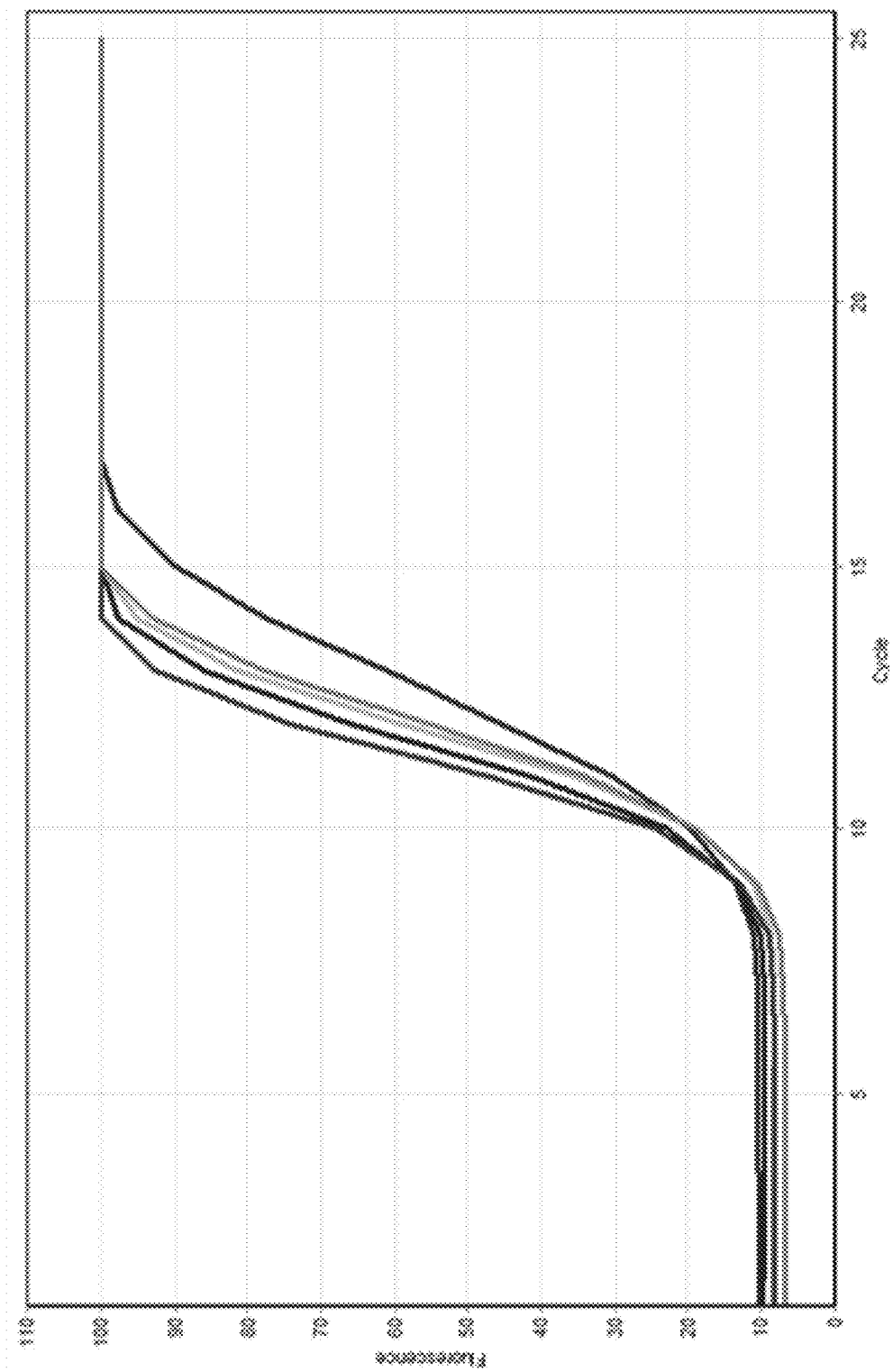
FIG. 10 shows the specific real-time iSDA amplification of *S. aureus* nucleic acid extracted with five different extraction methods.

The concentrations of different non-denatured DNA nucleic acid fractions were normalized at 500 copies/reaction by real-time Idh1 PCR assay (described in U.S. patent application Ser. No. 13/479,557). As shown in FIG. 10, all five extractions gave essentially the same signal result at around cycle 9 (9 min). The NTC showed no amplification and is not shown.

Example 8

This example illustrates the iSDA amplification of the Idh1 gene with primers and probes designed with the current disclosure in comparison with traditional designed primers and probes shown in Table 5.

Using the method described in Example 1, the primers and bumper primers for the Idh1 gene described in Tables 1 and 5 were tested in which both sets of primers had target concentrations ranging from $5 \times 10^3$ to $5 \times 10^5$ target copies/reaction. The amplification reactions were analyzed by agarose gel electrophoresis as shown in FIGS. 11A and B. The arrows in FIGS. 11A and B refer to the amplicon products of amplification. As shown the amplification with the primers of the current disclosure showed substantial amplification at all three concentrations, while the conventional designed primers showed poor amplification FIG. 11A.

TABLE 5

| Seq ID # | Description | Oligonucleotide sequence |
|---|---|---|
| 37 | Limiting primer-L1 | gcattatagtacctgtctcctcagcTGGTGA ACATGGTGACACTGAAT |
| 38 | Excess primer-E1 | ttgaatagtcggttacttcctcagcGCCCTC AGGACGTTGTTCAAG |
| 39 | Forward Bumoer1 | AGCGTCGATGCTCA |
| 40 | Reverse Bumper1 | AATTTGTTCAATTTGCG |

Example 9

This example illustrates the one step RT-iSDA amplification of RSV nucleic acid. RT-iSDA uses the same final concentrations as disclosed for iSDA in [0049], except that 8 U WarmStart Bst Polymerase was substituted for Bst Polymerase, 8 U Nt.BbvCl nicking enzyme was used per 10 µL reaction. In addition the reaction mixture contains 10 U RNA inhibitor (Life Technologies), 0.5 µL Omniscript Reverse Transcriptase (Qiagne), template RNA and 1 µg BSA per 10 µL/reaction. Reaction mixture was followed in real-time for 25 minutes at 49° C. as illustrated in FIG. 12a) and lateral flow detection in FIG. 12b). Primers, bumper primers and probes are shown in Table 6 below. T*=Super T and other abbreviations have been described above. The lateral flow membrane has a test line of pDNA (immobilized by cross-linked polythymidine tail) and a BSA-biotin line as flow control.

TABLE 6

| Seq ID # | Description | Oligonucleotide sequence |
|---|---|---|
| 41 | Limiting primer-L1 | gcattatagtacctgtctcctcagcGAATTCCC TGCATCAATAC |
| 42 | Excess primer-E1 | gcattatggtacctctctcctcagcTA*TGTCA *ATATCT*T*CATC |

TABLE 6-continued

| Seq ID # | Description | Oligonucleotide sequence |
|---|---|---|
| 43 | Forward Bumper1 | AACTAAGGCCAAAGCTTATAC |
| 44 | Reverse Bumper1 | CAGTCAGTAGTAGACCATG |
| 45 | Chimeric pDNA/DNA | [TTTTTTTC]-(Q14)-CTACAAATTATCACTTTGA |
| 46 | Biotinilated probe | TA*ATCGCATATTAACAG-biotin TEG |
| 47 | FAM probe | MGB-FAM-TAATCGCATAT*T*AACAG-EDQ |

Example 10

This example illustrates the iSDA amplification of native and denatured *P. falciparum* genomic DNA. Primers and probes were designed using mitochondrial DNA (Polley et. al., J. Clin. Microbiol, 48:2866-2871 (2010)) as a target and is shown in Table 7 below. Extraction from *Plasmodium falciparum*, strain NF54 and iSDA amplification were performed as described above. FIG. 13A shows identical real-time iSDA amplification for native and denature DNA at 95° C. for 5 minutes. FIG. 13B shows the amplification of native DNA at 100 and 1000 copies.

TABLE 7

| Seq ID # | Description | Oligonucleotide sequence |
|---|---|---|
| 48 | Limiting primer-L1 | gaatagacccatacatcctcagcGACTTGAGTAATGATAAATTGATAG |
| 49 | Excess primer-E1 | gaatagacccatacatcctcagcGACTTGAGTAATGATAAATTGATAG |
| 50 | Forward Bumper1 | CCA*CTTGCTTATAACTGTATG |
| 51 | Reverse Bumper1 | GTTTCCA*TAGAAACCTTCAT |
| 52 | FAM probe | MGB-FAM-ATTGATTCCGTTTTGAC-EDQ |

Example 11

This example, and Example 20 below, illustrate the calculation of estimated fraction of dissociated bases within subregions of the Influenza A virus segment 7 matrix protein 2 (M2) and matrix protein 1 (M1) genes (GenBank: MF599466.1). Example 20 shows the calculation in greater detail. For each subregion (oligo lengths 5 to 41) over the entire sequence, melt curves were predicted using nearest neighbor thermodynamic parameters (SantaLucia 1998) and salt corrections were made to entropy values (see Owczarzy et al, Biochemistry 2008, 47, 5336-5353). Owczarzy developed equations that obtain corrected Tm for non-standard salt conditions (where 1 M monovalent cation is standard), as shown below:

$$\frac{1}{Tm(\text{Na})} = \frac{1}{Tm(1M\text{Na})} + (4.29 * fGC - 3.95 * 10^{-5} * \ln[\text{Na}] + 9.4 * 10^{-6} * (\ln[\text{Na}])^2$$

$$\frac{1}{Tm(\text{Mg})} = \frac{1}{Tm(1M\text{Na})} + a + b * \ln[\text{Mg}] + fGC * (c + d * \ln[\text{Mg}]) + \frac{1}{2*(bp-1)} * [e * f * \ln[\text{Mg}] + g * (\ln[\text{Mg}])^2]$$

In the above two equations, the variables are:
Tm(Na) is the predicted Tm, in Kelvins, of the duplex in an environment that may be a mixture of monovalent and divalent cations;
Tm(Mg) is the predicted Tm, in Kelvins, of the duplex in an environment that may be a mixture of monovalent and divalent cations;
Tm(1 M Na) is the predicted Tm, in Kelvins, of the duplex in a standard solution containing 1 M monovalent cation, calculated by summing standard nearest neighbor enthalpy and entropy terms;
fGC is the fraction of duplex which is either guanidine or cytidine;
bp is the length of the duplex;
[Mg] represents the concentration of divalent cations;
[Na] represents the concentration of divalent cations;

$b = -9.11e-6$ K$^{-1}$;

$c = 6.26e-5$ K$^{-1}$;

$e = -4.82e-4$ K$^{-1}$;

$f = 5.25e-4$ K$^{-1}$; and where a, d, g in the second equation vary with the ratio, r, of divalent cation ([Mg]) versus monovalent cation ([Na]) where:

$$r = \frac{\sqrt{[\text{Mg}]}}{[\text{Na}]}$$

When [Na] is zero or r>6.0, the second equation is used with parameters:

$a = 3.92e-5$ K$^{-1}$ $d = 1.42e-5$ K$^{-1}$ $g = 8.31e-5$ K$^{-1}$.

When r<0.22, the monovalent salt contribution dominates and the first equation (1/Tm Na) is used.
When r>0.22 and r<6.0, the second equation is used with parameters:

$a = 3.92*10^{-5}*(0.843-0.352\sqrt{[\text{Na}]}*\ln[\text{Na}])$ $d = 1.42*10^{-5}*[1.279-4.03*10^{-3}*\ln[\text{Na}]-8.03*10^{-3}*(\ln[\text{Na}])^2]$ $g = 8.31*10^{-5}*[0.486-0.258*\ln[\text{Na}]+5.25*10^{-3}*(\ln[\text{Na}])^3]$ The analysis temperature was assessed by the predicted sigmoidal melt curve to calculate the fraction dissociated. The average of all subregions' fractions dissociated was calculated, as shown in greater detail in Example 20, to establish the final estimated fraction dissociated values that are shown in FIG. 14.

Example 12

Figure 15:
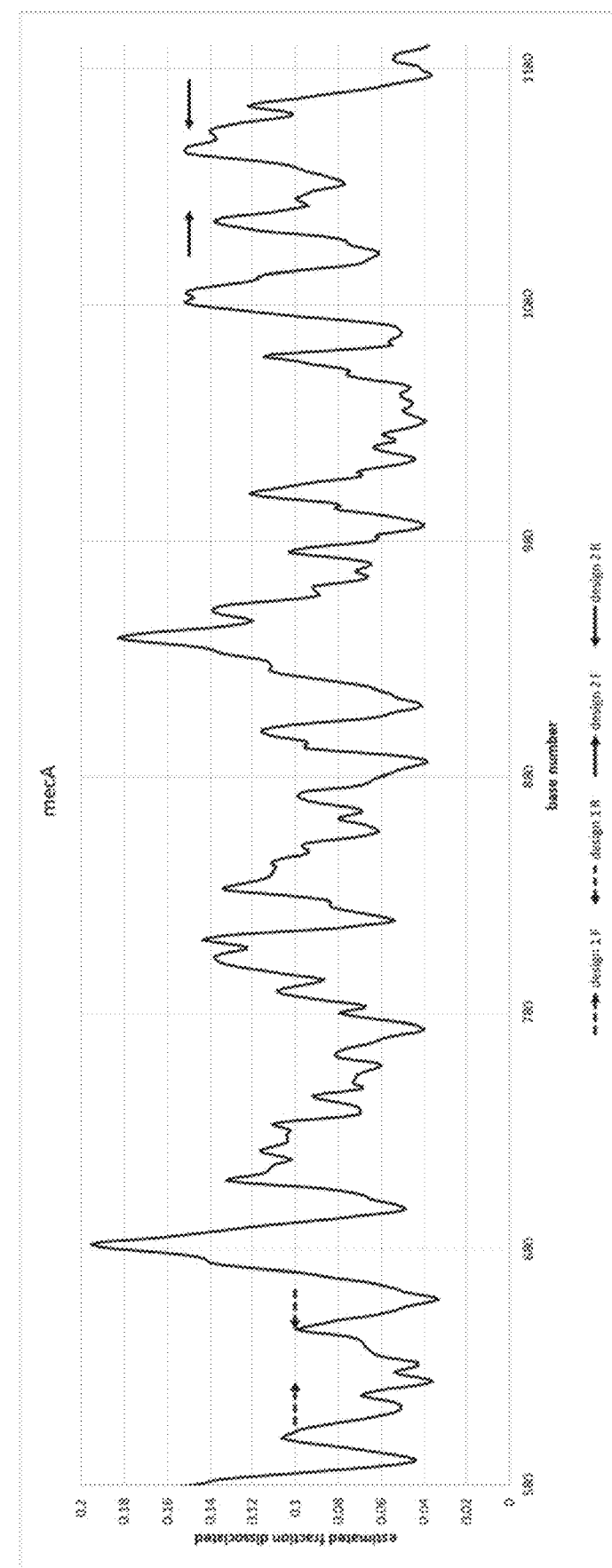
FIG. 15 shows estimated fractions of dissociated bases within a target mecA sequence and placement of primers designed for iSDA amplification.

This example analyzes the *Staphylococcus aureus* mecA assay designs described in Example 2 above (design 1 and design 2), with the results shown in FIG. 4. In particular, the estimated fraction of bases dissociated within sub-regions of the target gene was calculated using the same process described above in Example 11. The results are shown in FIG. 15. The primers of design 1 and 2 were designed to hybridize to portions of the target gene. As shown, the primers of design 2 hybridize to a gene region where the estimated fraction of dissociation is about 50% greater than that of design 1. Accordingly, the assay design 2 from Example 2 (and FIG. 4) works better than that of design 1. Design 1 shows a Ct of about 15 at 50 copies while design 2 at the same concentration shows a Ct of 8. This can be explained by the fact that primers from design 2 are designed to hybridize to regions having a higher estimated fraction of dissociation.

Example 13

Figure 16:
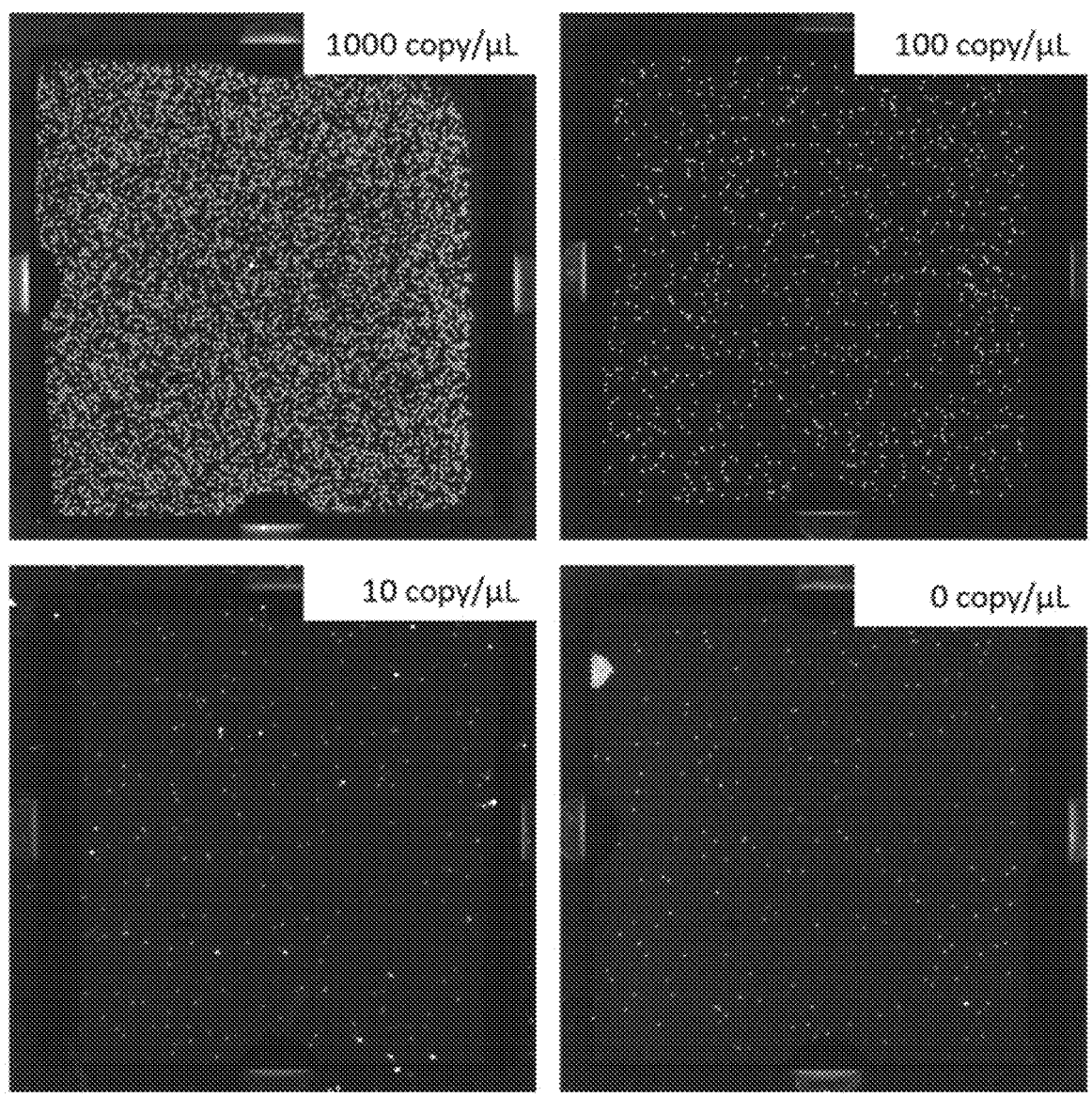
FIG. 16 shows images of chips obtained from digital PCR in iSDA of Idh1 target gene using different target concentrations.

This example illustrates the performance of iSDA amplification of the ldh1 *Staphylococcus aureus* gene in digital format for target quantitation. The reaction formulation of Example 1, which targeted ldh, was repeated using 1000, 100, 10, and 0 copies/μL and reaction mixes were loaded on an Applied Biosystems QuantStudio™ 3D Digital PCR Chip v2. Isothermal amplification of the digital chips was performed on the Applied Biosystems ProFlex PCR system at 50° C. for 30 minutes, and chips were imaged using Applied Biosystems QuantStudio 3D chip imager. Table 8 below shows the quantitation result of ldh digital iSDA. FIG. 16 shows corrected images of the chip imager.

TABLE 8

Digital iSDA of ldh target, Quantitation by Instrument

| Copies/μL Input | Copies/μL Result | CI Copies/μL |
|---|---|---|
| 1000 | 628.84 | 613.7--644.35 |
| 100 | 76.161 | 71.538--81.084 |
| 10 | 13.1 | 11.246--15.259 |
| 0 | 12.127 | 10.415--14.119 |

Example 14

Figure 17:
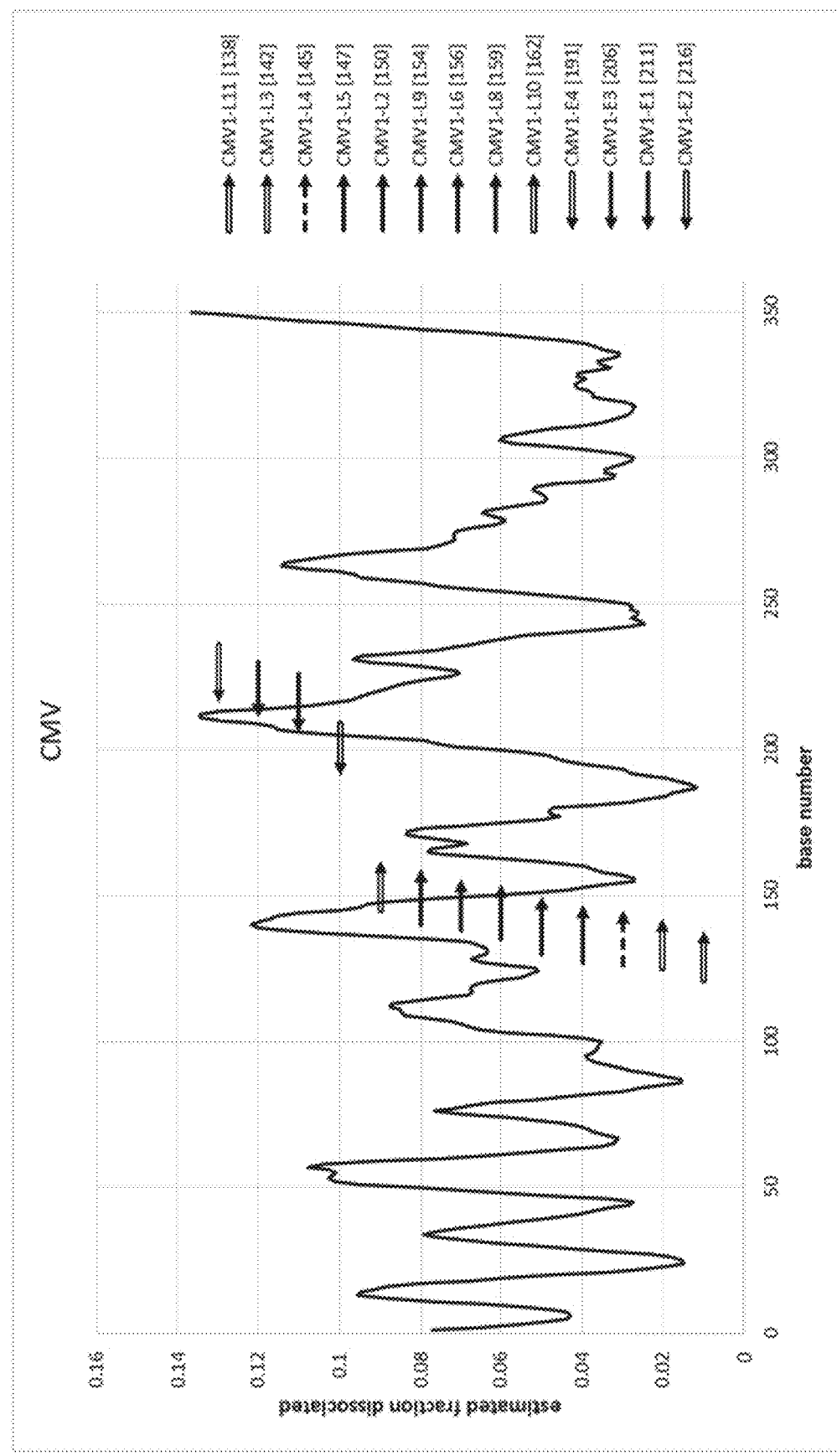
FIG. 17 shows estimated fractions of dissociated bases within a target CMV sequence and placement of primers designed for iSDA amplification.

This example illustrates the prospective design of a CMV iSDA assay by estimating fraction dissociated DNA within sub-regions of this gene, followed by primer design in favorable breathing regions. The primer sequences evaluated are shown in Table 9 below, where the nicking site is underlined, the stabilizing flap sequence is shown in lower case, A* is Super A. T* is Super T (U.S. Pat. No. 7,045,610) and the position of the 3'-end is indicated in FIG. 17. Solid arrows in FIG. 17 indicate good amplification by the particular primer also shown with a plus in Table 9. Empty arrows indicate no amplification.

TABLE 9

| SEQ ID NO: | Primer Name | Performance | 3'-end position | Oligonucleotide Sequence |
|---|---|---|---|---|
| 53 | CMV 1 L11 | + | 138 | gcaatatagaaccagtat<u>CCTCAGC</u>GTAGAGGAGGATAACAAC |
| 54 | CMV 1 L3 | + | 142 | gcaatatagaaccagtat<u>CCTCAGC</u>AGGAGGATAACAACACAT |
| 55 | CMV 1 L4 | | 145 | gcaatatagaaccagtat<u>CCTCAGC</u>GGAGGATAACAACACATATA |
| 56 | CMV 1 L5 | + | 147 | gcaatatagaaccagtat<u>CCTCAGC</u>GAGGATAACAACACAT*ATAAG |
| 57 | CMV 1 L2 | + | 150 | gcaatatagaaccagtat<u>CCTCAGC</u>GATAACAACA*CATAT*AAGTAT |
| 58 | CMV L9 | + | 154 | gcaatatagaaccagtat<u>CCTCAGC</u>AACACAT*ATAAGT*ATCCGT |
| 59 | CMV 1 L6 | + | 156 | gcaatatagaaccagtat<u>CCTCAG</u> CACATATAAGTATCCGTCC |
| 60 | CMV 1 L8 | + | 159 | gcaatatagaaccagtat<u>CCTCAGC</u>ATATAAGTATCCGTCCTCC |
| 61 | CMV 1 L10 | | 162 | gcaatatagaaccagtat<u>CCTCAGC</u>AAGTATCCGTCCTCCTGA |
| 62 | CMV 1 E4 | | 191 | gcaatatagaaccagtat<u>CCTCAGC</u>GATTAACTCTTGCATGTGA |
| 63 | CMV 1 E3 | + | 206 | gcaatatagaaccagtat<u>CCTCAGC</u>ATGTCAGATAGAGTA*AAGATT |
| 64 | CMV 1 E2 | | 211 | gcaatatagaaccagtat<u>CCTCAGC</u>TTACTTGTGTATGTCAGATAG |

TABLE 9-continued

| SEQ ID NO: | Primer Name | Performance | 3'-end position | Oligonucleotide Sequence |
|---|---|---|---|---|
| 65 | CMV 1 E1 | + | 216 | gcaatatagaaccagtat<u>CCTCAGC</u>GTGTATGT*CAGATAGAGTAA |

Example 15

Figure 18:
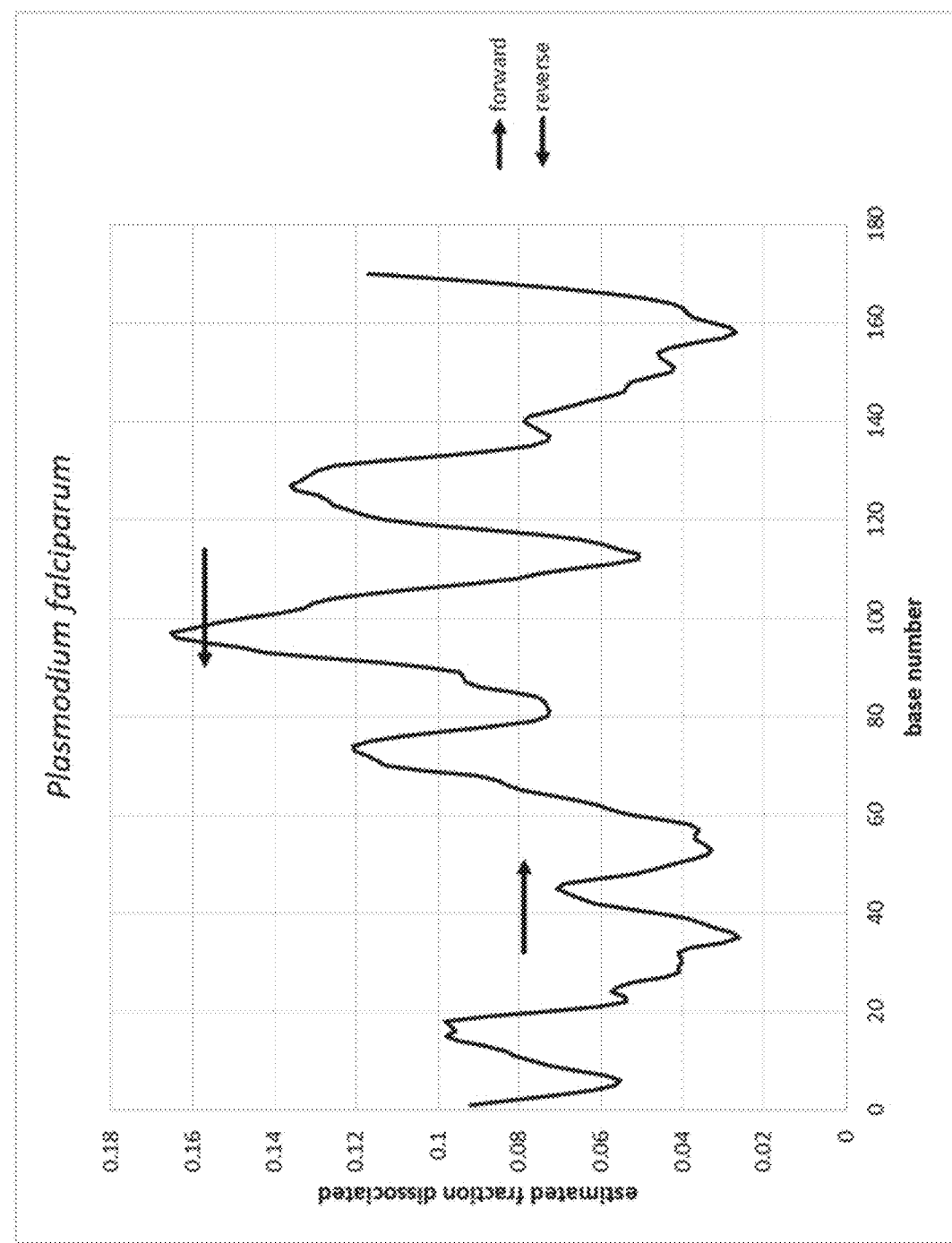
FIG. 18 estimated fractions of dissociated bases within a target mecA sequence and placement of primers designed for iSDA amplification.

This example analyzes the *Plasmodium falciparum* assay designs described in Example 10, with results shown in FIG. 13. The estimated fraction of bases dissociated within sub-regions of the target gene was calculated. The results are shown in FIG. 18. Each primer used in the assay design hybridizes within the "breathing profile" of the gene, or those regions where there is a higher estimated fraction of dissociated bases. As shown, the reverse primer hybridizes to the gene region where the estimated fraction of dissociation is particularly favorable for breathing.

Example 16

Figure 12:
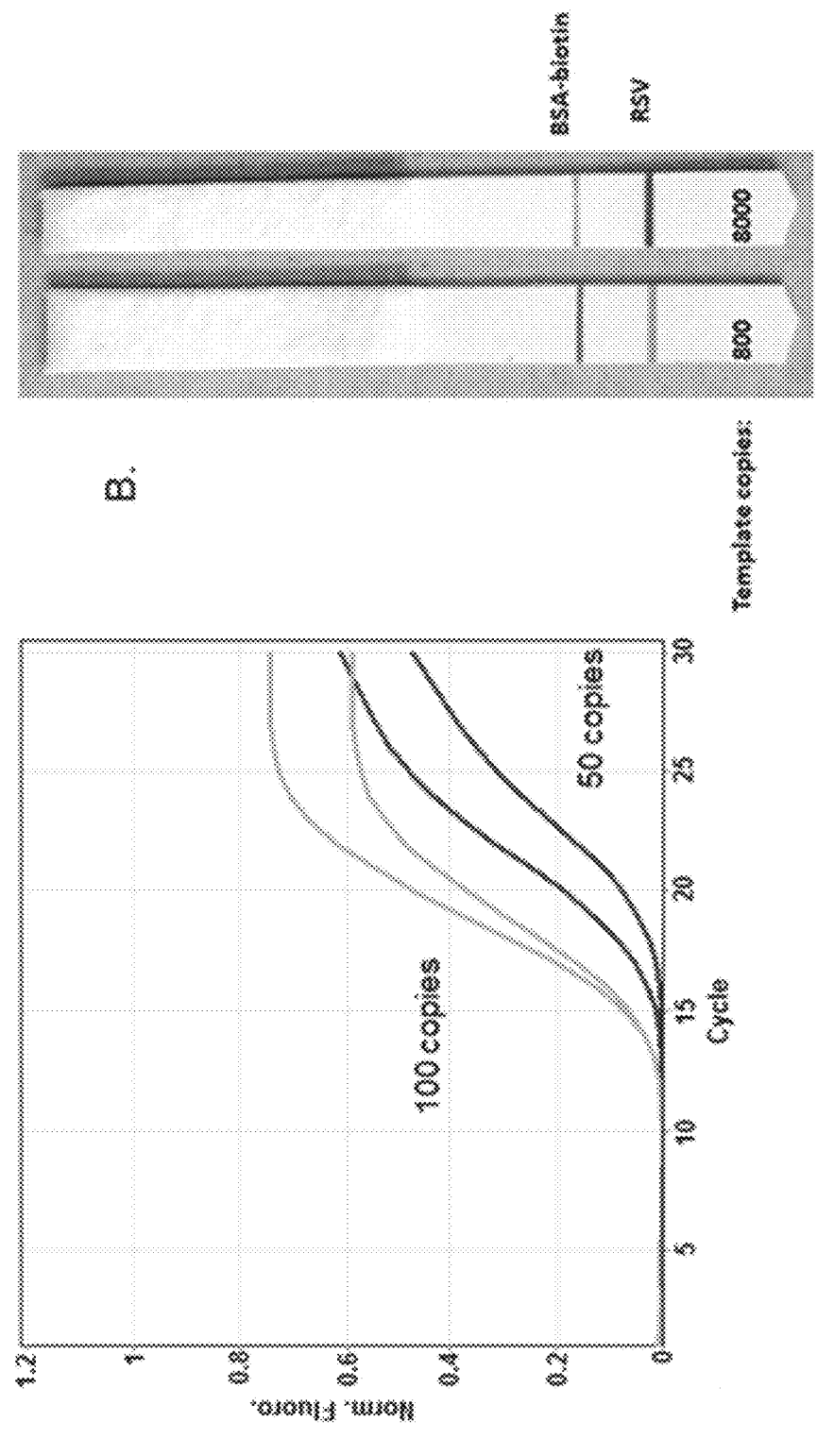
FIG. 12 shows the specific reverse transcriptase-iSDA (RT-iSDA) amplification of Respiratory syncytial virus (RSV) extracted RNA nucleic acid using both real-time fluorescence detection and post-amplification lateral flow detection.
Figure 19:
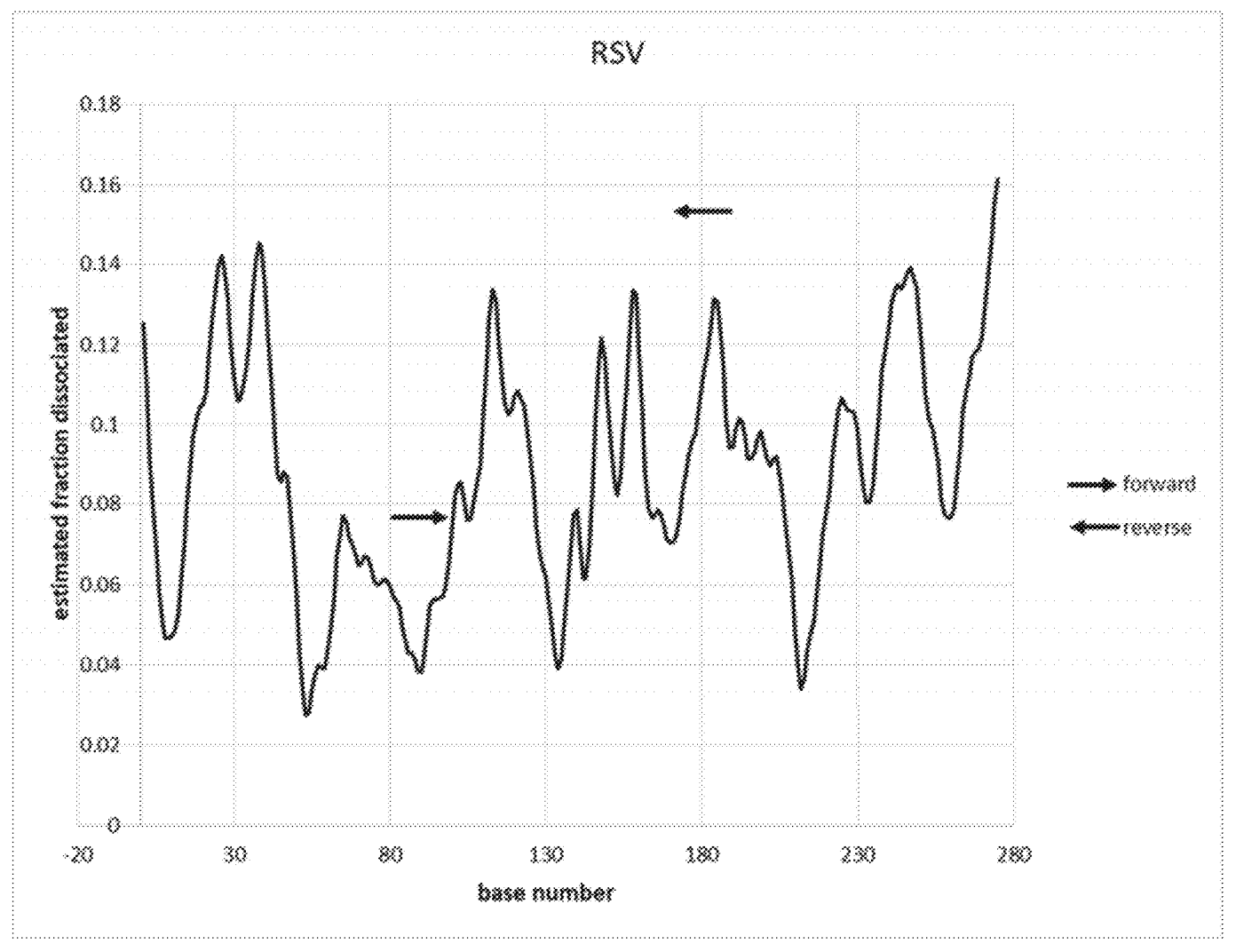

This example analyzes the RSV assay designs described in Example 9, with the results shown in FIG. 12. The estimated fraction of dissociated bases within sub-regions of the target gene was calculated. The results are shown in FIG. 19, which also identifies where the primers were designed to hybridize. As shown, the reverse primer hybridizes to a gene region where the estimated fraction of dissociation is particularly favorable for breathing.

Example 17

Figure 20:
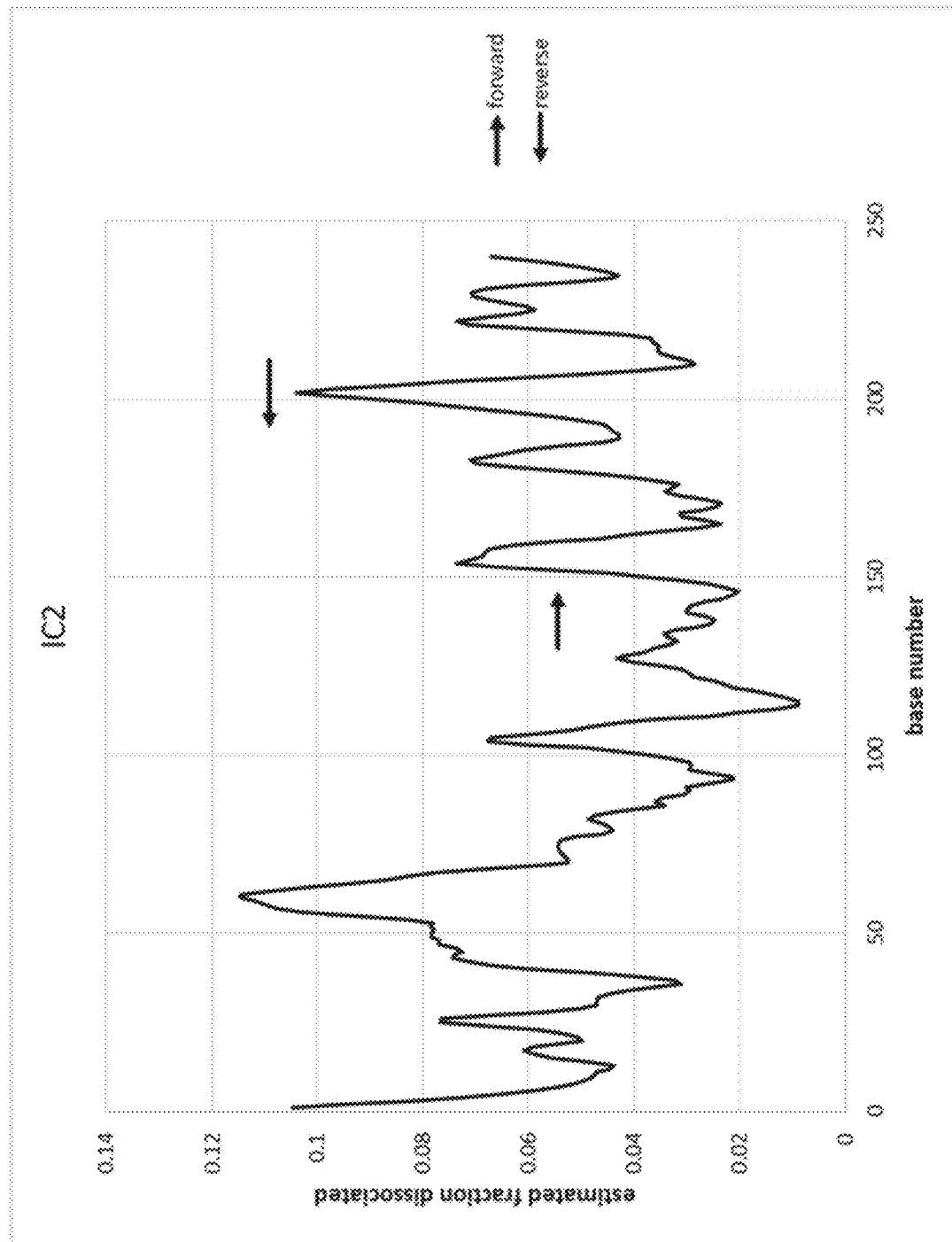
FIG. 20 shows estimated fractions of dissociated bases within a target IC2 sequence and placement of primers designed for iSDA amplification.

This example analyzes the IC2 assay designs described in Example 5 and Table 4, with particular attention to SEQ ID NO: 36. The estimated fraction of dissociated bases within sub-regions of this sequence was calculated. The results are shown in FIG. 20, which identifies where the designed primers hybridize to SEQ ID NO: 36. As shown, the reverse primer hybridizes to a gene region where the estimated fraction of dissociation is particularly favorable for breathing.

Example 18

Figure 21A:
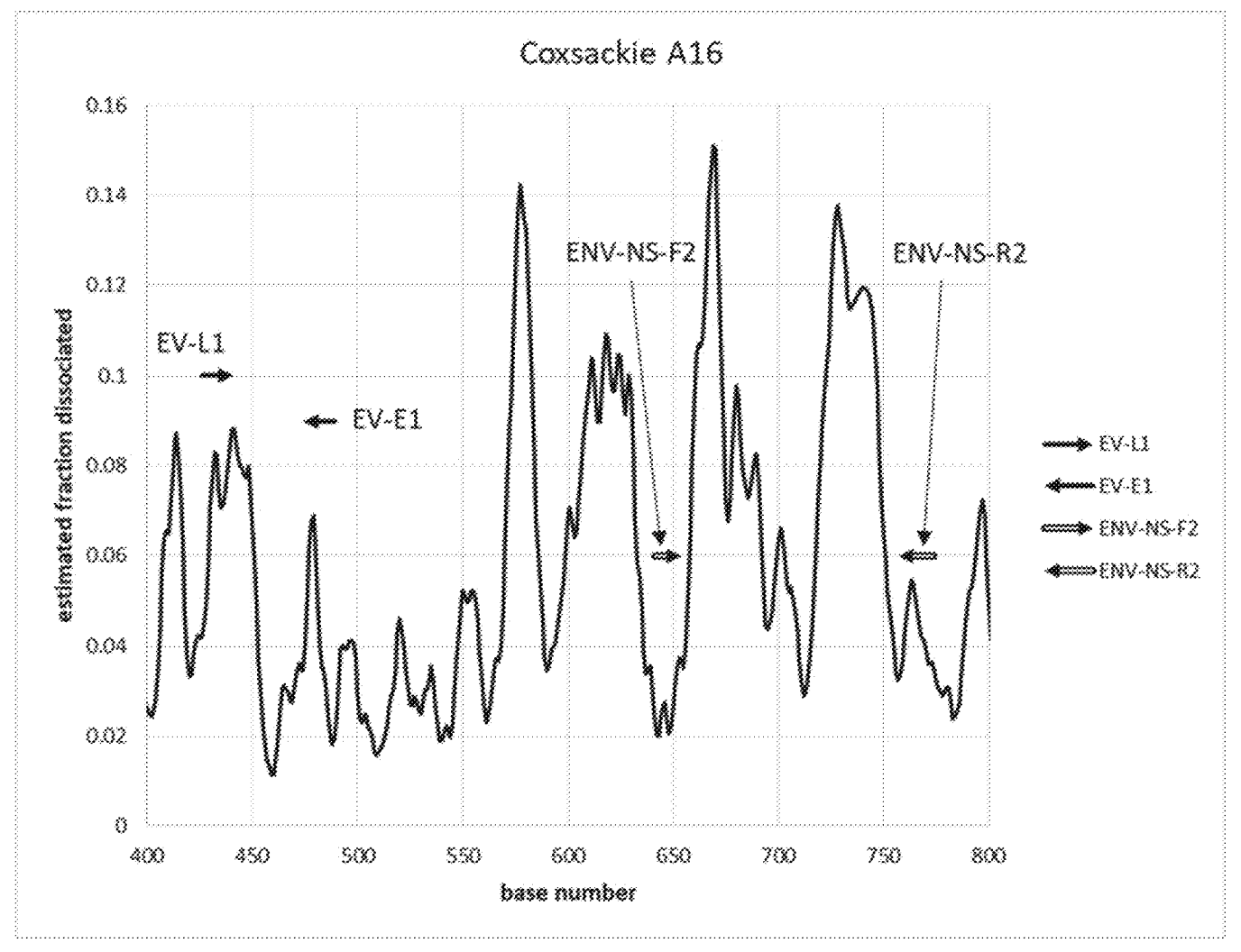
Figure 21B:
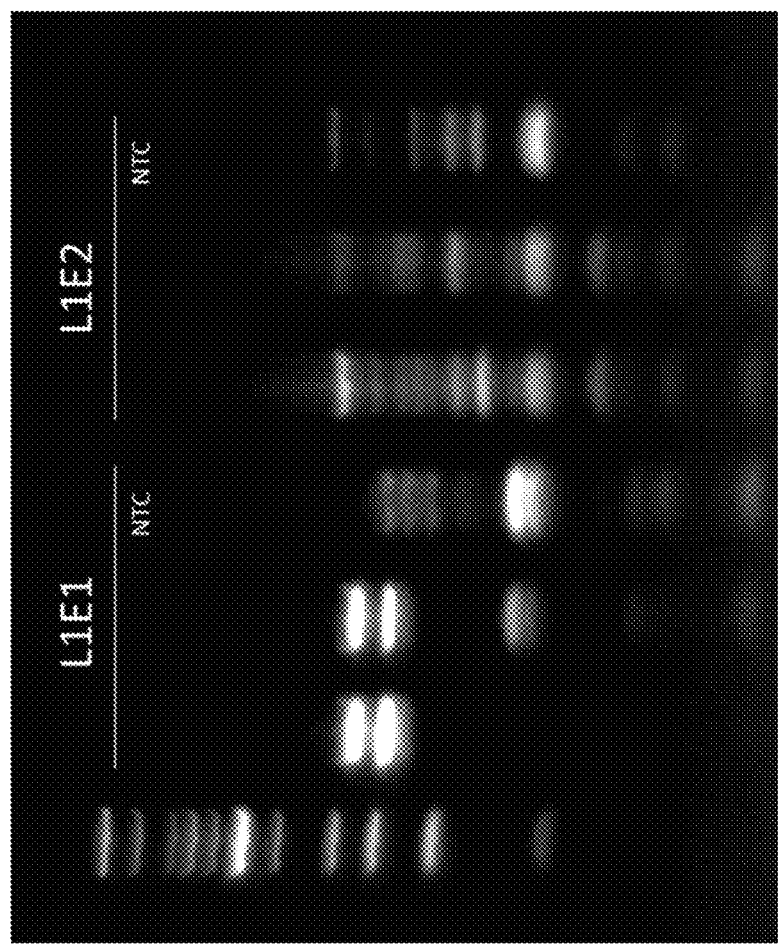
FIG. 21B shows an image of a gel indicating detection results for different primers designed for iSDA amplification of a target enterovirus sequence.

This example illustrates a primer design based on first calculating the estimated fraction of dissociated bases in an enterovirus target. In this example, both presumed favorable and unfavorable regions were targeted in two different systems with sequences shown in Table 10 below. The favorable design includes SEQ ID NOs 66 and 67, while the unfavorable design includes SEQ ID NOs 68 and 69. FIG. 21A shows the profile of estimated fractions of dissociated bases, or breathing profile, of the target sequence with primer locations identified. FIG. 21B shows the gel image, where primers lying in the breathing profile troughs (SEQ ID NOs: 68 and 69) show non-specific side products, while primers in regions with a greater estimated fraction of dissociated bases (SEQ ID NOs: 66 and 67) show more specific products. Example 20 provides a more detailed calculation of the estimated fraction of dissociated bases in an enterovirus target.

TABLE 10

| SEQ ID NO: | Primer Name | 3'-end position | Oligonucleotide Sequence |
|---|---|---|---|
| 66 | EV-L1 | 441 | gcaatatagaaccagta<u>CCTCAGC</u>GAAGAGTCTATTGAGC |
| 67 | EV-E1 | 474 | gcaatatagaaccagta<u>CCTCAGC</u>TCCGCAGTTAGGATTA |
| 68 | ENV-NS-F2 | 654 | gcaatatagaaccagta<u>CCTCAGC</u>CATCCGGTGTGCAA |
| 69 | ENV-NS-R2 | 757 | gcaatatagaaccagta CCTCAGCTTGGGTTGAGACTTGTGA |

Example 19

Figure 22:
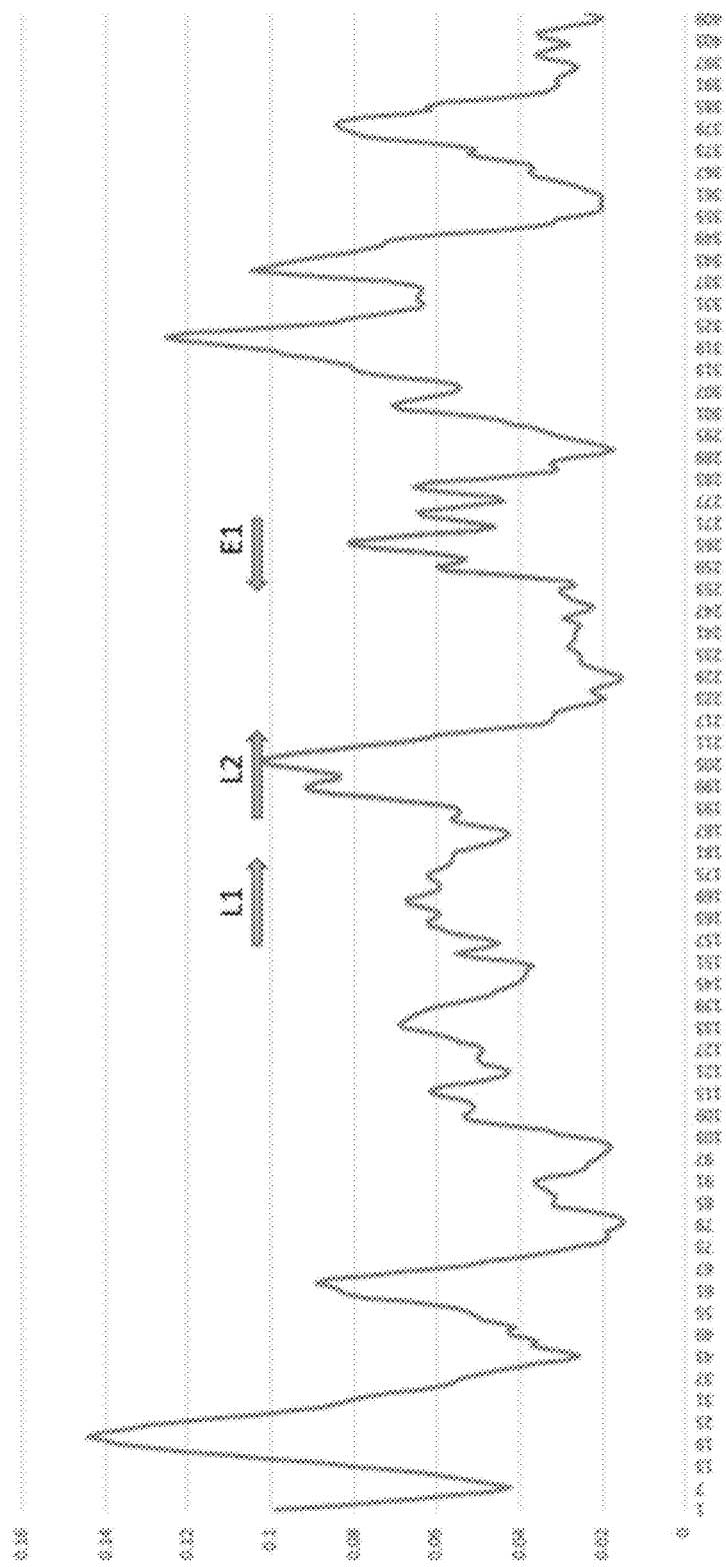
FIG. 22 shows estimated fractions of dissociated bases within a target influenza A H3N1 sequence and placement of primers designed for iSDA amplification.
Figure 23A:
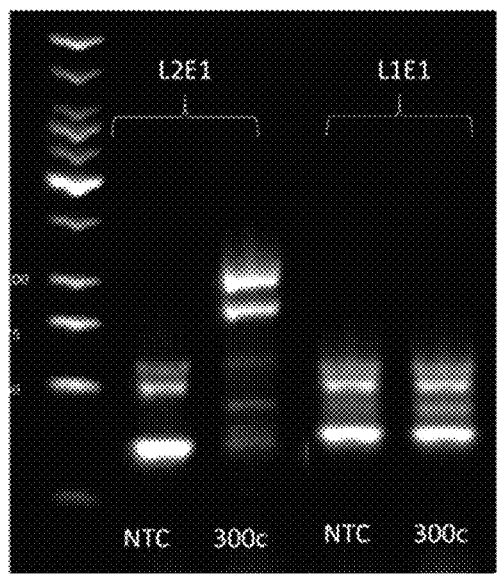
FIG. 23A shows a gel image comparing amplification results from a set of primers in a low dissociation region and primers in a region of higher dissociated bases (L1E1) and a set of primers both in regions with a greater estimated fraction of dissociated bases (L2E1).
Figure 23B:
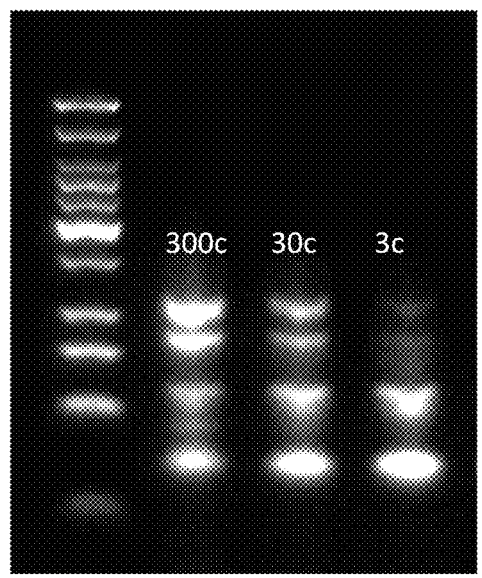
FIG. 23B shows a gel image of titration of influenza A virus subtype H3N1 from 3 to 300 copies/reaction.
Figure 23C:
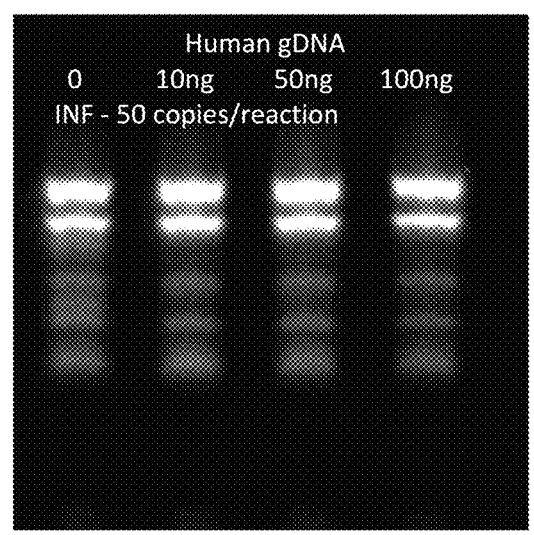
FIG. 23C shows a gel image of a titration of influenza A virus subtype H3N1 at 50 copies/reaction in the presences of 10 to 100 ng of human genomic DNA.

This example illustrates a primer design based on first calculating the estimated fraction of dissociated bases in an influenza A virus subtype H3N2 target (>A/Bethesda/P0054/2015|KY487749|01/13/2015|USA|Maryland|H3N2), shown in FIG. 22. In this example, both presumed favorable and unfavorable regions were targeted in two different systems with sequences shown in Table 11 below. The favorable design includes the primer combination SEQ ID NOs 71 and 72, while the unfavorable design includes the primer combination SEQ ID NOs 70 and 72. FIG. 22 shows the profile of estimated fractions of dissociated bases, or breathing profile, of the target sequence with primer locations identified. FIG. 23A shows the gel image, where primers lying in the breathing profile with one region of lower dissociated bases (SEQ ID NO: 70) combined with a region of higher dissociated bases (SEQ ID NO: 72) show non-specific side products, while primers in regions with a greater estimated fraction of dissociated bases (SEQ ID NOs: 71 and 72) show more specific products. FIG. 23B shows the gel image of a titration of influenza A virus subtype H3N1 from 3 to 300 copies/reaction. FIG. 23C shows the gel image of a titration of influenza A virus subtype H3N2 at 50 copies/reaction in the presences of 10 to 100 ng of human genomic DNA, illustrating the robustness of the amplification.

TABLE 11

| Seq ID # | Description | Oligonucleotide sequence |
|---|---|---|
| 70 | Limiting primer-L1 | gcaatatagaaccagtat<u>CCTCAGC</u>AATGGC TAAAGACAAGAC |

TABLE 11-continued

| Seq ID # | Description | Oligonucleotide sequence |
|---|---|---|
| 71 | Limiting primer-L2 | gcaatatagaaccagtat<u>CCTCAGC</u>AAGGGA ATTTTAGGGT*TTG |
| 72 | Excess primer-E1 | gcaatatagaaccagtat<u>CCTCAGC</u>ATTTTG GA*TAAAGCGT |
| 73 | Forward Bumper1 | CAGAGATCTTGAGGCTCTCA |
| 74 | Reverse Bumper1 | CAGTTTAACTGCTTTGTCCATG |
| 75 | FAM1 probe | TCACCGTGCCCAGTG |
| 76 | FAM2 probe | GACTGCAGCGTAGAC |

Example 20

This example provides a more detailed explanation of how to calculate a fraction of dissociated bases. Example SEQ ID NO:77 below represents an enterovirus (Cocksackie A16) region used in the exemplary calculation:

(SEQ ID NO: 77)
TTAAAACAGCCTGTGGGTTGTACCCACCCACAGGGCCCACTGGGCGCTA

GCACTCTGATTCTACGGAATCCTTGTGCGCCTGTTTTATGTCCCTTCCC

CCAATCAGTAACTTAGAAGCATTGCACCTCTTTCGACCGTTAGCAGGCG

TGGCGCACCAGCCATGTCTTGGTCAAGCACTTCTGTTTCCCCGGACCGA

GTATCAATAGACTGCTCACGCGGTTGAGGGAGAAAACGTCCGTTACCCG

GCTAACTACTTCGAGAAGCCTAGTAGCACCATGAAAGTTGCAGAGTGTT

TCGCTCAGCACTTCCCCCGTGTAGATCAGGTCGATGAGTCACTGCGATC

CCCACGGGCGACCGTGGCAGTGGCTGCGTTGGCGGCCTGCCTGTGGGGT

AACCCACAGGACGCTCTAATATGGACATGGTGCAAAGAGTCTATTGAGC

TAGTTAGTAGTCCTCCGGCCCCTGAATGCGGCTAATCCTAACTGCGGAG

CACATACCCTCGACCCAGGGGCAGTGTGTCGTAACGGGCAACTCTGCA

GCGGAACCGACTACTTTGGGTGTCCGTGTTTCCTTTTATTCTTATACTG

GCTGCTTATGGTGACAATTGAAAGATTGTTACCATATAGCTATTGGATT

GGCCATCCGGTGTGCAACAGAGCTATTATTTACCTATTTGTTGGGTATA

TACCACTCACATCCAGAAAACCCTCGACACACTAGTATACATTCTTTA

CTTGAATTCTAGAAAATGGGGTCACAAGTCTCAACCCAACGATCGGGTT

CCCACGAAAATTCGAACTCAGCATCAGAAGGA

Parameters used in the calculation are shown in Table 12 below.

TABLE 12

| Calculation Parameter | Value | Notes |
|---|---|---|
| temperature | 50 | temperature, in ° C., of the system |
| subset min | 2 | how many bases (on each side) to sum, minimum; minimum is 1 |
| subset max | 20 | how many bases (on each side) to sum, maximum-- for long range effects; enter "0" for full-length |

TABLE 12-continued

| Calculation Parameter | Value | Notes |
|---|---|---|
| weighting slope | 0 | from subset min to subset max, how to weight the interstitial results |
| tails code | 1 | how to process sequence tails; 0 = none, 1 = polyT, 2 = polyG, 3 = circular |
| monovalent salt conc | 100 | monovalent cation (eg, NaCl + half buffer concentrations), in mM |
| divalent salt conc | 5 | divalent cation (e.g., MgCl$_2$), in mM |
| weight power | 0 | exponential long-range Interaction effect |

The calculation process can be explained in this example as follows:
(1) Add 20 thymidine bases to the beginning of the sequence and end of the sequence
  (a) This relates to the "tails code" in Table 12 above. This allows calculations of each sequence end more easily— the program is tunable for circular, poly-T, poly-G, etc.
(2) The first base in SEQ ID NO:77, T, is then analyzed by construction of subsequences centered about the first base.

(a)  2 bases before, 2 bases after:     TTTTT (b)  3 bases before, 3 bases after:     TTTTTTA (c) Continue adding until 20 bases before, 20 bases after:

TTTTTTTTTTTTTTTTTTTTTAAAACAGCCTGTGGGTTGT (3) Each subsequence in Step 2 is then analyzed for enthalpy and entropy using a dimer table (see Table 13 below for Unified Enthalpy and Entropy Parameters; SantaLucia 1998).
  (a) Sequence in 2a:

$dH=TT_{dH}+TT_{dH}+TT_{dH}+TT_{dH}=4*-7.9=-31.6$ kcal/mol     i.

$dS=TT_{dS}+TT_{dS}+TT_{dS}+TT_{dS}=4*-22.2=-88.8$ cal/K·mol     ii.

(b) Sequence in 2b:

$dH=TT_{dH}+TT_{dH}+TT_{dH}+TT_{dH}+TT_{dH}+TA_{dH}=-7.9+-7.9+-7.9+-7.9+-7.9+-7.2$     i.

$dS=TT_{dS}+TT_{dS}+TT_{dS}+TT_{dS}+TT_{dS}+TA_{dS}=-22.2+-22.2+-22.2+-22.2+-22.2+-21.3$     ii.

(c) Sequence in 2c:

$dH=-321.7$ kcal/mol     i.

$dS=-882.8$ cal/K·mol$=-0.8828$ kcal/K·mol     ii.

(4) Calculate Tm for each subsequence around each base.
  (a) Calculate Tm at standard conditions (1 M Na$^+$)

Enthalpy and entropy dimer values at 1 M Na$^+$     i.

$Tm=dH/(dS+R*\ln(C_T))$     ii.

1. R=gas constant
  2. $C_T$ set to arbitrary constant of 2 μM
  (b) Calculate Tm at specified salt condition $1/Tm=1/Tm_{1\,N\,Na+}$+salt correction—see Example 11     i.

(c) Sequence 2a Tm at standard conditions: 268.64 K=−4.51° C.

Salt correction leads to −3.03° C.     i.

(5) Simulate the melt curve shape and estimate the fraction dissociated based on the curve.
  (a) Shape is sigmoidal with time of max growth, M, at calculated Tm
  (b) Calculate B, the "growth rate," a parameter describing the "sharpness" of a sigmoid curve
    i. B is, in theory, directly related to dH
    ii. B=dH/c
      1. Constant c was empirically calculated from model systems to be 365.608, as an average
  (c) Use standard sigmoid function to estimate the fraction dissociated, y, at temperature x as set in the parameter table $$y(x) = 1 - \frac{1}{1 - e^{-B(x-M)}}$$

Figure 24A:
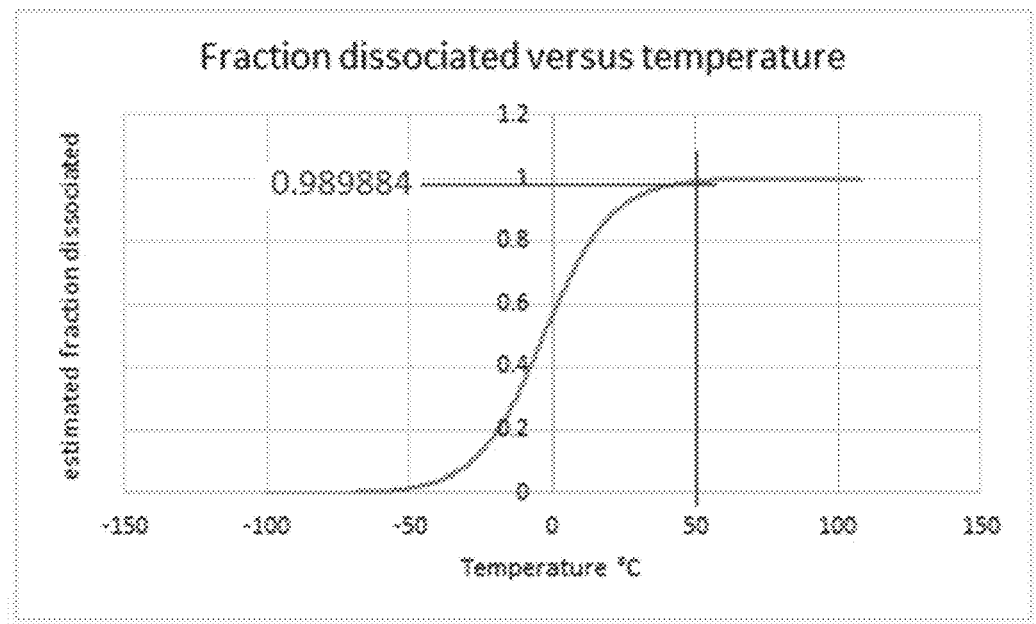
FIG. 24A shows a plot of estimated fraction of dissociated bases versus temperature for an exemplary subsequence.
Figure 24B:
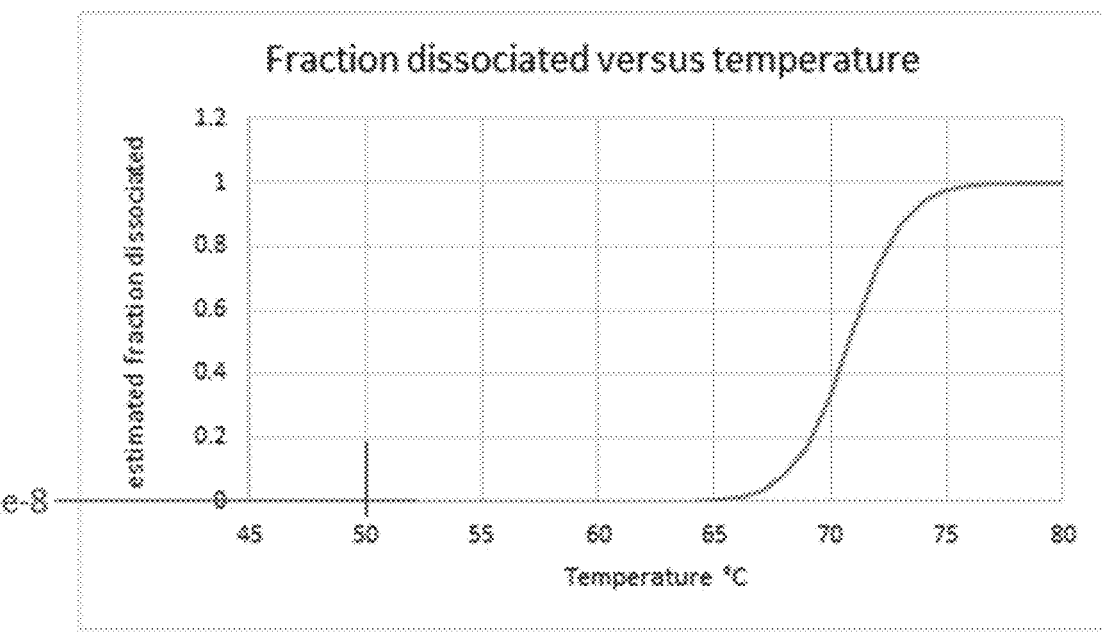
FIG. 24B shows a plot of estimated fraction of dissociated bases versus temperature for an exemplary subsequence.

(d) Sequence from Step 2a, TTTTT, gives B=−0.086, M=−3.03, x=50, y(x)=0.989884 as shown in FIG. 24A.
  (e) 41-mer (Step 2c) calculation yields B=−0.8799, M=70.82, x=50, y(x)=1.1e-8 as shown in FIG. 24B.
  Note that the steepness of the curve in FIG. 24B is much higher due to the greater absolute value of the growth rate, though this may be obscured by the different scales used.
(6) The average of all subsequence values for the first base is calculated to yield the result.
(7) The process is repeated for each base in the sequence.

TABLE 13

| Dimer Parameters | dH (kcal/mol) | dS (cal/K · mol) |
|---|---|---|
| AA | −7.9 | −22.2 |
| AC | −8.4 | −22.4 |
| AG | −7.8 | −21 |
| AT | −7.2 | −20.4 |
| CA | −8.5 | −22.7 |
| CC | −8 | −19.9 |
| CG | −10.6 | −27.2 |
| CT | −7.8 | −21 |
| GA | −8.2 | −22.2 |
| GC | −9.8 | −24.4 |
| GG | −8 | −19.9 |
| GT | −8.4 | −22.4 |
| TA | −7.2 | −21.3 |
| TC | −8.2 | −22.2 |
| TG | −8.5 | −22.7 |
| TT | −7.9 | −22.2 |

Example 21

An iSDA amplification assay was designed using the steps discussed above in Example 20. The 5' end noncoding region of echovirus was targeted, having the sequence shown below:

(SEQ ID NO: 78)
ATCCACCCTACCCCGTTGCAACTTAGAAGCTAATTCAGTACGATCGATAG

GCGGCTCAGTACGCCAACTGAGTCATGATCAAGCACTTCTGTTACCCGG

ACTGAGTATCAATACGCTGCTCACGCGGCTGAAGGAGAAAACGTTCGTTA

CCCGGCCAATTACTTCGAGAAACTTAGTACCACCATGAAGGTTGCGCAGC

GTTTCGCTCCGCACAACCCCAGTGTAGATCAGGTCGATGAGTCACCGCAT

TCCCCACGGGCGACCGTGGCGGTGGCTGCGCTGGCGGCCTGCCCATGGGG

TATCCCATGGGACGCTTCAATACTGACATGGTGTGAAGAGTCTATTGAGC

TAATTGGTAGTCCTCCGGCCCCTGAATGCGGCTAATCCTAACTGCGGAGC

AGATACCCACATGCCAGTGGGCGGTCTGTCGTAACGGGCAACTCTGCAGC

GGAACCGACTACTTTGGGTGTCCGTGTTTCCTTTTATTTCTATAC

Figure 27:
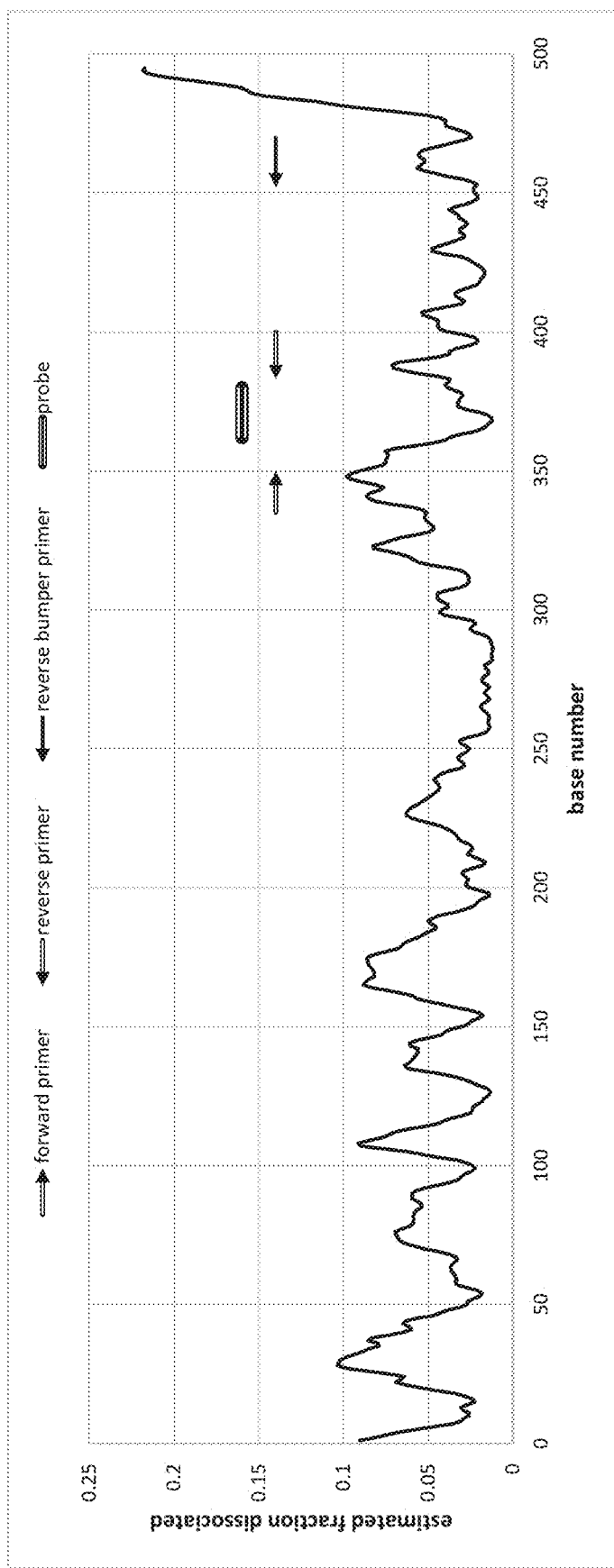
FIG. 27 shows estimated fraction dissociated for bases in echovirus sequence and design of primers and probes for iSDA amplification and detection.
Figure 37B:
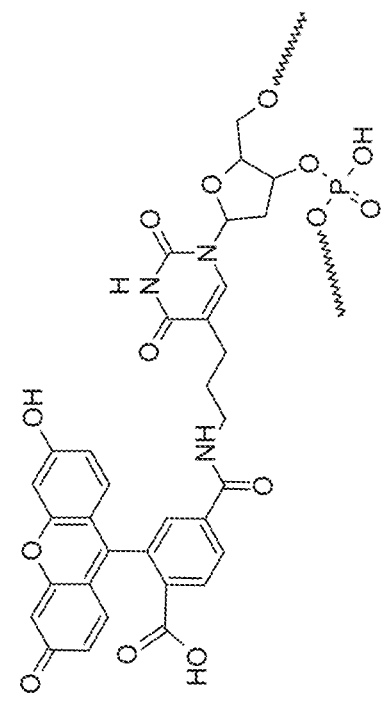
FIG. 37B shows the structure of fluorescein-labeled uridine.
Figure 37A:
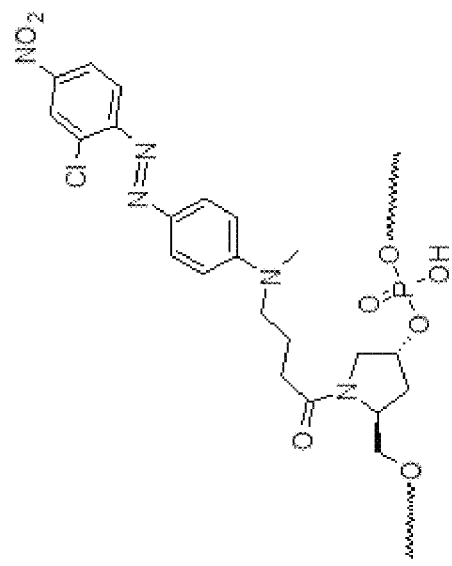
FIG. 37A shows the structure of the Eclipse Dark Quencher.

FIG. 27 shows the fraction of dissociated bases for each base in the sequence of SEQ ID NO:78. Arrows and lines indicate the sequences chosen for the forward primer, reverse primer, reverse bumper primer, and probes to be used in the assay. The primers and probes are identified in Table 14 below. The "Ap probe" contained an abasic spacer labeled Ap that was Spacer 1 from Table A above inserted between the eighth and ninth bases. The Ap probe used in the assay also contained a quencher which was the Eclipse Dark Quencher, shown in FIG. 37A, attached to the first base and a fluorophore which was fluorescein-labeled uridine, shown in FIG. 37B, attached to the eleventh base, to the right of the abasic spacer. For comparison purposes, a probe and an enhancer to be used in typical Endonuclease IV detection were also chosen and are identified below in Table 14. In the assay, the Endo IV probe also contained a quencher which was the Eclipse Dark Quencher attached to the first base and a fluorophore which was fluorescein attached to the eleventh base. The probe sequences are also illustrated in FIG. 25A and FIG. 25B. As in other tables, the lower case bases are non-complementary to the target sequence, the upper case bases are specific to the target sequence, and the underlined portion is the nicking site for Nt.BbvC1B.

TABLE 14

| SEQ ID NO. | Description | Oligonucleotide sequence |
|---|---|---|
| 79 | Forward primer | gctagaaccagtat<u>CCTCAGC</u>GAAGAGTCT ATTGAGC |
| 80 | Reverse primer | gctagaaccagtat<u>CCTCAGC</u>TCCGCAGTT AGGATTA |
| 81 | Reverse bumer | CACCCAAAGTAGTCGGTTC |
| 82 | Ap Probe | CCTCCGGC(Ap)CCTGAATGCG where Ap = Spacer 1 from Table A |
| 83 | Endo IV Probe | TA*GT*CCTCCGGC where A* = Super A and T* = Super T |
| 84 | Endo IV Enhancer | CCTGAATGCGGC |
| 85 | Pleaides Probe | TCCGGCCCCTGAATGCG |
| 86 | PCR Forward Primer | GAAGAGTCTATTGAGCTA |
| 87 | PCR Reverse Primer | GGA*TTRGCCGCA*TTC where A* = Super A, R = A or G |

Figure 29:
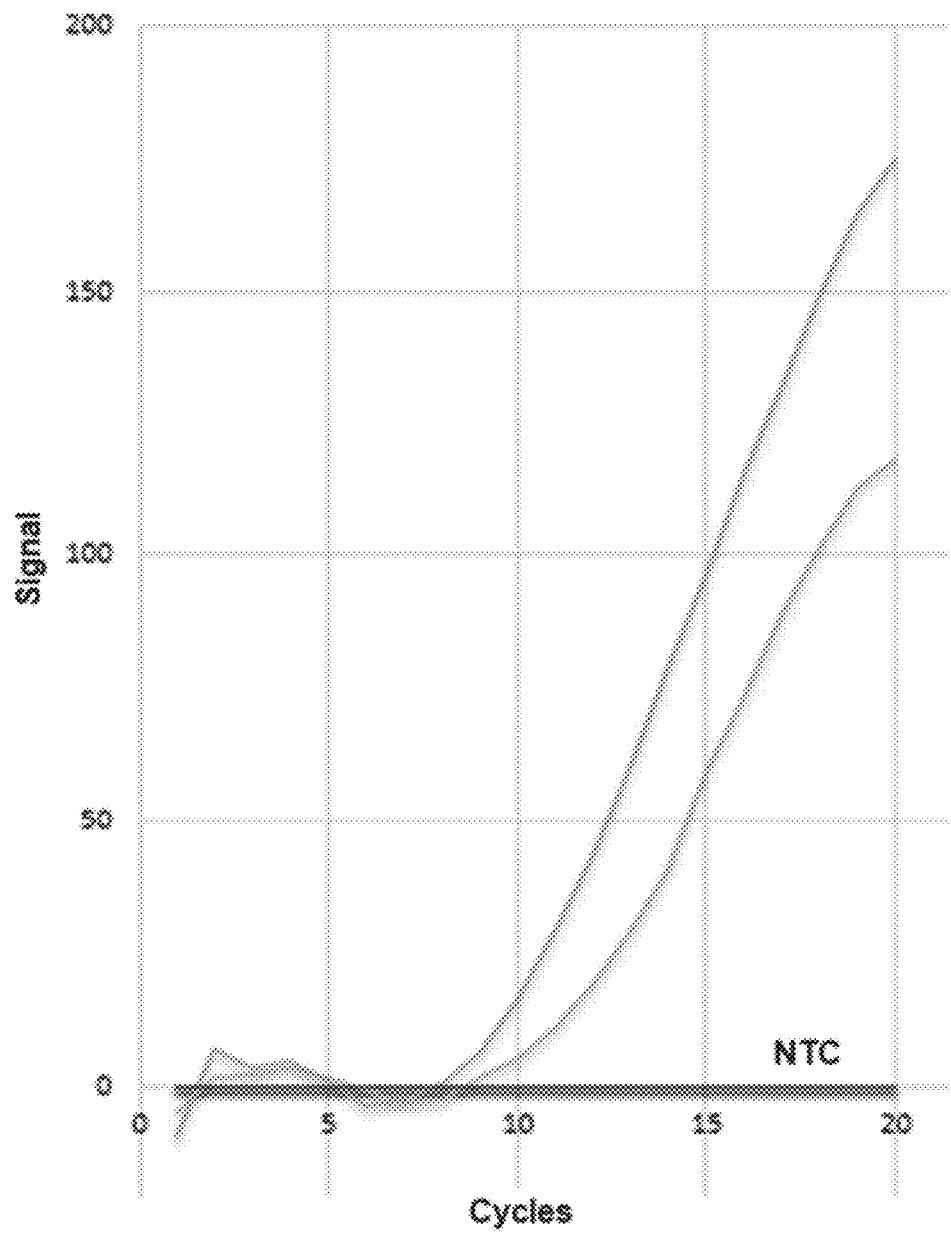
FIG. 29 shows signal strength in iSDA detection using an Endonuclease IV probe enhancer detection system at low target echovirus sample concentration and with NTC.

In this example and the following examples, nucleic acid extraction and amplification was performed using ELITe InGenius fully automated sample-to-result instrument. iSDA was performed in one step with a reverse transcription reaction, using final concentrations of 8 mM MgSO₄, 50 mM KH₂PO₄ pH 7.6, 1 μM forward primer (SEQ ID NO: 79), 1 μM reverse primer (SEQ ID NO: 80). 100 nM reverse bumper (SEQ ID NO: 81), 500 nM Ap Probe (SEQ ID NO: 82) or 250 nM Pleiades probe (SEQ ID NO: 85), 0.2 mM dNTPs, 4 U N.BbvC1B, 20 U Bst 2.0 WarmStart DNA polymerase. 7.5 U WarmStart RTx, 5 U Endonuclease IV in a total volume of 25 μL. The final reaction volume was obtained by combining 15 μL of mixture of iSDA reagents with 10 μL of sample nucleic acid. Reaction was performed at 52° C. for 20 minutes. Fluorescent readings were taken every minute Detection using Pleiades probe in iSDA reaction shows that there is no detectable signal from the NTC sample with interrogation of high concentration echovirus samples ($10^4$ copies/reaction). This is shown in FIG. 28A. However, at lower sample concentrations, such as 100 copies, when intensity of the specific signal significantly drops it is difficult to discriminate between the sample and the NTC signals. This is shown in FIG. 28B. However, use of the Endo IV probe for detection of the samples at low concentration (100 copies/reaction), showed an absence of NTC signal, but also a relatively weak sample signal. This is shown in FIG. 29.

Figure 30:
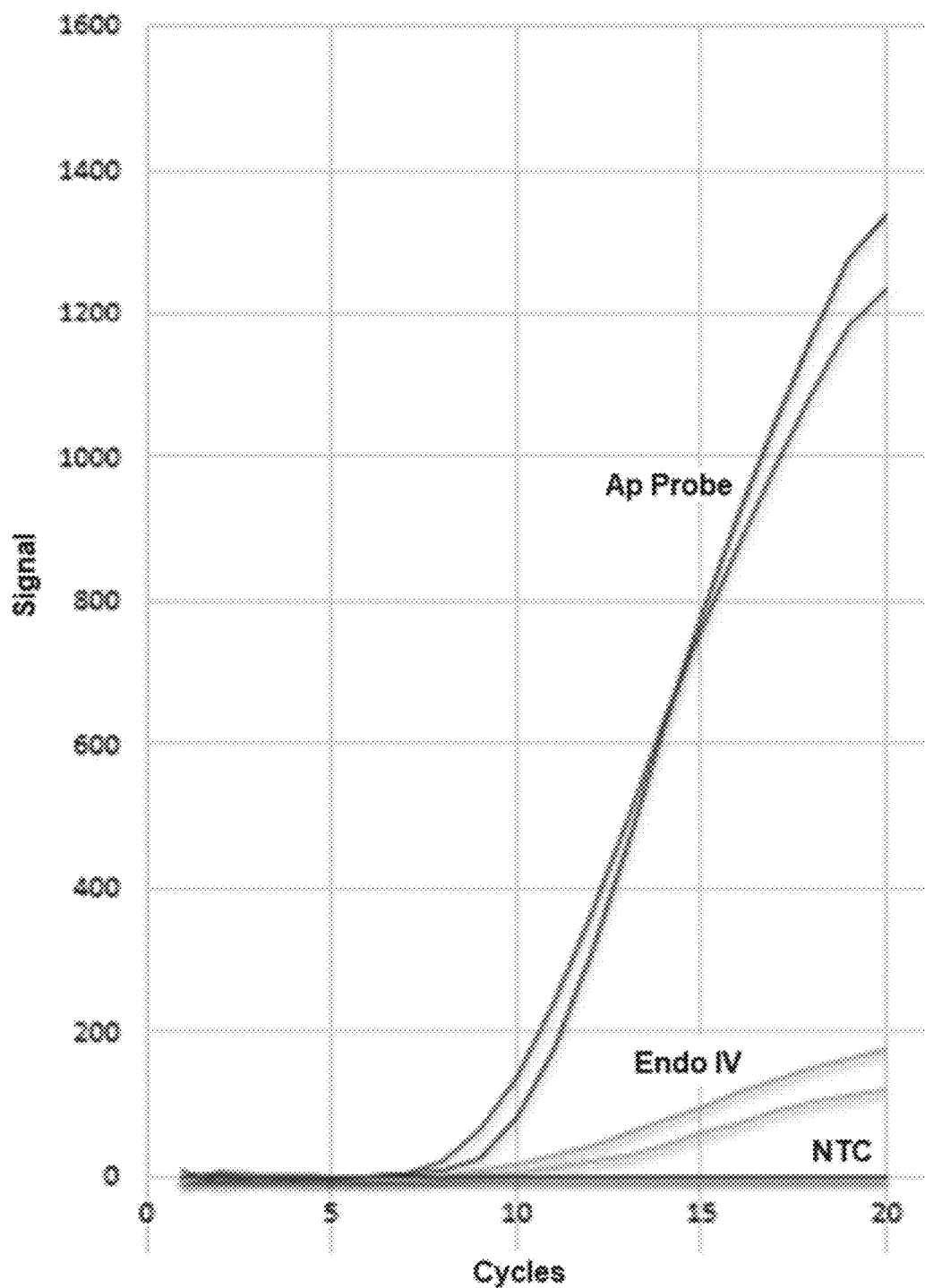
FIG. 30 shows iSDA detection of echovirus amplified target (about 100 copies/reaction) by a Endonuclease IV probe system ("Endo IV") compared to a probe including the abasic spacer according to preferred embodiments disclosed herein ("Ap Probe"), with NTC.
Figure 31A:
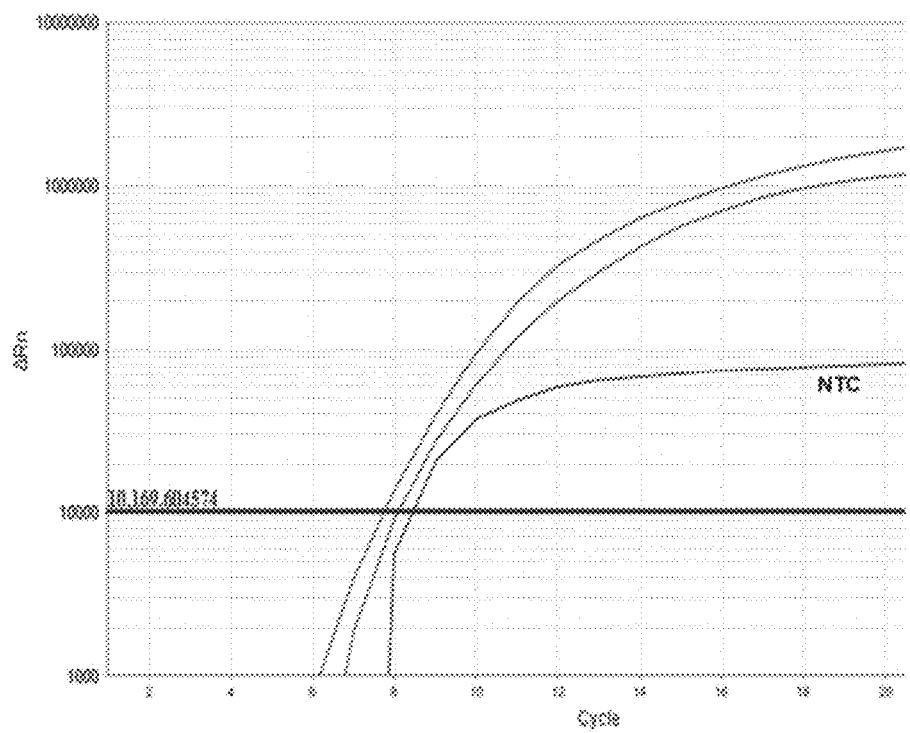
FIG. 31A shows results of amplification using a Pleiades probe for detection of echovirus at 100 target copies per reaction, with NTC.
Figure 31B:
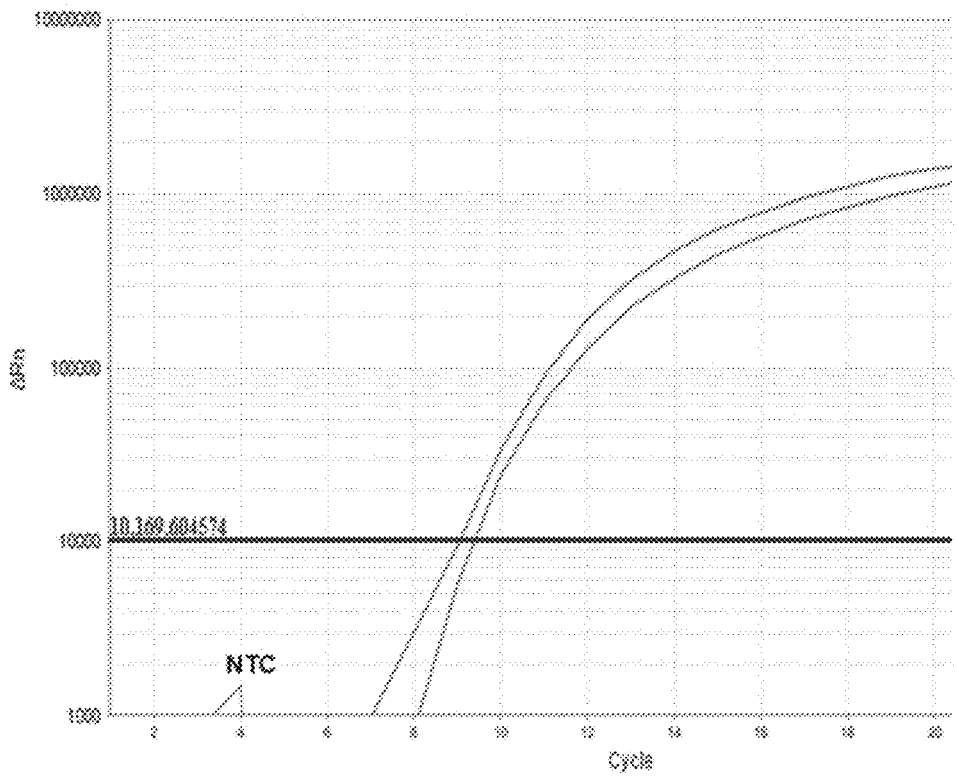
FIG. 31B shows results of amplification using a probe containing the abasic spacer according to preferred embodiments described herein for detection of echovirus at 100 target copies per reaction, with NTC.

Additional experiments compared detection of the target (about 100 copies/reaction) by the Endo IV probe with the Ap probe according to preferred embodiments herein including the abasic spacer (SEQ ID NO: 82, shown in FIG. 25B). FIG. 30 shows a comparison of signal strength between Endo IV probe and the Ap In both cases, the NTC shows no signal, but the probe containing the abasic spacer shows a significantly higher signal for the amplified target. FIG. 31A shows results of amplification using a Pleiades probe (SEQ ID NO: 85) for detection of echovirus at 100 target copies per reaction and FIG. 31B shows results of amplification of the same amount of target using the Ap probe. While both probes generate similar signal strength, the detections using a Pleiades probe shows a significant NTC signal, while the detection using a probe with the abasic spacer as described herein shows no NTC signal.

Example 22

Figure 32:
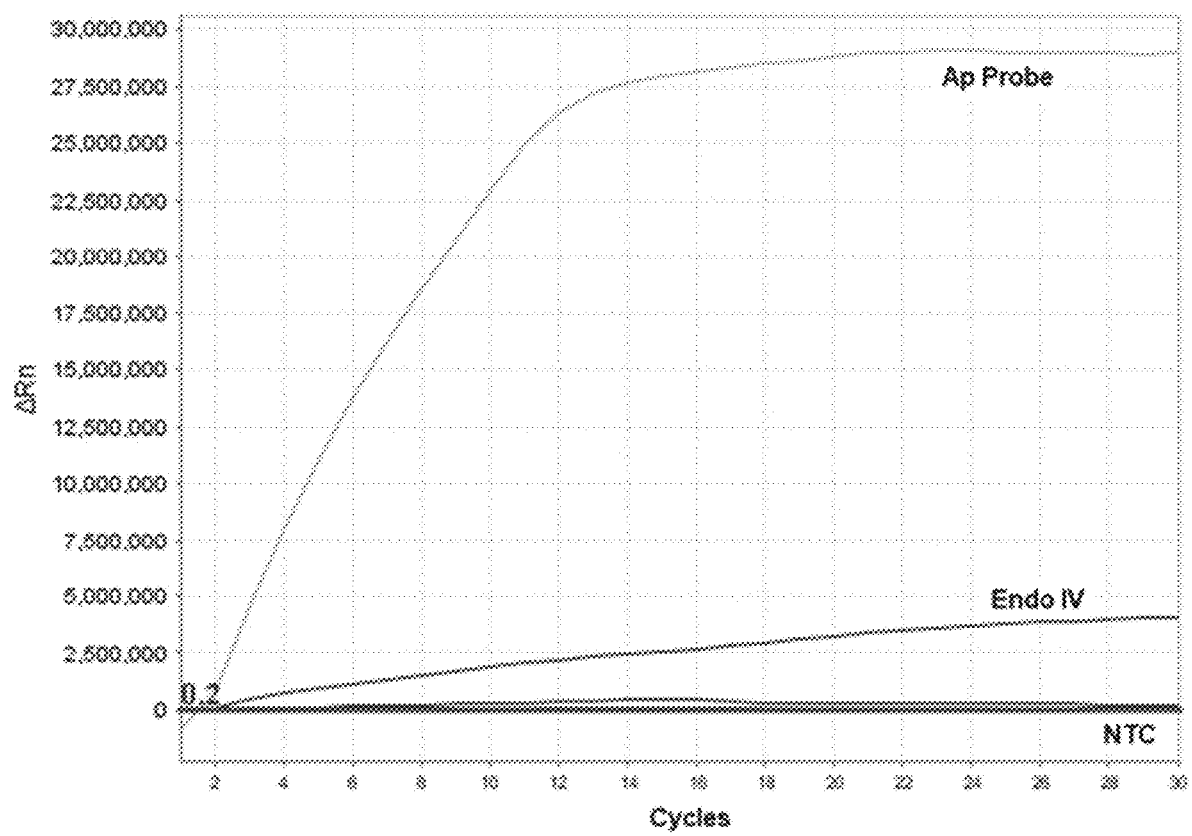
FIG. 32 shows a comparison of reactions of a typical Endonuclease IV probe system ("Endo IV") and a probe containing the abasic spacer according to preferred embodiments ("Ap Probe") with synthetic template, with NTC.

Another experiment compared the signal generation by the Endo IV probe and the Ap probe in a reaction containing only Endonuclease IV enzyme, iSDA buffer and a synthetic complement template. No other iSDA reagents were included in the reaction. Concentration of each probe was 500 nM and that of the complement was 25 nM. Reaction temperature was 50° C. Ten times stronger signal was observed with the probe containing the abasic spacer, as shown in FIG. 32. A better efficiency of the Ap probe can likely be explained by the cycling mechanism of the signal generation. The melting temperatures of the products, produced by Endo IV enzyme cleavage, are lower than the iSDA reaction temperature. Therefore, these products cannot compete for the binding site with the undigested probe. They dissociate from the target and make it accessible for the intact probe to hybridize, get cleaved and release the fluorescent signal. This mechanism is quite different from the conventional Endo IV probe, where the digested probe is essentially the same probe lacking a fluorophore. Once cleaved it can still occupy the target, preventing the binding of the undigested probe. This in turn affects the signal in the SDA reaction, especially in the case of the low positive samples.

Figure 33B:
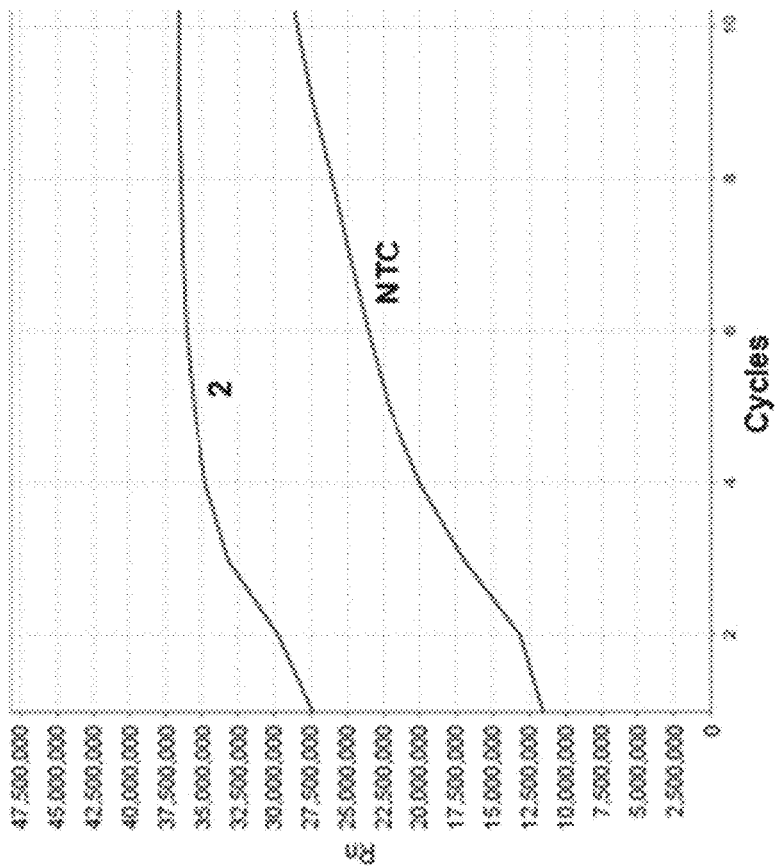
FIG. 33B shows reaction of a probe containing the abasic spacer. Spacer 2, according to preferred embodiments disclosed herein with a synthetic template, with NTC.
Figure 33A:
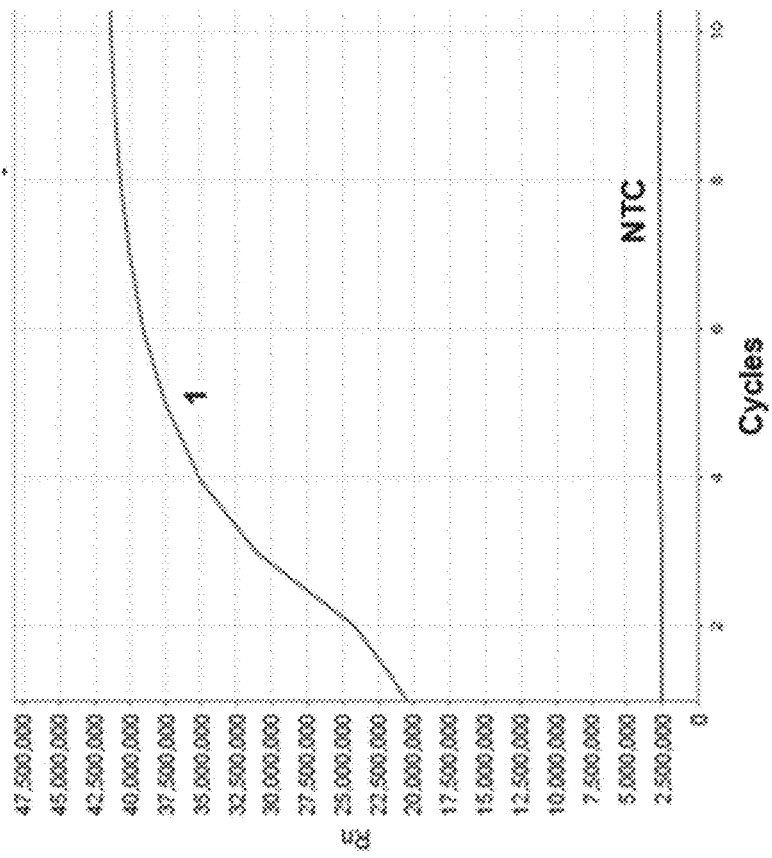
FIG. 33A shows reaction of a probe containing the abasic spacer. Spacer 1, according to preferred embodiments disclosed herein with a synthetic template, with NTC.
Figure 33D:
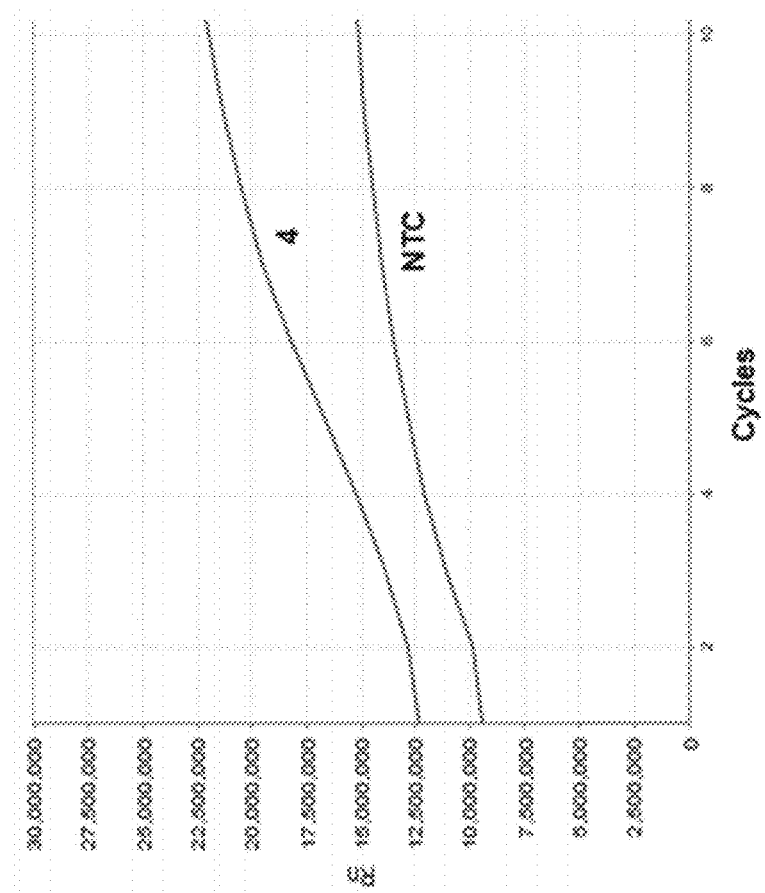
FIG. 33D shows reaction of a probe containing the abasic spacer. Spacer 4, according to preferred embodiments disclosed herein with a synthetic template, with NTC.
Figure 33C:
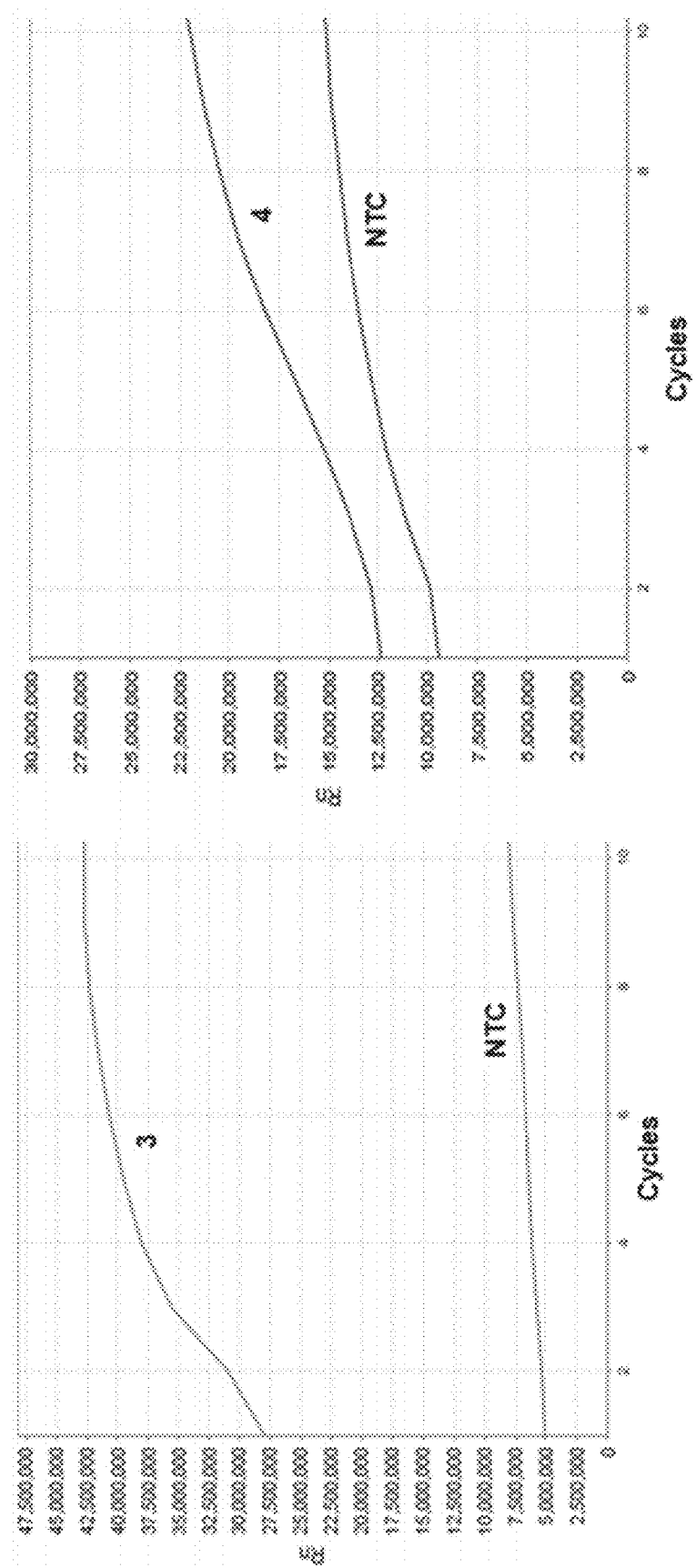
FIG. 33C shows reaction of a probe containing the abasic spacer, Spacer 3, according to preferred embodiments disclosed herein with a synthetic template, with NTC.

Additional experiments examined the effect of different abasic spacers listed above in Table A, spacers 1 to 4, on amplification signal and NTC background. The method was the same as that described above for FIG. 32, with probe concentration 500 nM, and synthetic complement at 25 nM and the reaction temperature at 50° C. Results are shown in FIG. 33A-FIG. 33D. Spacer 1 showed the more favorable NTC and best signal generation, as seen in FIG. 33A. The ratio of target signal generated to NTC signal by probes containing spacers 1 to 4 were respectively, 16, 5.3, 1.3 and 1.4.

Example 23

Additional experiments dealt with the optimization of potassium phosphate concentration for use in iSDA detection using the Ap probe. Potassium phosphate concentration was evaluated at 50, 55 and 58 mM, respectively at Echovirus RNA levels of 5, 20, 25 copies/reaction. Each level was tested in four replicate samples. As shown in Table 15 below, the sensitivity was the highest in the reactions with phosphate concentration at 55 mM.

TABLE 15

| Target concentration | Potassium Phosphate Concentration | | |
| --- | --- | --- | --- |
|  | 50 mM | 55 mM | 58 mM |
| 25 copies/reaction | 3/4 detected | 4/4 detected | 4/4 detected |
| 10 copies/reaction | 2/4 detected | 4/4 detected | 3/4 detected |
| 5 copies/reaction | 0/4 detected | 3/4 detected | 3/4 detected |

Figure 34:
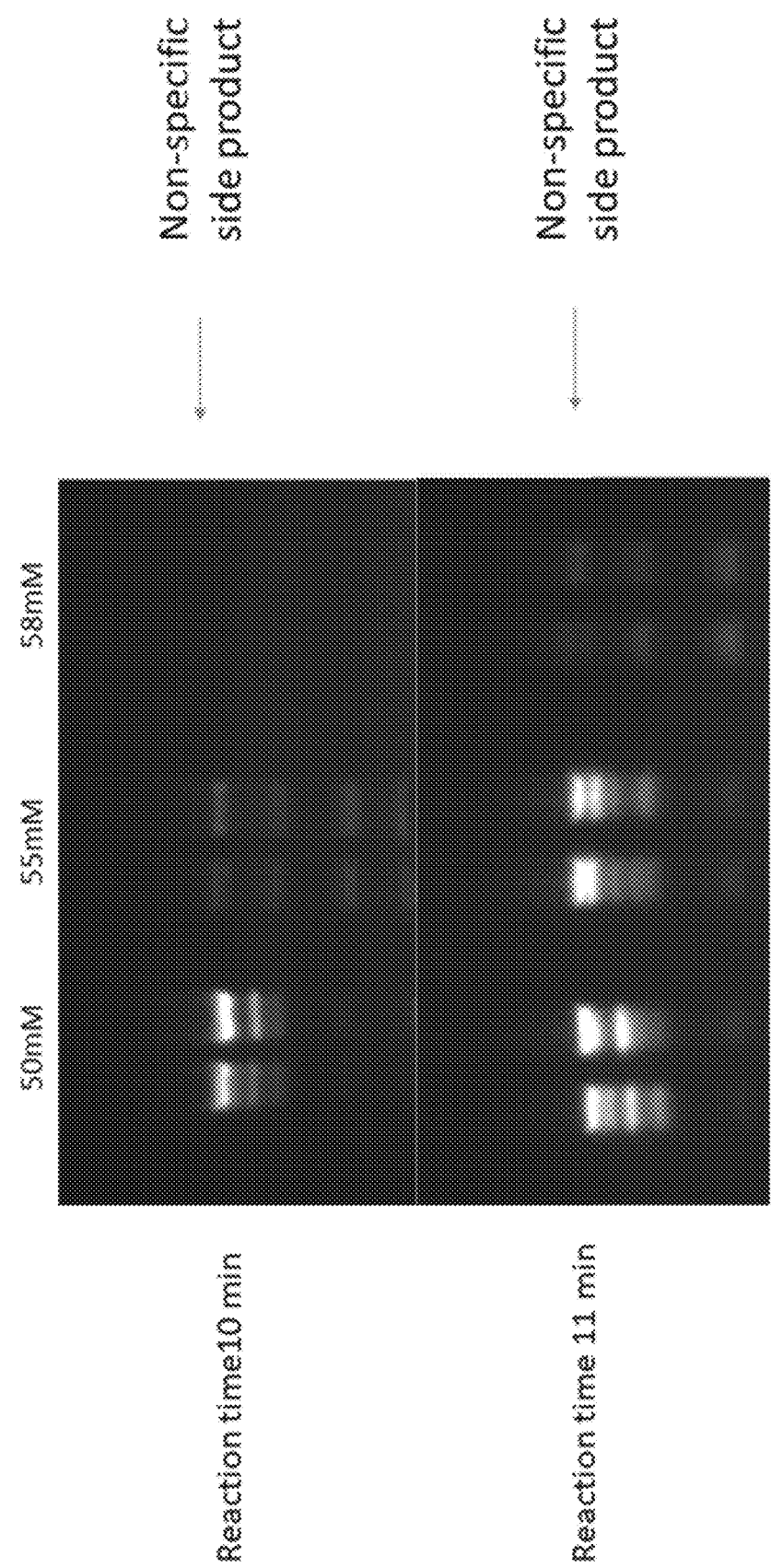
FIG. 34 shows formation of side products measured on Agarose gel at 10 and 11 minutes for iSDA detection using a probe containing the abasic spacer according to preferred embodiments disclosed herein at different potassium phosphate concentrations.

Potassium phosphate concentration also has an effect on side product formation. The formation of the non-specific side products is a common problem in various isothermal amplification reactions, which significantly reduce the sensitivity of the these methods (Niemz et al., Nucleic Acids Res. 40(11): e87 (2012)). To show this effect, the duplicate NTC samples were used instead of RNA in iSDA reactions described above. To monitor the rate of side product formation, reactions were run for 10 and 11 minutes. After the completion of iSDA the samples were analyzed on agarose gel. The results are shown in FIG. 34. As shown, potassium phosphate concentration has a significant effect on side product formation with 58 mM concentration producing the least amount. Increased potassium phosphate concentration likely reduces formation of the side products by having an inhibitory effect on the enzyme's activity. When target concentration in the reaction is low, the fast accumulating side products effectively compete for resources (primers, enzymes, dNTP) of the iSDA reaction and therefore reduce its sensitivity. The data presented in Table 15 and FIG. 34 support a conclusion that increased potassium phosphate concentration reduces the amount of side product and helps amplification of the target at low copy number.

Example 24

Figure 35:
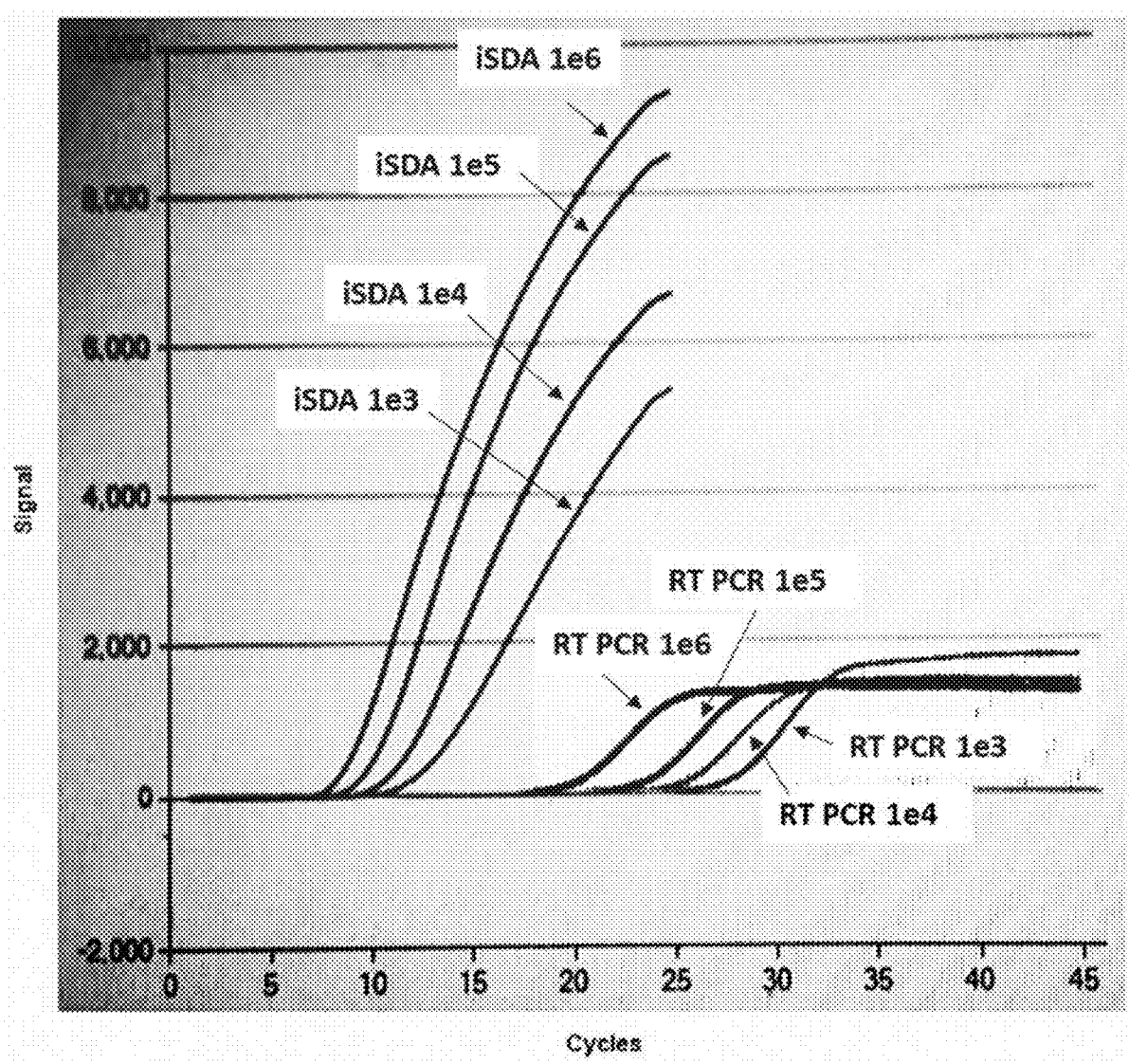
FIG. 35 shows a comparison of iSDA detection using probes with abasic spacers according to preferred embodiments disclosed herein ("Ap Probe") with real-time PCR amplification ("RT-PCR") of a 10 fold titration of a high copy number echovirus sample with four replicates.
Figure 36A:
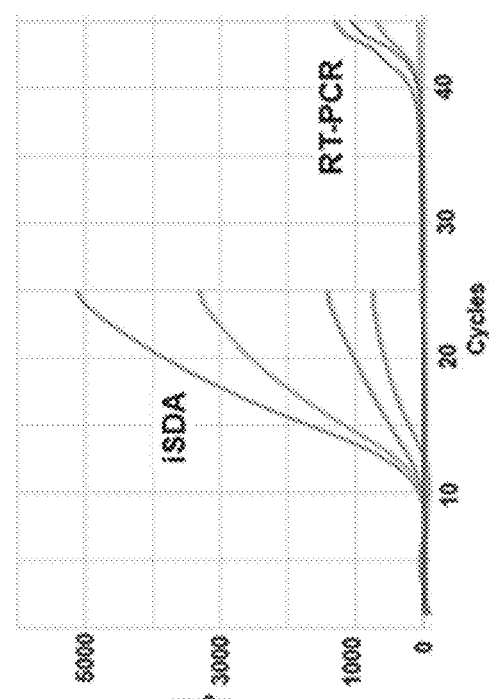
FIG. 36A shows signal generation of iSDA amplification ("iSDA") using probes with abasic spacers according to preferred embodiments disclosed herein compared to real time PCR amplification ("RT-PCR") at 25 copies/reaction with four replicates.
Figure 36B:
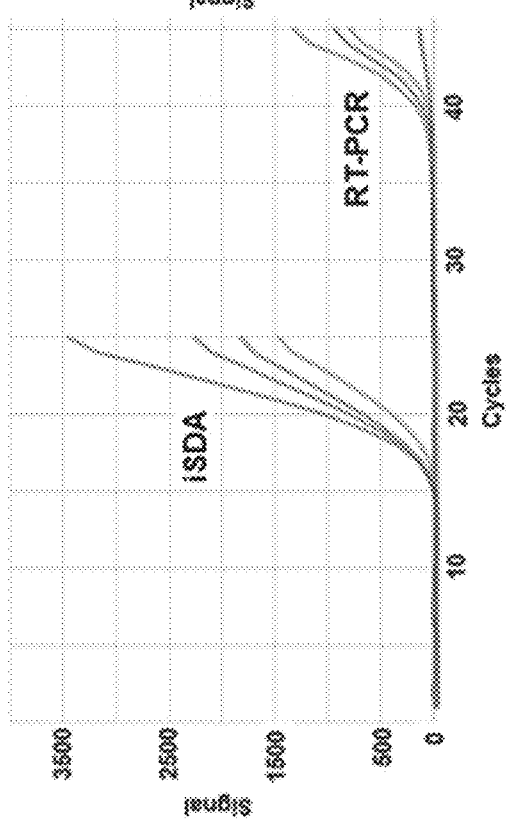
FIG. 36B shows signal generation of iSDA amplification ("iSDA") using probes with abasic spacers according to preferred embodiments disclosed herein compared to real time PCR amplification ("RT-PCR") at 12 copies/reaction with four replicates.
Figure 36D:
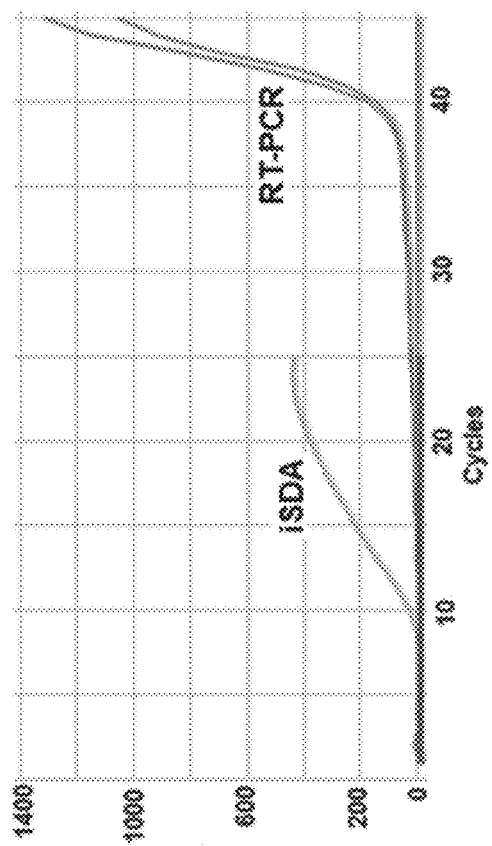
FIG. 36D shows signal generation of iSDA amplification ("iSDA") using probes with abasic spacers according to preferred embodiments disclosed herein compared to real time PCR amplification ("RT-PCR") at 25 copies/reaction with four replicates.
Figure 36C:
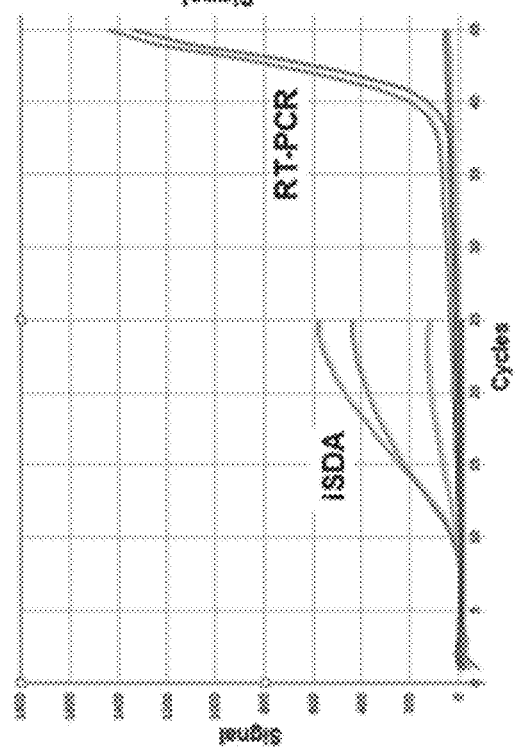
FIG. 36C shows signal generation of iSDA amplification ("iSDA") using probes with abasic spacers according to preferred embodiments disclosed herein compared to real time PCR amplification ("RT-PCR") at 10 copies/reaction with four replicates.

An additional experiment compared iSDA detection using the Ap probe with real-time PCR amplification PCR was performed using LunaScript™ RT SuperMix (NEB), 1 μM forward primer (SEQ ID NO: 86). 1 μM reverse primer (SEQ ID NO: 87), 250 nM Pleiades probe SEQ ID NO: 85), according to manufacturing protocol. FIG. 35 shows the results of a 10 fold titration of a high positive clinical echovirus sample (approx. $10^6$ copies/reaction). iSDA resulted in significantly higher fluorescent signal and was completed in 15 minutes when PCR reaction only finished its reverse transcription step. A similar experiment compared iSDA amplification using Ap probe with PCR at 25, 12, 10 and 5 copies/reaction. Each concentration was amplified in four replicates. The results are shown in Table 16 below and in FIG. 36A to 36D for 25, 12, 10, and 5 copies, respectively. While both methods demonstrated similar sensitivity, iSDA was completed in 20 minutes, comparing to 90 minutes for PCR reaction (according to the instrument run log file).

TABLE 16

| Target concentration | iSDA | PCR |
| --- | --- | --- |
| 25 copies/reaction | 4/4 detected | 4/4 detected |
| 12 copies/reaction | 4/4 detected | 3/4 detected |
| 10 copies/reaction | 3/4 detected | 2/4 detected |
| 5 copies/reaction | 1/4 detected. | 2/4 detected |

REFERENCES CITED

The following documents and publications are hereby incorporated by reference.

U.S. and Foreign Patent Documents

U.S. Pat. No. 5,824,796
U.S. Pat. No. 5,912,340
U.S. Pat. No. 5,455,166
U.S. Pat. No. 7,282,328
U.S. Pat. No. 4,943,522
U.S. Pat. No. 7,488,578
US Application Publication No. 2012-0015358 A
U.S. Pat. No. 5,624,825
U.S. RE39885
U.S. Pat. No. 5,455,166
U.S. Pat. No. 5,422,252
U.S. Pat. No. 5,624,825
U.S. Pat. No. 5,712,124
U.S. Pat. No. 5,270,184
U.S. Pat. No. 5,470,723
U.S. Pat. No. 5,561,944
U.S. Pat. No. 5,736,365
U.S. Pat. No. 6,127,121
U.S. Pat. No. 6,440,706
U.S. Pat. No. 6,660,845
U.S. Pat. No. 6,683,173
U.S. Pat. No. 6,790,945
U.S. Pat. No. 7,045,610
U.S. Pat. No. 7,252,940
U.S. Pat. No. 7,381,818
U.S. Pat. No. 7,751,982
U.S. Pat. No. 7,799,554
U.S. Pat. No. 8,202,972
U.S. Pat. No. 9,328,384
U.S. Patent Application Publication No. US2009/0111100
U.S. Patent Application Publication No. US2009/0092967
U.S. Patent Application Publication No. 2010/057862
U.S. Patent Application Publication No. 20110151457
U.S. Patent Application Publication No. 2011/0171649
U.S. Patent Application Publication No. 2012/0244535
PCT Publication WO 01/38584
PCT Publication WO 01/64958

Non-Patent References

Afonina et al., Single Nucleotide Polymorphism Detection with fluorescent MGB Eclipse Systems in A-Z of Quantitative PCR. Ed. S. A. Bustin. International University Line, La Jolla, Calif., pages 718-731 and XII-XIII, 2004)
Barzilay and Hickson. Bioessays. 17(8):713-9 (1995)
Besnier and Kong, EMBO Reports. 21: 782-786 (2001)
Dauxois, et al., Physical Review E. Vol 47, Number 1, 684-695 (1993)
Ehses et al., J. Biochem. Biophys. Methods. 63:170-86 (2005).
Eschenmoser et al, Helvetica Chimica Acta, 76: 2161-2183 (1993)
Fran-Kamentskii. Artificial DNA; PNA & XNA. 2:1, 1-3 (2011)
Kutyavin et al, Nucleic Acids Res. 34: e128 (2006)
Mergny and Lacroix, Oligonucleotides, 13: 515-537 (2003)
Metzler et al., Journal of Physics: Condensed Matter, 21: 1-14 (2009)
Molecular Cloning: a laboratory manual
Niemz et al., Trends in Biotechnol., 29:240-250 (2011)
Niemz et al., Nucleic Acids Res. 40(11): e87 (2012)
Nuovo, Diagn Mol Pathol. 9(4): 195-202 (2000)
M Panaccio and A Lew. PCR based diagnosis in the presence of 8% (v/v) blood. Nucleic Acids Res., 19: 1151 (1991)
Owczarzy et al, Biochemistry, 47, 5336-5353 (2008)
Pohl and Shih Expert Rev Mol Diagn., 4(1):41-7 (2004)
Polley et al, J. Clin. Microbiol. 48:2866-2871 (2010)
Ramirez et al, Nucl. Acids Res., 40:5560-8 (2012)
Roberts et al., Nucl. Acids Res., 31: 418-420 (2003)
SantaLucia. Jr., Proc. Natl. Acad. Sci. USA, Vol 95, pp 1460-1465 (1998)
Sedlak and Jerome, Diagn Microbiol Infect Dis., January; 75(1):1-4 (2013)
Walker et al., NAR 20: 1691-1695 (1992)
Walker, PCR Methods and Applications, 3: 1-6 (1993)
Walker et al., NAR 22: 2670 (1994)
Walker et al., Clin. Chem., 42: 9-13 (1996)
Walker et al., Clin. Chem., 42: 1604-8 (1996)
Walker et al., NAR 24:349 (1996)
Wang et al., Clin. Chem., 49: 1599 (2003)
White, Handler and Smith. Principles of Biochemistry $5^{th}$ Edition. McGraw-Hill Kogakush, Ltd, pages 192-197, 1993
Xu et al. PNAS 98: 12990-12995 (2001)
Yager et al., Analyst 140(22), 7540-9 (2015)
Zheleznaya et al., Biochemistry (Mosc). 74:1457-66 (2009)

What is claimed is:

1. A method for detecting an amplified target sequence using isothermal strand displacement amplification, the method comprising:
   (a) analyzing a double-stranded target nucleic acid sequence to locate high dissociation sequence regions, wherein the high dissociation sequence regions have an estimated fraction of dissociated bases of about 0.04 to about 0.2, and wherein the double-stranded target nucleic acid sequence lacks a natural nicking enzyme recognition site;
   (b) designing a forward primer and a reverse primer to hybridize to the high dissociation sequence regions of the double-stranded target nucleic acid sequence;
   (c) contacting a nucleic acid sample having the double-stranded target nucleic acid sequence with an amplification reaction mixture comprising:
      the forward primer and the reverse primer,
         wherein the forward primer has the formula:
            A-B,
            wherein B comprises a portion of the forward primer that is complementary to the target nucleic acid sequence, and wherein A comprises a portion of the forward primer that is non-complementary to the target nucleic acid sequence and comprises a forward nicking enzyme recognition sequence,
         wherein the reverse primer has the formula:
            A'-B',
            wherein B' comprises a portion of the reverse primer that is complementary to the target nucleic acid sequence, and wherein A' comprises a portion of the reverse primer that is non-complementary to the target nucleic acid sequence and comprises a reverse nicking enzyme recognition sequence,
      a polymerase enzyme having strand displacement activity, and
      a nicking enzyme specific for the forward nicking enzyme recognition sequence or the reverse nicking enzyme recognition sequence:
   (d) incubating the amplification reaction mixture and the nucleic acid sample under amplification conditions suitable for amplification of a target nucleic acid to produce an amplified target nucleic acid, wherein the amplified nucleic acid comprises either a forward primer portion that is complementary to B or a reverse primer portion that is complementary to B',
   wherein the contacting step and the incubating step are carried out at a temperature between about 40° C., and about 65° C. and amplification of the target nucleic acid occurs without a thermal denaturation step prior to amplification; and
   (e) detecting the amplified target nucleic acid by hybridizing an oligonucleotide probe to a detection portion of the amplified target nucleic acid, wherein the detection portion of the amplified target nucleic acid is non-complementary to and does not overlap with the forward primer portion or the reverse primer portion, wherein the oligonucleotide probe has the formula:

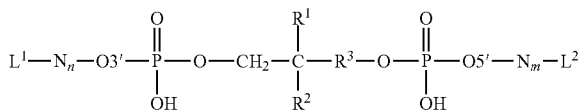

wherein N is a natural or artificial nucleotide or a nucleoside unit, n and m are independently from about 5 to about 15, $N_n$ is a first nucleotide sequence having a 3'-terminal deoxyribose ring, $N_m$ is a second nucleotide sequence having a 5'-terminal deoxyribose ring, O3' is the 3' oxygen atom of the 3'-terminal deoxyribose ring of $N_n$, O5' is the 5' oxygen atom of the 5'-terminal deoxyribose ring of $N_m$, $L^1$ and $L^2$ are independently a fluorophore and a quencher, $R^1$ and $R^2$ are independently selected from H, substituted or unsubstituted hydroxyl, amine, thiol, $(C_1-C_{100})$alkyl, $(C_1-C_{100})$heteroalkyl, $(C_1-C_{100})$alkenyl, $(C_1-C_{100})$heteroalkenyl, $(C_1-C_{100})$alkynyl, $(C_1-C_{100})$heteroalkynyl aryl or heteroaryl, $R^3$ is selected from substituted or unsubstituted $(C_1-C_{100})$alkylene or $(C_1-C_{100})$heteroalkylene, or $R^1$, $R^2$ and $R^3$ form one or more 4 to 10 member carbon or heteroatomic rings, and wherein the oligonucleotide probe is cleaved by an endonuclease to produce a fluorescent signal.

2. The method of claim 1 wherein the amplification reaction mixture further comprises one or more bumper oligonucleotides.

3. The method of claim 1 wherein at least one N comprises a modified base.

4. The method of claim 1 wherein one or both of $L^1$ and $L^2$ are attached to an internal nucleotide base.

5. The method of claim 1 wherein the endonuclease is Endonuclease IV.

6. The method of claim 1 wherein the amplification reaction mixture further comprises an internal control.

7. The method of claim 1 wherein the high dissociation sequence regions are located by calculating duplex stabilities in the double-stranded target nucleic acid sequence using an algorithm applying a nearest-neighbor model for duplex formation thermodynamics for each neighboring base pair.

8. The method of claim 1 wherein the forward primer and the reverse primer are present in different concentrations in the amplification reaction mixture.

9. The method of claim 1 wherein at least one of the forward primer and reverse primer is substituted with at least one modified base.

10. The method of claim 1 wherein the contacting step and the incubating step are carried out at a temperature between about 45° C., and about 55° C.

11. The method of claim 1 wherein at least one forward primer or reverse primer hybridizes to the high dissociation sequence regions of the double-stranded target nucleic acid sequence.

12. The method of claim 1 further comprising identifying a maximized high dissociation sequence region of the double-stranded target nucleic acid sequence that has a highest estimated fraction of dissociated bases over the double-stranded target nucleic acid sequence and designing a forward primer and a reverse primer to hybridize to the maximized high dissociation sequence region.

13. The method of claim 1, further comprising the step of determining absolute concentration of the amplified target nucleic acid using a digital format.

14. A method for detecting an amplified target sequence using isothermal strand displacement amplification, the method comprising:
(a) analyzing a double-stranded target nucleic acid sequence to locate high dissociation sequence regions, wherein the high dissociation sequence regions have an estimated fraction of dissociated bases of about 0.04 to about 0.2, and wherein the double-stranded target nucleic acid sequence lacks a natural nicking enzyme recognition site;
(b) designing a forward primer and a reverse primer to hybridize to the high dissociation sequence regions of the double-stranded target nucleic acid sequence;
(c) contacting a nucleic acid sample having the double-stranded target nucleic acid sequence with an amplification reaction mixture comprising:
the forward primer and the reverse primer,
wherein the forward primer has the formula:

A-B, wherein B comprises a portion of the forward primer that is complementary to the target nucleic acid sequence, and wherein A comprises a portion of the forward primer that is non-complementary to the target nucleic acid sequence and comprises a forward nicking enzyme recognition sequence,
wherein the reverse primer has the formula:

A'-B', wherein B' comprises a portion of the reverse primer that is complementary to the target nucleic acid sequence, and wherein A' comprises a portion of the reverse primer that is non-complementary to the target nucleic acid sequence and comprises a reverse nicking enzyme recognition sequence,
a polymerase enzyme having strand displacement activity, and
a nicking enzyme specific for the forward nicking enzyme recognition sequence or the reverse nicking enzyme recognition sequence;
(d) incubating the amplification reaction mixture and the nucleic acid sample under amplification conditions suitable for amplification of a target nucleic acid to produce an amplified target nucleic acid, wherein the amplified nucleic acid comprises either a forward primer portion that is complementary to B or a reverse primer portion that is complementary to B',
wherein the contacting step and the incubating step are carried out at a temperature between about 40° C., and about 65° C., and amplification of the target nucleic acid occurs without a thermal denaturation step prior to amplification; and
(e) detecting the amplified target nucleic acid by hybridizing an oligonucleotide probe to a detection portion of the amplified target nucleic acid, wherein the detection portion of the amplified target nucleic acid is non-complementary to and does not overlap with the forward primer portion or the reverse primer portion, wherein the oligonucleotide probe has the formula:

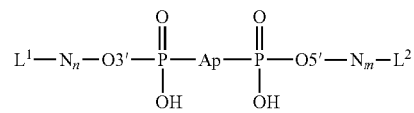

wherein N is a natural or artificial nucleotide or a nucleoside unit, n and m are independently from about 5 to about 15, $N_n$ is a first nucleotide sequence having a 3'-terminal deoxyribose ring, $N_m$ is a second nucleotide sequence having a 5'-terminal deoxyribose ring, $L^1$ and $L^2$ are independently a fluorophore and a quencher, O3' is the 3' oxygen atom of the 3'-terminal deoxyribose ring of $N_n$, O5' is the 5' oxygen atom of the 5'-terminal deoxyribose ring of $N_m$, and Ap is selected from

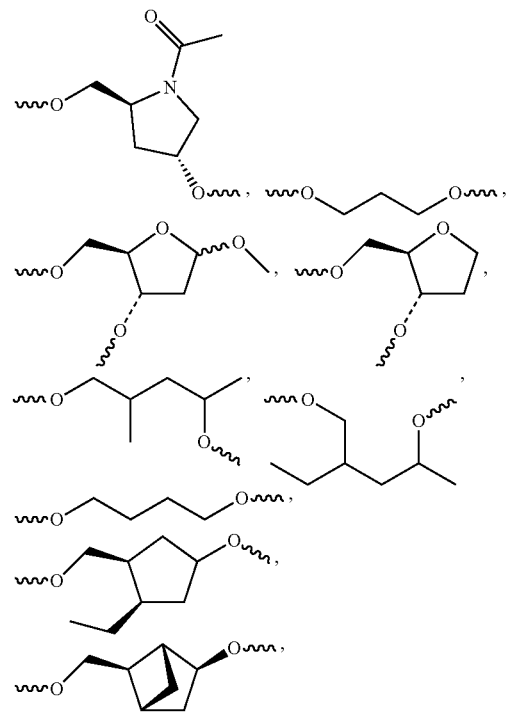

-continued
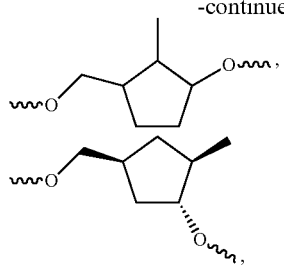
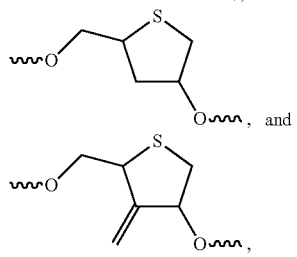
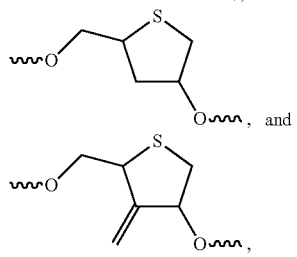
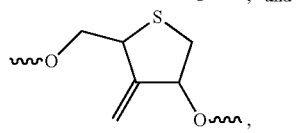
and wherein the oligonucleotide probe is cleaved by an endonuclease to produce a fluorescent signal.
* * * * *

UNITED STATES PATENT AND TRADEMARK OFFICE
CERTIFICATE OF CORRECTION

Page 1 of 2

PATENT NO. : 10,975,423 B2
APPLICATION NO. : 16/660961
DATED : April 13, 2021
INVENTOR(S) : Yevgeniy S. Belousov et al.

It is certified that error appears in the above-identified patent and that said Letters Patent is hereby corrected as shown below:

In the Specification
1. In Column 1, Line 63, delete "Ltd." and insert -- Ltd., --, therefor.
2. In Column 2, Line 8, delete "Reports." and insert -- Reports, --, therefor.
3. In Column 2, Line 19, delete "al." and insert -- al., --, therefor.
4. In Column 5, Line 42, delete "spacer." and insert -- spacer, --, therefor.
5. In Column 5, Line 45, delete "spacer." and insert -- spacer, --, therefor.
6. In Column 5, Line 51, delete "spacer." and insert -- spacer, --, therefor.
7. In Column 8, Line 6, delete "2-aminoadenine." and insert -- 2-aminoadenine, --, therefor.
8. In Column 8, Line 8, delete "6-amino-4-hydroxy-[3.4-d]pyrimidine." and insert -- 6-amino-4-hydroxy-[3,4-d]pyrimidine. --, therefor.
9. In Column 8, Lines 19-20, delete "uridine: 4-(4,6-Diamino-1H-pyrazolo[3.4-d pyrimidin-3-yl)-but-3-yn-1-ol," and insert -- uridine; 4-(4,6-Diamino-1H-pyrazolo[3,4-d]pyrimidin-3-yl)-but-3-yn-1-ol, --, therefor.
10. In Column 8, Line 27, delete "ol."" and insert -- ol," --, therefor.
11. In Column 8, Line 36, delete "brackets." and insert -- brackets, --, therefor.
12. In Column 8, Line 38, delete "(509). Calcein (517)." and insert -- (509), Calcein (517), --, therefor.
13. In Column 8, Line 39, delete "(520)." and insert -- (520), --, therefor.
14. In Column 8, Line 41, delete "(525)." and insert -- (525), --, therefor.
15. In Column 8, Line 43, delete "(533). JOE (548)." and insert -- (533), JOE (548), --, therefor.
16. In Column 8, Line 44, delete "(565)." and insert -- (565), --, therefor.
17. In Column 8, Line 45, delete "(568)." and insert -- (568), --, therefor.
18. In Column 8, Line 45, delete "(570). Cy3TM (570)." and insert -- (570), Cy3TM (570), --, therefor.
19. In Column 8, Line 47, delete "(575)." and insert -- (575), --, therefor.
20. In Column 8, Line 52, delete "(642)." and insert -- (642), --, therefor.
21. In Column 8, Line 53, delete "(648). TO-PROTM-3 (660). TOTO®-3 (660)." and insert -- (648), TO-PROTM-3 (660), TOTO®-3 (660), --, therefor.
22. In Column 8, Line 54, delete "(670)." and insert -- (670), --, therefor.
23. In Column 9, Line 3, delete "(1998):" and insert -- (1998); --, therefor.
24. In Column 9, Line 17, delete "Dabcyl." and insert -- Dabcyl, --, therefor.

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,975,423 B2

25. In Column 9, Line 46, delete ""quencher."" and insert -- "quencher," --, therefor.
26. In Column 10, Line 3, delete "phosphonates." and insert -- phosphonates, --, therefor.
27. In Column 10, Line 10, delete "al." and insert -- al., --, therefor.
28. In Column 10, Line 11, delete "Acids?"." and insert -- Acids?", --, therefor.
29. In Column 10, Line 21, delete "Nt.BstNBI." and insert -- Nt.BstNBI, --, therefor.
30. In Column 10, Line 43, delete "7,488,578," and insert -- 7,488,578. --, therefor.
31. In Column 10, Line 66, delete "Maniatis." and insert -- Maniatis, --, therefor.
32. In Column 11, Line 1, delete "Edition." and insert -- Edition, --, therefor.
33. In Column 11, Line 57, delete "I." and insert -- I, --, therefor.
34. In Column 12, Line 27, delete "(thi.univie.ac.at/ivo/RNA/)," and insert
-- (tbi.univie.ac.at./ivo/RNA/), --, therefor.
35. In Column 12, Line 67, delete "(SantaLucia." and insert -- (SantaLucia, --, therefor.
36. In Column 14, Line 5, delete "(LAMP)." and insert -- (LAMP), --, therefor.
37. In Column 14, Line 7, delete "(RPA)." and insert -- (RPA), --, therefor.
38. In Column 14, Line 48, delete "I D." and insert -- ID. --, therefor.
39. In Column 19, Line 27, delete "Biosystems." and insert -- Biosystems, --, therefor.
40. In Column 19, Line 38, delete "(gi157650036:262250-263203)." and insert
-- (gil57650036:262250-263203). --, therefor.
41. In Column 19, Line 45, delete "linker." and insert -- linker, --, therefor.
42. In Column 19, Line 49, delete "Bothell." and insert -- Bothell, --, therefor.
43. In Column 20, Line 30, delete "ng/p L" and insert -- ng/µL --, therefor.
44. In Column 21, Line 42, delete "Ipswich." and insert -- Ipswich, --, therefor.
45. In Column 21, Line 44, delete "Polymerase 1," and insert -- Polymerase I, --, therefor.
46. In Column 22, Line 43, delete "2 4-7." and insert -- 2 4-7, --, therefor.
47. In Column 23, Line 30, delete "(12228." and insert -- (12228, --, therefor.
48. In Column 23, Line 61, delete "5510." and insert -- 5510, --, therefor.
49. In Column 26, Line 10, delete "*[e*f" and insert -- *[e+f --, therefor.
50. In Column 28, Line 28, delete "A." and insert -- A, --, therefor.
51. In Column 32, Line 12, in the table, delete "Interaction" and insert -- interaction --, therefor.
52. In Column 35, Line 37, delete "80)." and insert -- 80), --, therefor.
53. In Column 36, Line 62, delete "86)." and insert -- 86), --, therefor.
54. In Column 38, Line 12, delete "PCR. Ed. S. A. Bustin." and insert -- PCR, Ed. S. A. Bustin, --, therefor.
55. In Column 38, Line 15, delete "Reports." and insert -- Reports, --, therefor.
56. In Column 38, Line 16, delete "E." and insert -- E, --, therefor.
57. In Column 38, Line 23, delete "XNA." and insert -- XNA, --, therefor.
58. In Column 38, Line 37, delete "Microbiol." and insert -- Microbiol., --, therefor.
59. In Column 38, Line 40, delete "SantaLucia." and insert -- SantaLucia, --, therefor.
60. In Column 38, Line 52, delete "Smith." and insert -- Smith, --, therefor.
61. In Column 38, Line 53, delete "Edition." and insert -- Edition, --, therefor.
62. In Column 38, Line 55, delete "al." and insert -- al., --, therefor.

In the Claims
63. In Column 71, Line 53, in Claim 1, delete "sequence:" and insert -- sequence; --, therefor.